United States Patent
Song

(10) Patent No.: US 9,701,742 B2
(45) Date of Patent: Jul. 11, 2017

(54) ANTI-PROPERDIN ANTIBODIES AND USES THEREOF

(75) Inventor: Wenchao Song, Bryn Mawr, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 421 days.

(21) Appl. No.: 14/130,250

(22) PCT Filed: Jun. 29, 2012

(86) PCT No.: PCT/US2012/044974
§ 371 (c)(1),
(2), (4) Date: Apr. 4, 2014

(87) PCT Pub. No.: WO2013/006449
PCT Pub. Date: Jan. 10, 2013

(65) Prior Publication Data
US 2014/0212427 A1     Jul. 31, 2014

Related U.S. Application Data

(60) Provisional application No. 61/503,900, filed on Jul. 1, 2011.

(51) Int. Cl.
*A61K 39/395* (2006.01)
*C07K 16/18* (2006.01)

(52) U.S. Cl.
CPC .......... *C07K 16/18* (2013.01); *C07K 2317/24* (2013.01); *C07K 2317/34* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 6,333,034 B1 | 12/2001 | Gupta-Bansal et al. |
| 2003/0198636 A1 | 10/2003 | Gupta-Bansal et al. |
| 2006/0093599 A1 | 5/2006 | Gazit-Bornstein et al. |
| 2007/0274989 A1 | 11/2007 | Fung et al. |
| 2010/0263061 A1 | 10/2010 | Song |
| 2011/0008340 A1* | 1/2011 | Bansal ............... C07K 16/18 424/133.1 |
| 2013/0295102 A1 | 11/2013 | Johnson et al. |

FOREIGN PATENT DOCUMENTS

| | | |
|---|---|---|
| JP | 2008-518636 A | 6/2008 |
| WO | 2004/075837 A2 | 6/2005 |
| WO | WO-2006/052591 A2 | 5/2006 |
| WO | WO 2008/154018 | * 12/2008 |

OTHER PUBLICATIONS

Written Opinion of the International Searching Authority of PCT/US12/44974 (Jan. 1, 2014).*
Rudikoff et al., Proc Natl Acad Sci USA 79: 1979-1983 (1982).*
Colman, Research in Immunology 145: 33-36 (1994).*
Kussie et al., J. Immunol. 152: 146-152 (1994).*
Chen et al., EMBO J., 14: 2784-2794 (1995).*
ImmunoGlobe: The Art of Selecting an Epitope downloaded Oct. 25, 2016, last modified Oct. 14, 2016; immunoglobe.com/epitope-selection.html.*
Ricklin et al., "Complement-targeted therapeutics," Nat Biotechnol, 2007, 25(11): 1265-1275.
Blom et al., "Comment on 'The influence of the proinflammatory cytokine, osteopontin, on autoimmune demyelinating disease,'" Science, 2003, 299(5614): 1845a.
Bendele, "Animal models of rheumatoid arthritis," J Musculoskelet Neuronal Interact, 2001, 1(4): 377-385.
Carden et al., "Pathophysiology of ischaemia-reperfusion injury," J Pathol, 2000, 190(3):255-266.
Eefting et al., "Role of apoptosis in reperfusion injury," Cardiovasc Res, 2004, 61(3): 414-426.
Gupta-Bansal et al., "Inhibition of complement alternative pathway function with anti-properdin monoclonal antibodies," Mol Immunol, 2000, 37(5): 191-201.
Spitzer et al., "Properdin can initiate complement activation by binding specific target surfaces and providing a platform for de novo convertase assembly," J Immunol, 2007, 179(4): 2600-2608.
Ferreira et al., "Critical role of the c-terminal domains of factor H in regulating complement activation at cell surfaces," J Immunol, 2006, 177(9): 6308-6316.
Miwa et al., "Crry, but not CD59 and DAF, is indispensable for murine erythrocyte protection in vivo from spontaneous complement attack," Blood, 2002, 99(10): 3707-3716.
Ueda et al., "Probing Functional Sites on Complement Protein B With Monoclonal Antibodies," 1987, J. Immunol., 138:1143-1149.
Perdikoulis et al., "Expression and characterisation of the thrombospondin type I repeats of human properdin," Biochim Biophys Acta. 1548(2):265-77 (2001).

* cited by examiner

*Primary Examiner* — Phillip Gambel
(74) *Attorney, Agent, or Firm* — Clark & Elbing LLP

(57) ABSTRACT

This invention relates to selective inhibition of the alternative pathway (AP) of the complement system using an anti-properdin antibody. Specifically, the invention relates to methods of treating an AP-mediated pathology or AP-mediated condition in an individual by contacting the individual with an anti-properdin antibody.

20 Claims, 32 Drawing Sheets

Amino acid sequence of human properdin

MITEGAQAPRLLLPPLLLLTLPATGSDPVLCFTQYEESSGKCK
GLLGGGVSVEDCCLNTAFAYQKRSGGLCQPCRSPRWSLWST
WAPCSVTCSEGSQLRYRRCVGWNGQCSGKVAPGTLEWQLQ
ACEDQQCCPEMGGWSGWGPWEPCSVTCSKGTRTRRACN
HPAPKCGGHCPGQAQESEACDTQQVCPTHGAWATWGPWT
PCSASCHGGPHEPKETRSRKCSAPEPSQKPPGKPCPGLAYEQ
RRCTGLPPCPVAGGWGPWGPVSPCPVTCGLGQTMEQRTCN
HPVPQHGGPFCAGDATRTHICNTAVPCPVDGEWDSWGEWS
PCIRRNMKSISCQEIPGQQSRGRTCRGRKFDGHRCAGQQQD
IRHCYSIQHCPLKGSWSEWSTWGLCMPPCGPNPTRARQRLC
TPLLPKYPPTVSMVEGQGEKNVTFWGRPLPRCEELQGQKLV
VEEKRPCLHVPACKDPEEEEL (SEQ ID No: 54)

Figure 5A

TSR domains of human properdin

TSR-0: DPVLCFTQYEESSGKCKGLLGGGVSVEDCCLNTAFAYQKRSGGLCQPCR (SEQ ID NO: 55)

TSR-1: SPRWSLWSTWAPCSVTCSEGSQLRYRRCVGWNGQCSGKVAPGTLEWQLQACEDQQCCP (SEQ ID NO: 56)

TSR-2: EMGGWSGWGPWEPCSVTCSKGTRTRRRACNHPAPKCGGHCPGQAQESEACDTQQVCP (SEQ ID NO: 57)

TSR-3: THGAWATWGPWTPCSASCHGGPHEPKETRSRKCSAPEPSQKPPGKPCPGLAYEQRRCTGLPPCP (SEQ ID NO: 58)

TSR-4: VAGGWGPWGPVSPCPVTCGLGQTMEQRTCNHPVPQHGGPFCAGDATRTHICNTAVPCP (SEQ ID NO: 59)

TSR-5: VDGEWDSWGEWSPCIRRNMKSISCQEIPGQQSRGRTCRGRKFDGHRCAGQQDIRHCYSIQHCP (SEQ ID NO: 60)

TSR-6: LKGSWSEWSTWGLCMPPCGPNPTRARQRLCTPLLPKYPPTVSMVEGQGEKNVTFWGRPLPRCEELQGQKLVVEEKRPCLHVPACKDPEEEL (SEQ ID NO: 61)

Figure 5B

Nucleic acid and amino acid sequence of VH of mAb 19.1. Signal peptide is underlined and CDR1, CDR2 and CDR3 sequences are bolded and highlighted in gray.

(SEQ ID NO: 1)
(SEQ ID NO: 2)

CDR1 (SEQ ID NO: 3)
CDR2 (SEQ ID NO: 4)
CDR3 (SEQ ID NO: 5)

Nucleic acid and amino acid sequence of VL of mAb 19.1. Signal peptide is underlined and CDR1, CDR2 and CDR3 sequences are bolded and highlighted in gray.

(SEQ ID NO: 6)
(SEQ ID NO: 7)

CDR1 (SEQ ID NO: 8)
CDR2 (SEQ ID NO: 9)
CDR3 (SEQ ID NO: 10)

Human VL sequence 3-11.01

M R A P A Q L L P L L L L L L W L P D T T G
D I V M T Q S P D S L A V S L G E R A T I N C
K S S Q S V L Y S S N N K N Y L A W Y Q Q K P
G Q P P K L L I Y W A S T R E S G V P D R F S
G S G S G T D F T L T I S S L Q A E D V A V Y
Y C Q Q Y Y S T P (SEQ ID NO: 50)

Human JK3 sequence:

F T F G P G T K V D I K (SEQ ID NO: 62)

Humanized 2S VL_3-11.01:

M R A P A Q L L P L L L L L L W L P D T T G
D I V M T Q S P D S L A V S L G E R A T I N C
K A S Q S V D Y D G D S Y M N W Y Q Q K P G Q
P P K L L I Y A A S N L E S G V P D R F S G S
G S G T D F T L T I S S L Q A E D V A V Y Y C
Q Q S N E D P F T F G P G T K V D I K
(SEQ ID NO: 51)

Figure 16

Amino acid sequence of human IgG4 Constant Heavy chain region with S228P mutation ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVESKYGPPCPPCPAPEFLGGPSV
FLFPPKPKDTLMISRTPEVTCVVVDVSQEDPEVQFNWYVDGVEVHNAKTKPREEQFNSTY
RVVSVLTVLHQDWLNGKEYKCKVSNKGLPSSIEKTISKAKGQPREPQVYTLPPSQEEMTK
NQVSLTCLVKGFYPSDIAVEWESNGQPENNYKTTPPVLDSDGSFFLYSRLTVDKSRWQEG
NVFSCSVMHEALHNHYTQKSLSLSPGK    (SEQ ID NO: 63)

Amino acid sequence of human Kappa Constant Light region

TVAAPSVFIFPPSDEQLKSGTASVVCLLNNFYPREAKVQWKVDNALQSGNSQESVTEQDS
KDSTYSLSSTLTLSKADYEKHKVYACEVTHQGLSSPVTKSFNRGEC    (SEQ ID NO: 64)

FIG. 17A cDNA sequence of human properdin used to make transgenic mice

TATCAACCCAGATAAAGCGGGACCTCCTCTCTGGTAGAGGTGCAGGGGGCAGTACTCAACATGATCACAGAGGGAGCG
CAGGCCCCCTCGATTGTTGCTGCCCGCCAGCCCCTGCCAGCCACAGGCTCACCCCGTGCTCTGC
TTCACCCAGTATGAAGAATCCTCCGGCAAGTGCAAGTGGGTGTCAGCGTGTCAGGGTGTCAGGGGCCTGGAAGACTGCTGTCTC
AACACTGCCTTTGCCTACCAGAAACGTAGTGCTCTGAGGGCCTTGCAGGTCCCCAGCGATGGTCCCTTTGGTCC
ACATGGGCCCCCTGTTCGGTGACGTGCCACCTGGGACCCTGCGGTACCGGCCTGTGTGGGCTGGAATGGGCAG
TGCTCTGGAAAGGTGCTGGCTGGCCACCTGGGCACCTGGGCAGCTGGCAGCTCCTTGCTCTGTCCCCAGGCGAGCC
GGCGGCTGGTCTGGCCTGCTCCCAAGTGTGGGGGCCCACTGGGACCCCTGTGACACCCAGCAG
TGTAATCACCCTGCTGCCCACACGGGAAGCCAGTGCGAAGGGAGTGCACCCTGGAGCCTCAGCCTGCCCAGAACCCTCCTGGGAAGCCCTGTGG
GTCCTGCCCCACACGGGAAGCCAGTGCGAAGCGAGTGCCCTGGACCTGTGCCGGCCTGATCACCCTGGGCCTGTG
CTAGCCTACGAGCAGCACGAGCACGAGCCAAGCCAGTGCCCTGGGCCTGCGGTGCCCAGACAACGGAGCGTGCAATCGCCTGCCCTGAGCATGGG
AGCCCCCTGCCTGTGCTGGAGCCCTGGCGATGCGAGCCCCTGTATCCGAACAGCTGCCATGTGCCGGGCAACAGCAGGATATCCGGCCAGTGC
GGCCCCCCTTCTGTGCTGGAGCCCTGCAGGGGAGTGCAGGACCTGCCAGCACTGCCCTTCGGGCCGGGCTGTGAAGGACCAGGATATCCGGCCAGTGC
GACTCGTGGGGGAGACCTGCAGGGCCCCGGAGTGCAGGACCACTGCCCTGTATCCGGCAAGTTTGACGGACATCGATGTGCCGGGCAACAGCAGGATATCCGGCCAGTGCACTGC
TACAGCATCCAGCACTCCGTGCTACCCGTGCCAGGGCGAGAAGGATCATGCGCGTGCACACCCTTTGCTCCCACACCGTTGCCAAGTACCGGCCCCACCGTTTCCATGGTGTCGGAA
CCTAATCATCCTACCCCGTGCCAGGGCGAGAAACGTGACCATGTCTACAGTCTGCACACCCTTTGCTCCCACACCGTTGCCCGCCTACAAGCTACAAGCTACAAGCAGCTGGTG
GGTCAGGCGAGAAACGTGACCATGTCTACAGTCTGCTCTGGGGGGAGACCCGCTGCCAAGAGACCCTGCTTGCAAAGACCCTCTTGCAAAGACCCTCTTGCAAAGACCTGCTTCCT
GTGGAGGAGAAACGACCATGTCTACAGTCTGCTCTGGGGGGAGACCCGCTGCCAAGAGACCCTGTGCAAATAAACCTTCAATAAACTAGCCCTCTTCCT
CCACTCTGAGCCCCCCGAGCCCTTCCAAACCTTCAATAAACTAGCCCTCTTCGAAAAAAAAAAAAAAAAAAAAAAAAAAAAA
AAAAAAAAAAAAAAAAAAAAAAAAAAAAAAAAAAAAAAAAAAAAAAAA  (SEQ ID NO: 67)

Figure 28

SEQUENCE LISTING

```
<160> NUMBER OF SEQ ID NOS: 67

<210> SEQ ID NO 1
<211> LENGTH: 427
<212> TYPE: DNA
<213> ORGANISM: Mus musculus

<400> SEQUENCE: 1
gagcatggct gtcttggggc tgctcttctg cctggtgaca ttcccaagct gtgtcctatc    60
ccaggtgcag ctcaagcagt caggacctgg cctagtgcag ccctcacaga gcctgtccat   120
ctcctgcaca gtctctggtt tctcattaac tacctatggt gttcactggg ttcgccagtc   180
tccaggaaag ggtctggaat ggctgggagt gatttggagt ggtggagaca cagactataa   240
tgcatctttc atatccagac tgcgcatcaa caaggacact tccaagagcc aagtttctt    300 taaaatgaac agtctgcaag ctgatgacac agccatttat tactgtgcca gaataagga    360 ctattatact aactacgact ttactatgga ctactggggt caaggaacct cagtcaccgt   420
ctcctca                                                              427

<210> SEQ ID NO 2
<211> LENGTH: 140
<212> TYPE: PRT
<213> ORGANISM: Mus musculus

<400> SEQUENCE: 2

Met Ala Val Leu Gly Leu Leu Phe Cys Leu Val Thr Phe Pro Ser Cys
1               5                   10                  15

Val Leu Ser Gln Val Gln Leu Lys Gln Ser Gly Pro Gly Leu Val Gln
                20                  25                  30

Pro Ser Gln Ser Leu Ser Ile Ser Cys Thr Val Ser Gly Phe Ser Leu
            35                  40                  45

Thr Thr Tyr Gly Val His Trp Val Arg Gln Ser Pro Gly Lys Gly Leu
        50                  55                  60

Glu Trp Leu Gly Val Ile Trp Ser Gly Gly Asp Thr Asp Tyr Asn Ala
65                  70                  75                  80

Ser Phe Ile Ser Arg Leu Arg Ile Asn Lys Asp Thr Ser Lys Ser Gln
                85                  90                  95

Val Phe Phe Lys Met Asn Ser Leu Gln Ala Asp Asp Thr Ala Tyr Tyr
                100                 105                 110

Cys Ala Arg Asn Lys Asp Tyr Tyr Thr Asn Tyr Asp Phe Thr Met Asp
            115                 120                 125

Tyr Trp Gly Gln Gly Thr Ser Val Thr Val Ser Ser
        130                 135                 140

<210> SEQ ID NO 3
<211> LENGTH: 10
<212> TYPE: PRT
<213> ORGANISM: Mus musculus
```

```
<400> SEQUENCE: 3

Gly Phe Ser Leu Thr Thr Tyr Gly Val His
1               5                   10

<210> SEQ ID NO 4
<211> LENGTH: 16
<212> TYPE: PRT
<213> ORGANISM: Mus musculus

<400> SEQUENCE: 4

Val Ile Trp Ser Gly Gly Asp Thr Asp Tyr Asn Ala Ser Phe Ile Ser
1               5                   10                  15

<210> SEQ ID NO 5
<211> LENGTH: 14
<212> TYPE: PRT
<213> ORGANISM: Mus musculus

<400> SEQUENCE: 5

Asn Lys Asp Tyr Tyr Thr Asn Tyr Asp Phe Thr Met Asp Tyr
1               5                   10

<210> SEQ ID NO 6
<211> LENGTH: 429
<212> TYPE: DNA
<213> ORGANISM: Mus musculus

<400> SEQUENCE: 6
ggcaggggga tcaagatgga atcacagact caggtcttcc tctccctgct gctctgggta      60
tctggtacct gtgggaacat tatgatgaca cagtcgccat catctctggc tgtgtctgca     120
ggagaaaagg tcactatgag ctgtaagtcc agtcaaagtg ttttatacag ttcaaatcag     180
aagaacttct tggcctggta ccagcagaaa ccaggacagt ctcctaaact gctgatctac     240
tgggcatcca ctagggaatc tggtgtccct gatcgcttca caggcagtgg atctgggaca     300
gattttattc ttacgatcaa cagtgtacaa gttgaagacc aggcagttta ttactgtcac     360
caataccctc tcctcgtaca cgttcggggg gggaccaagc tggaaataaa acgggctgat     420
gctgcacca                                                            429

<210> SEQ ID NO 7
<211> LENGTH: 132
<212> TYPE: PRT
<213> ORGANISM: Mus musculus

<400> SEQUENCE: 7

Met Glu Ser Gln Thr Gln Val Phe Leu Ser Leu Leu Leu Trp Val Ser
1               5                   10                  15

Gly Thr Cys Gly Asn Ile Met Met Thr Gln Ser Pro Ser Ser Leu Ala
                20                  25                  30

Val Ser Ala Gly Glu Lys Val Thr Met Ser Cys Lys Ser Ser Gln Ser
            35                  40                  45

Val Leu Tyr Ser Ser Asn Gln Lys Asn Phe Leu Ala Trp Tyr Gln Gln
        50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Ile Leu Thr Ile Asn Ser Val Gln Val Glu Asp Gln Ala Val Tyr
                100                 105                 110
```

Tyr Cys His Gln Tyr Leu Ser Ser Tyr Thr Phe Gly Gly Gly Thr Lys
            115                 120                 125

Leu Glu Ile Lys
       130

<210> SEQ ID NO 8
<211> LENGTH: 17
<212> TYPE: PRT
<213> ORGANISM: Mus musculus

<400> SEQUENCE: 8

Lys Ser Ser Gln Ser Val Leu Tyr Ser Ser Asn Gln Lys Asn Phe Leu
1               5                   10                  15

Ala

<210> SEQ ID NO 9
<211> LENGTH: 7
<212> TYPE: PRT
<213> ORGANISM: Mus musculus

<400> SEQUENCE: 9

Trp Ala Ser Thr Arg Glu Ser
1               5

<210> SEQ ID NO 10
<211> LENGTH: 8
<212> TYPE: PRT
<213> ORGANISM: Mus musculus

<400> SEQUENCE: 10

His Gln Tyr Leu Ser Ser Tyr Thr
1               5

<210> SEQ ID NO 11
<211> LENGTH: 487
<212> TYPE: DNA
<213> ORGANISM: Mus musculus

<400> SEQUENCE: 11
aacagcatat gatcagtgtc ctctccaaag tccttgaaca tagactctaa ccatggactg      60
gacctgggtc tttctcttcc tcctgtcagt aactgcaggt gtccactccc aggttcagct     120
gctgcagtct ggagctgagg tgatgaagcc tggggcctca gtgacccttt cctgcaaggc     180
tattggttac acattcattg actactggat agagtggata aagcagaggc ctggacatgg     240
ccttgagtgg attggagaga ttttcctgg aagtgggact attaatcaca atgagaagtt     300
caaggacaag gccagttttta gtgctcattc atcctccaac acagcctaca tgcaactcag     360
cagactgaca agtgaggact ctgccatcta ttactgtgca agagagggac tggactattg     420
gggccaaggc accactctca cagtctcctc agccaaaacg acacccccat ctgtctatcc     480
actggcc                                                                487

<210> SEQ ID NO 12
<211> LENGTH: 133
<212> TYPE: PRT
<213> ORGANISM: Mus musculus

<400> SEQUENCE: 12

Met Asp Trp Thr Trp Val Phe Leu Phe Leu Leu Ser Val Thr Ala Gly
1               5                   10                  15

Val His Ser Gln Val Gln Leu Leu Gln Ser Gly Ala Glu Val Met Lys
            20                  25                  30

Pro Gly Ala Ser Val Thr Leu Ser Cys Lys Ala Ile Gly Tyr Thr Phe
        35                  40                  45

Ile Asp Tyr Trp Ile Glu Trp Ile Lys Gln Arg Pro Gly His Gly Leu
    50                  55                  60

Glu Trp Ile Gly Glu Ile Phe Pro Gly Ser Gly Thr Ile Asn His Asn
65                  70                  75                  80

Glu Lys Phe Lys Asp Lys Ala Ser Phe Ser Ala His Ser Ser Ser Asn
                85                  90                  95

Thr Ala Tyr Met Gln Leu Ser Arg Leu Thr Ser Glu Asp Ser Ala Ile
            100                 105                 110

Tyr Tyr Cys Ala Arg Glu Gly Leu Asp Tyr Trp Gly Gln Gly Thr Thr
        115                 120                 125

Leu Thr Val Ser Ser
    130

<210> SEQ ID NO 13
<211> LENGTH: 10
<212> TYPE: PRT
<213> ORGANISM: Mus musculus

<400> SEQUENCE: 13

Gly Tyr Thr Phe Ile Asp Tyr Trp Ile Glu
1               5                   10

<210> SEQ ID NO 14
<211> LENGTH: 17
<212> TYPE: PRT
<213> ORGANISM: Mus musculus

<400> SEQUENCE: 14

Glu Ile Phe Pro Gly Ser Gly Thr Ile Asn His Asn Glu Lys Phe Lys
1               5                   10                  15

Asp

<210> SEQ ID NO 15
<211> LENGTH: 5
<212> TYPE: PRT
<213> ORGANISM: Mus musculus

<400> SEQUENCE: 15

Glu Gly Leu Asp Tyr
1               5

<210> SEQ ID NO 16
<211> LENGTH: 420
<212> TYPE: DNA
<213> ORGANISM: Mus musculus

<400> SEQUENCE: 16
ccaaaattca aagacaaaat ggattttcaa gtgcagattt tcagcttcct gctaatcagt      60
gcctcagtca taatatccag aggacaaatt gttctcaccc agtctccagc aatcatgtct     120
gcatctccag gggagagggt caccatgacc tgcagtgcca gctcaagtgt aagttatata     180
tactggtacc agcagaagtc aggcacgtcc cccaaaagat ggattttga cacatccaca     240 ctggcttctg gagtccctac tcgcttcagt ggcagtgggt ctgggacctc ttactctctc     300
acaatcagca gcatggagac tgaagatgct gccacttatt actgccagca gtggagtaga     360
aacccattca cgttcggttc ggggacaaag ttggaaataa aacgggctga tgctgcacca    420

<210> SEQ ID NO 17
<211> LENGTH: 128
<212> TYPE: PRT
<213> ORGANISM: Mus musculus

<400> SEQUENCE: 17

Met Asp Phe Gln Val Gln Ile Phe Ser Phe Leu Leu Ile Ser Ala Ser
1               5                  10                  15

Val Ile Ile Ser Arg Gly Gln Ile Val Leu Thr Gln Ser Pro Ala Ile
            20                  25                  30

Met Ser Ala Ser Pro Gly Glu Arg Val Thr Met Thr Cys Ser Ala Ser
        35                  40                  45

Ser Ser Val Ser Tyr Ile Tyr Trp Tyr Gln Gln Lys Ser Gly Thr Ser
    50                  55                  60

Pro Lys Arg Trp Ile Phe Asp Thr Ser Thr Leu Ala Ser Gly Val Pro
65                  70                  75                  80

Thr Arg Phe Ser Gly Ser Gly Ser Gly Thr Ser Tyr Ser Leu Thr Ile
                85                  90                  95

Ser Ser Met Glu Thr Glu Asp Ala Ala Thr Tyr Tyr Cys Gln Gln Trp
            100                 105                 110

Ser Arg Asn Pro Phe Thr Phe Gly Ser Gly Thr Lys Leu Glu Ile Lys
        115                 120                 125

<210> SEQ ID NO 18
<211> LENGTH: 10
<212> TYPE: PRT
<213> ORGANISM: Mus musculus

<400> SEQUENCE: 18

Ser Ala Ser Ser Ser Val Ser Tyr Ile Tyr
1               5                  10

<210> SEQ ID NO 19
<211> LENGTH: 7
<212> TYPE: PRT
<213> ORGANISM: Mus musculus

<400> SEQUENCE: 19

Asp Thr Ser Thr Leu Ala Ser
1               5

<210> SEQ ID NO 20
<211> LENGTH: 9
<212> TYPE: PRT
<213> ORGANISM: Mus musculus

<400> SEQUENCE: 20

Gln Gln Trp Ser Arg Asn Pro Phe Thr
1               5

<210> SEQ ID NO 21
<211> LENGTH: 464
<212> TYPE: DNA
<213> ORGANISM: Mus musculus

<400> SEQUENCE: 21
gagcatggct gtcttggggc tgctcttctg cctggtgaca ttcccaagct gtgtcctatc    60
ccaggtgcag ctgaagcagt caggacctgg cctagtgcag ccctcacaga gcctgtccat   120

-continued

```
cacctgcaca gtctctggtt tctcattaac tagctatggt gtacactggg ttcgccagtc    180
tccaggaaag ggtctggagt ggctgggagt gatatggagt ggtggaagca cagactataa    240
tgcagctttc atatccagac tgagcatcag caaagacact tccaagagcc aagttttctt    300
taaaatgaac agtctgcaac ctgatgacac agccatatat tactgtgcca gaaataaaga    360
cttctatagt aactacgact atactatgga actactgggg tcaaggaacc tcagtcaccg    420
tctcctcagc caaaacgaca ccccatctg tctatccact ggcc    464
```

<210> SEQ ID NO 22
<211> LENGTH: 141
<212> TYPE: PRT
<213> ORGANISM: Mus musculus
<400> SEQUENCE: 22

```
Met Ala Val Leu Gly Leu Leu Phe Cys Leu Val Thr Phe Pro Ser Cys
 1               5                  10                  15

Val Leu Ser Gln Val Gln Leu Lys Gln Ser Gly Pro Gly Leu Val Gln
            20                  25                  30

Pro Ser Gln Ser Leu Ser Ile Thr Cys Thr Val Ser Gly Phe Ser Leu
        35                  40                  45

Thr Ser Tyr Gly Val His Trp Val Arg Gln Ser Pro Gly Lys Gly Leu
    50                  55                  60

Glu Trp Leu Gly Val Ile Trp Ser Gly Gly Ser Thr Asp Tyr Asn Ala
65                  70                  75                  80

Ala Phe Ile Ser Arg Leu Ser Ile Ser Lys Asp Thr Ser Lys Ser Gln
                85                  90                  95

Val Phe Phe Lys Met Asn Ser Leu Gln Pro Asp Asp Thr Ala Ile Tyr
            100                 105                 110

Tyr Cys Ala Arg Asn Lys Asp Phe Tyr Ser Asn Tyr Asp Tyr Thr Met
        115                 120                 125

Asp Tyr Trp Gly Gln Gly Thr Ser Val Thr Val Ser Ser
    130                 135                 140
```

<210> SEQ ID NO 23
<211> LENGTH: 10
<212> TYPE: PRT
<213> ORGANISM: Mus musculus
<400> SEQUENCE: 23

```
Gly Phe Ser Leu Thr Ser Tyr Gly Val His
 1               5                  10
```

<210> SEQ ID NO 24
<211> LENGTH: 16
<212> TYPE: PRT
<213> ORGANISM: Mus musculus
<400> SEQUENCE: 24

```
Val Ile Trp Ser Gly Gly Ser Thr Asp Tyr Asn Ala Ala Phe Ile Ser
 1               5                  10                  15
```

<210> SEQ ID NO 25
<211> LENGTH: 14
<212> TYPE: PRT
<213> ORGANISM: Mus musculus
<400> SEQUENCE: 25

```
Asn Lys Asp Phe Tyr Ser Asn Tyr Asp Tyr Thr Met Asp Tyr
 1               5                  10
```

<210> SEQ ID NO 26
<211> LENGTH: 414
<212> TYPE: DNA
<213> ORGANISM: Mus musculus

<400> SEQUENCE: 26

```
atggaatcac agactcaggt cttcctctcc ctgctgctct gggtatctgg tacctgtggg      60
aacattatga tgacacagtc gccatcattt ttggctgtgt ctgcaggaga aaaggtcact     120
ttgagctgta agtccagtca aagtgtttta tacagttcaa atcagaagaa cttcttggcc     180
tggtaccagc agaaaccagg gcagtctcct aaactgctga tctactgggc atccactagg     240
gaatctggtg tccctgatcg cttcacaggc agtggatctg gacagatttt actcttacc      300
atcagcagtg tacaagctga agacctggca gtttattact gtcatcaata cctctcctcg     360
tacacgttcg gaggggggac caagctggaa ataaaacggg ctgatgctgc acca           414
```

<210> SEQ ID NO 27
<211> LENGTH: 132
<212> TYPE: PRT
<213> ORGANISM: Mus musculus

<400> SEQUENCE: 27

Met Glu Ser Gln Thr Gln Val Phe Leu Ser Leu Leu Leu Trp Val Ser
1               5                   10                  15

Gly Thr Cys Gly Asn Ile Met Met Thr Gln Ser Pro Ser Phe Leu Ala
            20                  25                  30

Val Ser Ala Gly Glu Lys Val Thr Leu Ser Cys Lys Ser Ser Gln Ser
        35                  40                  45

Val Leu Tyr Ser Ser Asn Gln Lys Asn Phe Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Thr Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys His Gln Tyr Leu Ser Ser Tyr Thr Phe Gly Gly Gly Thr Lys
        115                 120                 125

Leu Glu Ile Lys
    130

<210> SEQ ID NO 28
<211> LENGTH: 17
<212> TYPE: PRT
<213> ORGANISM: Mus musculus

<400> SEQUENCE: 28

Lys Ser Ser Gln Ser Val Leu Tyr Ser Ser Asn Gln Lys Asn Phe Leu
1               5                   10                  15

Ala

<210> SEQ ID NO 29
<211> LENGTH: 7
<212> TYPE: PRT
<213> ORGANISM: Mus musculus

<400> SEQUENCE: 29

Trp Ala Ser Thr Arg Glu Ser
1               5

<210> SEQ ID NO 30
<211> LENGTH: 8
<212> TYPE: PRT
<213> ORGANISM: Mus musculus

<400> SEQUENCE: 30

His Gln Tyr Leu Ser Ser Tyr Thr
1               5

<210> SEQ ID NO 31
<211> LENGTH: 451
<212> TYPE: DNA
<213> ORGANISM: Mus musculus

<400> SEQUENCE: 31
atggaattga tctgggtctt tctcttcctc ctgtcagtaa ctgcaggtgt ccactctgag    60
gtccagcttc agcagtctgg agttgagctg gtgaggcctg ggtcctcagt gaagatgtcc   120
tgcaagactt ctggatatac attyacagcc tacggtataa actgggtgaa gcagaggcct   180
ggacagggcc tggaatggat tggatatatt tatattggaa atggttatac tgactacaat   240
gagaagttca aggcaaggc cacactgact tcagacacat cctccagcac agcctacatg   300
cagctcagca gcctggcatc tgaggactct gcaatctatt tctgtcaaga tcggggtggg   360
acgaggacta tgctatggac ttctggggtc aaggaacctc agtcaccgtc tcctcagcca   420
aaacaacagc cccatcggtc tatccatggc c                                 451

<210> SEQ ID NO 32
<211> LENGTH: 139
<212> TYPE: PRT
<213> ORGANISM: Mus musculus
<220> FEATURE:
<221> NAME/KEY: misc_feature
<222> LOCATION: (48)..(48)
<223> OTHER INFORMATION: Xaa can be any naturally occurring amino acid

<400> SEQUENCE: 32

Met Glu Leu Ile Trp Val Phe Leu Phe Leu Leu Ser Val Thr Ala Gly
1               5                   10                  15

Val His Ser Glu Val Gln Leu Gln Gln Ser Gly Val Glu Leu Val Arg
                20                  25                  30

Pro Gly Ser Ser Val Lys Met Ser Cys Lys Thr Ser Gly Tyr Thr Xaa
            35                  40                  45

Thr Ala Tyr Gly Ile Asn Trp Val Lys Gln Arg Pro Gly Gln Gly Leu
    50                  55                  60

Glu Trp Ile Gly Tyr Ile Tyr Ile Gly Asn Gly Tyr Thr Asp Tyr Asn
65                  70                  75                  80

Glu Lys Phe Lys Gly Lys Ala Thr Leu Thr Ser Asp Thr Ser Ser Ser
                85                  90                  95

Thr Ala Tyr Met Gln Leu Ser Ser Leu Ala Ser Glu Asp Ser Ala Ile
            100                 105                 110

Tyr Phe Cys Ala Arg Ser Gly Trp Asp Glu Asp Tyr Ala Met Asp Phe
        115                 120                 125

Trp Gly Gln Gly Thr Ser Val Thr Val Ser Ser
    130                 135

<210> SEQ ID NO 33

```
<211> LENGTH: 10
<212> TYPE: PRT
<213> ORGANISM: Mus musculus
<220> FEATURE:
<221> NAME/KEY: misc_feature
<222> LOCATION: (4)..(4)
<223> OTHER INFORMATION: Xaa can be any naturally occurring amino acid

<400> SEQUENCE: 33

Gly Tyr Thr Xaa Thr Ala Tyr Gly Ile Asn
1               5                   10

<210> SEQ ID NO 34
<211> LENGTH: 17
<212> TYPE: PRT
<213> ORGANISM: Mus musculus

<400> SEQUENCE: 34

Tyr Ile Tyr Ile Gly Asn Gly Tyr Thr Asp Tyr Asn Glu Lys Phe Lys
1               5                   10                  15

Gly

<210> SEQ ID NO 35
<211> LENGTH: 11
<212> TYPE: PRT
<213> ORGANISM: Mus musculus

<400> SEQUENCE: 35

Ser Gly Trp Asp Glu Asp Tyr Ala Met Asp Phe
1               5                   10

<210> SEQ ID NO 36
<211> LENGTH: 399
<212> TYPE: DNA
<213> ORGANISM: Mus musculus

<400> SEQUENCE: 36
atgagtgtgc ccactcaggt cctggggttg ctgctgctgt ggcttacagg tggcagatgt      60
gacatccaga tgactcagtc tccagcctcc ctatctgcat ctgtgggaga aactgtcacc     120
atcacatgtc gagcaagtga gaatatttac agttatttag catggtatca gcagaaacag     180
agaaaatctc ctcacctcct ggtctatcat gcaaaaacct tagcagaagg tgtgacatca     240
aggttcagtg gcagtggatc aggcacacag ttttctctga agatccacag cctgcagcct     300
gaagattttg ggacttatta ctgtcaacat cattatggtc ctcctcccac gttcggctcg     360
gggacaaagt tggaaataaa acgggctgat gctgcacca                            399

<210> SEQ ID NO 37
<211> LENGTH: 127
<212> TYPE: PRT
<213> ORGANISM: Mus musculus

<400> SEQUENCE: 37

Met Ser Val Pro Thr Gln Val Leu Gly Leu Leu Leu Leu Trp Leu Thr
1               5                   10                  15

Gly Gly Arg Cys Asp Ile Gln Met Thr Gln Ser Pro Ala Ser Leu Ser
            20                  25                  30

Ala Ser Val Gly Glu Thr Val Thr Ile Thr Cys Arg Ala Ser Glu Asn
        35                  40                  45

Ile Tyr Ser Tyr Leu Ala Trp Tyr Gln Gln Lys Gln Arg Lys Ser Pro
    50                  55                  60
```

```
His Leu Leu Val Tyr His Ala Lys Thr Leu Ala Glu Gly Val Thr Ser
 65                  70                  75                  80

Arg Phe Ser Gly Ser Gly Ser Gly Thr Gln Phe Ser Leu Lys Ile His
                 85                  90                  95

Ser Leu Gln Pro Glu Asp Phe Gly Thr Tyr Tyr Cys Gln His His Tyr
            100                 105                 110

Gly Pro Pro Pro Thr Phe Gly Ser Gly Thr Lys Leu Glu Ile Lys
            115                 120                 125
```

<210> SEQ ID NO 38
<211> LENGTH: 11
<212> TYPE: PRT
<213> ORGANISM: Mus musculus

<400> SEQUENCE: 38

```
Arg Ala Ser Glu Asn Ile Tyr Ser Tyr Leu Ala
 1               5                  10
```

<210> SEQ ID NO 39
<211> LENGTH: 7
<212> TYPE: PRT
<213> ORGANISM: Mus musculus

<400> SEQUENCE: 39

```
His Ala Lys Thr Leu Ala Glu
 1               5
```

<210> SEQ ID NO 40
<211> LENGTH: 9
<212> TYPE: PRT
<213> ORGANISM: Mus musculus

<400> SEQUENCE: 40

```
Gln His His Tyr Gly Pro Pro Pro Thr
 1               5
```

<210> SEQ ID NO 41
<211> LENGTH: 116
<212> TYPE: PRT
<213> ORGANISM: Homo sapiens

<400> SEQUENCE: 41

```
Met Lys His Leu Trp Phe Phe Leu Leu Leu Val Ala Ala Pro Arg Trp
 1               5                  10                  15

Val Leu Ser Gln Val Gln Leu Gln Glu Ser Gly Pro Gly Leu Val Lys
                 20                  25                  30

Pro Ser Glu Thr Leu Ser Leu Thr Cys Thr Val Ser Gly Gly Ser Ile
             35                  40                  45

Ser Ser Tyr Tyr Trp Ser Trp Ile Arg Gln Pro Pro Gly Lys Gly Leu
         50                  55                  60

Glu Trp Ile Gly Tyr Ile Tyr Tyr Ser Gly Ser Thr Asn Tyr Asn Pro
 65                  70                  75                  80

Ser Leu Lys Ser Arg Val Thr Ile Ser Val Asp Thr Ser Lys Asn Gln
                 85                  90                  95

Phe Ser Leu Lys Leu Ser Ser Val Thr Ala Ala Asp Thr Ala Val Tyr
            100                 105                 110

Tyr Cys Ala Arg
        115
```

<210> SEQ ID NO 42

```
<211> LENGTH: 141
<212> TYPE: PRT
<213> ORGANISM: Mus musculus

<400> SEQUENCE: 42

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Phe Ser Leu
        35                  40                  45

Thr Thr Tyr Gly Val His Trp Ile Arg Gln Pro Pro Gly Lys Gly Leu
    50                  55                  60

Glu Trp Ile Gly Val Ile Trp Ser Gly Gly Asp Thr Asp Tyr Asn Ala
65                  70                  75                  80

Ser Phe Ile Ser Arg Val Thr Ile Ser Val Asp Thr Ser Lys Asn Gln
                85                  90                  95

Phe Ser Leu Lys Leu Ser Ser Val Thr Ala Ala Asp Thr Ala Val Tyr
            100                 105                 110

Tyr Cys Ala Arg Asn Lys Asp Tyr Tyr Thr Asn Tyr Asp Phe Thr Met
        115                 120                 125

Asp Tyr Trp Gly Gln Gly Thr Thr Val Thr Val Ser Ser
    130                 135                 140

<210> SEQ ID NO 43
<211> LENGTH: 97
<212> TYPE: PRT
<213> ORGANISM: Homo sapiens

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 44
<211> LENGTH: 141
<212> TYPE: PRT
<213> ORGANISM: Mus musculus

<400> SEQUENCE: 44

Met Ala Val Leu Gly Leu Leu Phe Cys Leu Val Thr Phe Pro Ser Cys
1               5                   10                  15

Val Leu Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Leu
        35                  40                  45

Thr Thr Tyr Gly Val His Trp Val Arg Gln Ala Pro Gly Lys Gly Leu
```

50                  55                  60
Glu Trp Val Ser Val Ile Trp Ser Gly Gly Asp Thr Asp Tyr Asn Ala
 65                  70                  75                  80

Ser Phe Ile Ser Arg Phe Thr Ile Ser Arg Asp Asn Ser Lys Asn Thr
                 85                  90                  95

Leu Tyr Leu Gln Met Asn Ser Leu Arg Ala Glu Asp Thr Ala Val Tyr
            100                 105                 110

Tyr Cys Ala Arg Asn Lys Asp Tyr Tyr Asn Tyr Asp Phe Thr Met
        115                 120                 125

Asp Tyr Trp Gly Gln Gly Thr Thr Val Thr Val Ser Ser
        130                 135                 140

<210> SEQ ID NO 45
<211> LENGTH: 99
<212> TYPE: PRT
<213> ORGANISM: Homo sapiens

<400> SEQUENCE: 45

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
             20                  25                  30

Ser Asn Asn Lys Asn Tyr Leu Ala Trp Tyr Gln Gln Lys Pro Gly Gln
         35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Thr Asp Phe Thr Leu Thr Ile Ser
 65                  70                  75                  80

Ser Leu Gln Ala Glu Asp Val Ala Val Tyr Tyr Cys Gln Gln Tyr Tyr
                 85                  90                  95

Ser Thr Pro

<210> SEQ ID NO 46
<211> LENGTH: 12
<212> TYPE: PRT
<213> ORGANISM: Homo sapiens

<400> SEQUENCE: 46

Tyr Thr Phe Gly Gln Gly Thr Lys Leu Glu Ile Lys
 1               5                  10

<210> SEQ ID NO 47
<211> LENGTH: 132
<212> TYPE: PRT
<213> ORGANISM: Mus musculus

<400> SEQUENCE: 47

Met Glu Ser Gln Thr Gln Val Phe Leu Ser Leu Leu Leu Trp Val Ser
 1               5                  10                  15

Gly Thr Cys Gly Asp Ile Val Met Thr Gln Ser Pro Asp Ser Leu Ala
             20                  25                  30

Val Ser Leu Gly Glu Arg Ala Thr Ile Asn Cys Lys Ser Ser Gln Ser
         35                  40                  45

Val Leu Tyr Ser Ser Asn Gln Lys Asn Phe Leu Ala Trp Tyr Gln Gln
     50                  55                  60

Lys Pro Gly Gln Pro Pro Lys Leu Leu Ile Tyr Trp Ala Ser Thr Arg
 65                  70                  75                  80

-continued

Glu Ser Gly Val Pro Asp Arg Phe Ser Gly Ser Gly Ser Gly Thr Asp
            85                  90                  95

Phe Thr Leu Thr Ile Ser Ser Leu Gln Ala Glu Asp Val Ala Val Tyr
        100                 105                 110

Tyr Cys His Gln Tyr Leu Ser Ser Tyr Thr Phe Gly Gln Gly Thr Lys
    115                 120                 125

Leu Glu Ile Lys
    130

<210> SEQ ID NO 48
<211> LENGTH: 98
<212> TYPE: PRT
<213> ORGANISM: Homo sapiens

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 49
<211> LENGTH: 133
<212> TYPE: PRT
<213> ORGANISM: Mus musculus

<400> SEQUENCE: 49

Met Asp Trp Thr Trp Val Phe Leu Phe Leu Leu Ser Val Thr Ala Gly
1               5                   10                  15

Val His Ser Gln Val Gln Leu Val Gln Ser Gly Ala Glu Val Lys Lys
            20                  25                  30

Pro Gly Ser Ser Val Lys Val Ser Cys Lys Ala Ser Gly Tyr Thr Phe
        35                  40                  45

Ile Asp Tyr Trp Ile Glu Trp Val Arg Gln Ala Pro Gly Gln Gly Leu
    50                  55                  60

Glu Trp Met Gly Glu Ile Phe Pro Gly Ser Gly Thr Ile Asn His Asn
65                  70                  75                  80

Glu Lys Phe Lys Asp Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Glu Gly Leu Asp Tyr Trp Gly Gln Gly Thr Leu
        115                 120                 125

Val Thr Val Ser Ser
    130

<210> SEQ ID NO 50
<211> LENGTH: 115
<212> TYPE: PRT

<213> ORGANISM: Homo sapiens

<400> SEQUENCE: 50

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Arg Ala Ser Gln Ser
        35                  40                  45

Val Ser Ser Tyr Leu Ala Trp Tyr Gln Gln Lys Pro Gly Gln Ala Pro
    50                  55                  60

Arg Leu Leu Ile Tyr Asp Ala Ser Asn Arg Ala Thr Gly Ile Pro Ala
65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Val Tyr Tyr Cys Gln Gln Arg Ser
            100                 105                 110

Asn Trp Pro
        115

<210> SEQ ID NO 51
<211> LENGTH: 126
<212> TYPE: PRT
<213> ORGANISM: Mus musculus

<400> SEQUENCE: 51

Met Glu Ala Pro Ala Gln Leu Leu Phe Leu Leu Leu Leu Trp Leu Pro
1               5                   10                  15

Asp Thr Thr Gly Glu Ile Val Leu Thr Gln Ser Pro Ala Thr Leu Ser
            20                  25                  30

Leu Ser Pro Gly Glu Arg Ala Thr Leu Ser Cys Ser Ala Ser Ser Ser
        35                  40                  45

Val Ser Tyr Ile Tyr Trp Tyr Gln Gln Lys Pro Gly Gln Ala Pro Arg
    50                  55                  60

Leu Leu Ile Tyr Asp Thr Ser Thr Leu Ala Ser Gly Ile Pro Ala Arg
65                  70                  75                  80

Phe Ser Gly Ser Gly Ser Gly Thr Asp Phe Thr Leu Thr Ile Ser Ser
                85                  90                  95

Leu Glu Pro Glu Asp Phe Ala Val Tyr Tyr Cys Gln Gln Trp Ser Arg
            100                 105                 110

Asn Pro Phe Thr Phe Gly Pro Gly Thr Lys Val Asp Ile Lys
        115                 120                 125

<210> SEQ ID NO 52
<211> LENGTH: 32
<212> TYPE: PRT
<213> ORGANISM: Mus musculus

<400> SEQUENCE: 52

Arg Gly Arg Thr Cys Arg Gly Arg Lys Phe Asp Gly His Arg Cys Ala
1               5                   10                  15

Gly Gln Gln Gln Asp Ile Arg His Cys Tyr Ser Ile Gln His Cys Pro
            20                  25                  30

<210> SEQ ID NO 53
<211> LENGTH: 23
<212> TYPE: PRT
<213> ORGANISM: Mus musculus

<400> SEQUENCE: 53

Leu Val Val Glu Glu Lys Arg Pro Cys Leu His Val Pro Ala Cys Lys
1               5                   10                  15

Asp Pro Glu Glu Glu Leu
            20

<210> SEQ ID NO 54
<211> LENGTH: 469
<212> TYPE: PRT
<213> ORGANISM: Homo sapiens

<400> SEQUENCE: 54

Met Ile Thr Glu Gly Ala Gln Ala Pro Arg Leu Leu Leu Pro Pro Leu
1               5                   10                  15

Leu Leu Leu Leu Thr Leu Pro Ala Thr Gly Ser Asp Pro Val Leu Cys
            20                  25                  30

Phe Thr Gln Tyr Glu Glu Ser Ser Gly Lys Cys Lys Gly Leu Leu Gly
        35                  40                  45

Gly Gly Val Ser Val Glu Asp Cys Cys Leu Asn Thr Ala Phe Ala Tyr
    50                  55                  60

Gln Lys Arg Ser Gly Gly Leu Cys Gln Pro Cys Arg Ser Pro Arg Trp
65                  70                  75                  80

Ser Leu Trp Ser Thr Trp Ala Pro Cys Ser Val Thr Cys Ser Glu Gly
                85                  90                  95

Ser Gln Leu Arg Tyr Arg Arg Cys Val Gly Trp Asn Gly Gln Cys Ser
            100                 105                 110

Gly Lys Val Ala Pro Gly Thr Leu Glu Trp Gln Leu Gln Ala Cys Glu
        115                 120                 125

Asp Gln Gln Cys Cys Pro Glu Met Gly Gly Trp Ser Gly Trp Gly Pro
130                 135                 140

Trp Glu Pro Cys Ser Val Thr Cys Ser Lys Gly Thr Arg Thr Arg Arg
145                 150                 155                 160

Arg Ala Cys Asn His Pro Ala Pro Lys Cys Gly Gly His Cys Pro Gly
                165                 170                 175

Gln Ala Gln Glu Ser Glu Ala Cys Asp Thr Gln Gln Val Cys Pro Thr
            180                 185                 190

His Gly Ala Trp Ala Thr Trp Gly Pro Trp Thr Pro Cys Ser Ala Ser
        195                 200                 205

Cys His Gly Gly Pro His Glu Pro Lys Glu Thr Arg Ser Arg Lys Cys
210                 215                 220

Ser Ala Pro Glu Pro Ser Gln Lys Pro Pro Gly Lys Pro Cys Pro Gly
225                 230                 235                 240

Leu Ala Tyr Glu Gln Arg Arg Cys Thr Gly Leu Pro Pro Cys Pro Val
                245                 250                 255

Ala Gly Gly Trp Gly Pro Trp Gly Pro Val Ser Pro Cys Pro Val Thr
            260                 265                 270

Cys Gly Leu Gly Gln Thr Met Glu Gln Arg Thr Cys Asn His Pro Val
        275                 280                 285

Pro Gln His Gly Gly Pro Phe Cys Ala Gly Asp Ala Thr Arg Thr His
    290                 295                 300

Ile Cys Asn Thr Ala Val Pro Cys Pro Val Asp Gly Glu Trp Asp Ser
305                 310                 315                 320

Trp Gly Glu Trp Ser Pro Cys Ile Arg Arg Asn Met Lys Ser Ile Ser
                325                 330                 335

```
Cys Gln Glu Ile Pro Gly Gln Ser Arg Gly Arg Thr Cys Arg Gly
            340                 345                 350

Arg Lys Phe Asp Gly His Arg Cys Ala Gly Gln Gln Asp Ile Arg
            355                 360                 365

His Cys Tyr Ser Ile Gln His Cys Pro Leu Lys Gly Ser Trp Ser Glu
370                 375                 380

Trp Ser Thr Trp Gly Leu Cys Met Pro Pro Cys Gly Pro Asn Pro Thr
385                 390                 395                 400

Arg Ala Arg Gln Arg Leu Cys Thr Pro Leu Leu Pro Lys Tyr Pro Pro
            405                 410                 415

Thr Val Ser Met Val Glu Gly Gln Gly Glu Lys Asn Val Thr Phe Trp
            420                 425                 430

Gly Arg Pro Leu Pro Arg Cys Glu Glu Leu Gln Gly Gln Lys Leu Val
            435                 440                 445

Val Glu Glu Lys Arg Pro Cys Leu His Val Pro Ala Cys Lys Asp Pro
450                 455                 460

Glu Glu Glu Glu Leu
465

<210> SEQ ID NO 55
<211> LENGTH: 48
<212> TYPE: PRT
<213> ORGANISM: Homo sapiens

<400> SEQUENCE: 55

Asp Pro Val Leu Cys Phe Thr Gln Tyr Glu Glu Ser Ser Gly Lys Cys
1               5                   10                  15

Lys Gly Leu Leu Gly Gly Gly Val Ser Val Glu Asp Cys Cys Leu Asn
                20                  25                  30

Thr Ala Phe Ala Tyr Gln Lys Arg Ser Gly Gly Leu Cys Gln Pro Cys
            35                  40                  45

<210> SEQ ID NO 56
<211> LENGTH: 58
<212> TYPE: PRT
<213> ORGANISM: Homo sapiens

<400> SEQUENCE: 56

Ser Pro Arg Trp Ser Leu Trp Ser Thr Trp Ala Pro Cys Ser Val Thr
1               5                   10                  15

Cys Ser Glu Gly Ser Gln Leu Arg Tyr Arg Arg Cys Val Gly Trp Asn
                20                  25                  30

Gly Gln Cys Ser Gly Lys Val Ala Pro Gly Thr Leu Glu Trp Gln Leu
            35                  40                  45

Gln Ala Cys Glu Asp Gln Gln Cys Cys Pro
            50                  55

<210> SEQ ID NO 57
<211> LENGTH: 57
<212> TYPE: PRT
<213> ORGANISM: Homo sapiens

<400> SEQUENCE: 57

Glu Met Gly Gly Trp Ser Gly Trp Gly Pro Trp Glu Pro Cys Ser Val
1               5                   10                  15

Thr Cys Ser Lys Gly Thr Arg Thr Arg Arg Arg Ala Cys Asn His Pro
                20                  25                  30
```

```
Ala Pro Lys Cys Gly Gly His Cys Pro Gly Gln Ala Gln Glu Ser Glu
            35                  40                  45

Ala Cys Asp Thr Gln Gln Val Cys Pro
 50                  55
```

<210> SEQ ID NO 58
<211> LENGTH: 64
<212> TYPE: PRT
<213> ORGANISM: Homo sapiens

<400> SEQUENCE: 58

```
Thr His Gly Ala Trp Ala Thr Trp Gly Pro Trp Thr Pro Cys Ser Ala
 1               5                  10                  15

Ser Cys His Gly Gly Pro His Glu Pro Lys Glu Thr Arg Ser Arg Lys
                20                  25                  30

Cys Ser Ala Pro Glu Pro Ser Gln Lys Pro Pro Gly Lys Pro Cys Pro
            35                  40                  45

Gly Leu Ala Tyr Glu Gln Arg Arg Cys Thr Gly Leu Pro Pro Cys Pro
 50                  55                  60
```

<210> SEQ ID NO 59
<211> LENGTH: 58
<212> TYPE: PRT
<213> ORGANISM: Homo sapiens

<400> SEQUENCE: 59

```
Val Ala Gly Gly Trp Gly Pro Trp Gly Pro Val Ser Pro Cys Pro Val
 1               5                  10                  15

Thr Cys Gly Leu Gly Gln Thr Met Glu Gln Arg Thr Cys Asn His Pro
                20                  25                  30

Val Pro Gln His Gly Gly Pro Phe Cys Ala Gly Asp Ala Thr Arg Thr
            35                  40                  45

His Ile Cys Asn Thr Ala Val Pro Cys Pro
 50                  55
```

<210> SEQ ID NO 60
<211> LENGTH: 64
<212> TYPE: PRT
<213> ORGANISM: Homo sapiens

<400> SEQUENCE: 60

```
Val Asp Gly Glu Trp Asp Ser Trp Gly Glu Trp Ser Pro Cys Ile Arg
 1               5                  10                  15

Arg Asn Met Lys Ser Ile Ser Cys Gln Glu Ile Pro Gly Gln Gln Ser
                20                  25                  30

Arg Gly Arg Thr Cys Arg Gly Arg Lys Phe Asp Gly His Arg Cys Ala
            35                  40                  45

Gly Gln Gln Gln Asp Ile Arg His Cys Tyr Ser Ile Gln His Cys Pro
 50                  55                  60
```

<210> SEQ ID NO 61
<211> LENGTH: 92
<212> TYPE: PRT
<213> ORGANISM: Homo sapiens

<400> SEQUENCE: 61

```
Leu Lys Gly Ser Trp Ser Glu Trp Ser Thr Trp Gly Leu Cys Met Pro
 1               5                  10                  15

Pro Cys Gly Pro Asn Pro Thr Arg Ala Arg Gln Arg Leu Cys Thr Pro
                20                  25                  30
```

```
Leu Leu Pro Lys Tyr Pro Pro Thr Val Ser Met Val Glu Gly Gln Gly
        35                  40                  45

Glu Lys Asn Val Thr Phe Trp Gly Arg Pro Leu Pro Arg Cys Glu Glu
 50                  55                  60

Leu Gln Gly Gln Lys Leu Val Glu Glu Lys Arg Pro Cys Leu His
 65                  70                  75                  80

Val Pro Ala Cys Lys Asp Pro Glu Glu Glu Leu
                85                  90

<210> SEQ ID NO 62
<211> LENGTH: 12
<212> TYPE: PRT
<213> ORGANISM: Homo sapiens

<400> SEQUENCE: 62

Phe Thr Phe Gly Pro Gly Thr Lys Val Asp Ile Lys
1               5                   10

<210> SEQ ID NO 63
<211> LENGTH: 327
<212> TYPE: PRT
<213> ORGANISM: Homo sapiens

<400> SEQUENCE: 63

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

```
Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 64
<211> LENGTH: 106
<212> TYPE: PRT
<213> ORGANISM: Homo sapiens

<400> SEQUENCE: 64

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 65
<211> LENGTH: 19
<212> TYPE: DNA
<213> ORGANISM: Homo sapiens

<400> SEQUENCE: 65
atcagaggcc tgtgacacc                                                  19

<210> SEQ ID NO 66
<211> LENGTH: 19
<212> TYPE: DNA
<213> ORGANISM: Homo sapiens

<400> SEQUENCE: 66
ctgcccttgt agctcctca                                                  19

<210> SEQ ID NO 67
<211> LENGTH: 1603
<212> TYPE: DNA
<213> ORGANISM: Homo sapiens

<400> SEQUENCE: 67
tatcaaccca gataaagcgg gacctcctct ctggtagagg tgcagggggc agtactcaac     60
atgatcacag agggagcgca ggcccctcga ttgttgctgc cgccgctgct cctgctgctc    120
accctgccag ccacaggctc agaccccgtg ctctgcttca cccagtatga agaatcctcc    180
```

-continued

```
ggcaagtgca agggcctcct gggggtggt gtcagcgtgg aagactgctg tctcaacact      240
gcctttgcct accagaaacg tagtggtggg ctctgtcagc cttgcaggtc cccacgatgg      300
tccctttggt ccacatgggc ccctgttcg gtgacgtgct ctgagggctc ccagctgcgg       360
taccggcgct gtgtgggctg gaatgggcag tgctctggaa aggtggcacc tgggaccctg      420
gagtggcagc tccaggcctg tgaggaccag cagtgctgtc ctgagatggg cggctggtct     480
ggctgggggc cctgggagcc ttgctctgtc acctgctcca aagggacccg gacccgcagg     540
cgagcctgta atcaccctgc tcccaagtgt gggggccact gcccaggaca ggcacaggaa     600
tcagaggcct gtgacaccca gcaggtctgc cccacacacg gggcctgggc cacctggggc     660
ccctggaccc cctgctcagc ctcctgccac ggtggacccc acgaacctaa ggagacacga    720
agccgcaagt gttctgcacc tgagccctcc cagaaacctc ctgggaagcc ctgcccgggg     780
ctagcctacg agcagcggag gtgcaccggc ctgccaccct gcccagtggc tggggctgg     840 gggccttggg gccctgtgag ccctgccct gtgacctgtg gcctgggcca gaccatggaa      900
caacggacgt gcaatcaccc tgtgcccag catgggggcc ccttctgtgc tggcgatgcc       960
acccggaccc acatctgcaa cacagctgtg ccctgccctg tggatgggga gtgggactcg     1020 tgggggagt ggagccctg tatccgacgg aacatgaagt ccatcagctg tcaagaaatc      1080
ccgggccagc agtcacgcgg gaggacctgc aggggccgca gtttgacgg acatcgatgt     1140 gccgggcaac agcaggatat ccggcactgc tacagcatcc agcactgccc cttgaaagga    1200
tcatggtcag agtggagtac ctgggggctg tgcatgcccc cctgtggacc taatcctacc   1260
cgtgcccgcc agcgcctctg cacacccttg ctccccaagt acccgcccac cgtttccatg    1320
gtcgaaggtc agggcgagaa gaacgtgacc ttctggggga gaccgctgcc acggtgtgag    1380
gagctacaag ggcagaagct ggtggtggag gagaaacgac catgtctaca cgtgcctgct  1440
tgcaaagacc ctgaggaaga ggaactctaa cacttctctc ctccactctg agccccctga    1500
ccttccaaac ctcaataaac tagcctcttc gaaaaaaaaa aaaaaaaaaa aaaaaaaaa      1560 aaaaaaaaaa aaaaaaaaa aaaaaaaaa aaaaaaaaa aaa                           1603
```

ANTI-PROPERDIN ANTIBODIES AND USES THEREOF

CROSS-REFERENCE TO RELATED APPLICATIONS

This application is the U.S. national phase application filed under 35 U.S.C. §371 claiming benefit to International Patent Application No. PCT/US12/44974, filed on Jun. 29, 2012, which is entitled to priority to U.S. Provisional Patent Application No. 61/503,900, filed on Jul. 1, 2011, each of which applications is hereby incorporated herein by reference in its entirety.

STATEMENT REGARDING FEDERALLY SUPPORTED RESEARCH OR DEVELOPMENT

This invention was made with government support under AI085596 awarded by National Institute of Health. The government has certain rights in the invention.

BACKGROUND OF THE INVENTION

The complement system provides a first line of host defense against invading pathogens. Complement also plays a pathogenic role in human inflammatory diseases. Activation of the complement system occurs via three different pathways, the classical pathway (CP), the lectin pathway (LP) and the alternative pathway (AP). The CP is initiated by antigen-antibody binding. The LP is triggered when mannose-binding lectins (MBL) interact with surface sugar molecules on microorganisms. Activation of both pathways leads to the assembly of the CP C3 convertase C4b2a, although direct cleavage of C3 by MBL-associated serine proteases can also occur. The AP is a self-amplification loop driven by the AP C3 convertase, C3bBb. AP activation can occur secondary to CP or LP activation, or is initiated independently. In the latter case, a low level spontaneous C3 'tick-over' generates the initial C3bBb, which rapidly propagates the AP in the absence of adequate regulation. Thus, it is generally assumed that AP activation on non-self surfaces with no or insufficient negative regulation is considered a default process, whereas autologous cells typically avoid this outcome with the help of multiple membrane-bound and fluid phase complement inhibitory proteins. Under certain conditions, altered, damaged or stressed autologous cells and tissues can also activate AP and cause inflammatory injury.

In contrast to the existence of numerous inhibitory proteins, the plasma protein properdin is the only known positive regulator of the complement activation cascade. Properdin is a plasma glycoprotein of approximately 53 kDa with an estimated blood concentration of 5-10 µg/ml. It exists mostly as dimers, trimers and tetramers in a fixed ratio, in a head-to-tail conformation. The currently held view on properdin function is that it facilitates AP activation by extending the half-life of the nascent C3bBb convertase. According to this view, properdin plays a facilitating, but not essential, role in AP activation. Since activation of the CP and the LP will invariably trigger the AP amplification loop, it is expected that properdin will also indirectly promote CP- and LP-mediated complement activation. Thus, based on the prevailing knowledge prior to this invention, one may not regard properdin as an attractive anti-complement therapeutic target because it lacks specificity and is not indispensable for complement activation.

While all three pathways of complement activation help the host in fighting microbial infection, recent studies have shown that complement-mediated pathology in humans, such as age-related macular degeneration, atypical hemolytic uremic syndrome, paroxysmal nocturnal hemoglobinuria (PNH), rheumatoid arthritis, allergic asthma and ischemia reperfusion injury, is mainly mediated by the AP. Thus, there remains a need in the art for anti-complement compositions and methods of treating human inflammatory diseases by selectively inhibiting the AP while leaving intact the CP and the LP to fight pathogens and to protect the host from infection. The current invention fulfills this need.

SUMMARY

This invention relates to anti-properdin antibody and methods of inhibiting the alternative pathway (AP) of complement using an anti-properdin antibody.

In one embodiment, the invention is a composition comprising an antibody that specifically binds to properdin. In preferred embodiments, the properdin is human properdin. In some embodiments, the antibody of the invention is a monoclonal antibody. In some embodiments, the antibody of the invention is a humanized antibody. In some embodiments, the antibody of the invention is a chimeric antibody.

In one embodiment, the antibody of the invention comprises at least one of the CDRs selected from the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10. In another embodiment, the antibody of the invention comprises a heavy chain comprising the amino acid sequence of SEQ ID NO:2. In one embodiment, the antibody of the invention comprises a light chain comprising the amino acid sequence of SEQ ID NO:7. In another embodiment, the antibody of the invention comprises a heavy chain comprising the amino acid sequence of SEQ ID NO:2 and a light chain comprising the amino acid sequence of SEQ ID NO:7. In one embodiment, the antibody of the invention specifically binds to an epitope comprising at least one amino acid of SEQ ID NO:52.

In one embodiment, the antibody of the invention comprises at least one of the CDRs selected from the group consisting of: VH-CDR1: SEQ ID NO: 13; VH-CDR2: SEQ ID NO:14; VH-CDR3: SEQ ID NO:15; VL-CDR1: SEQ ID NO:18; VL-CDR2: SEQ ID so NO:19; and VL-CDR3: SEQ ID NO:20. In another embodiment, the antibody of the invention comprises a heavy chain comprising the amino acid sequence of SEQ ID NO:12. In one embodiment, the antibody of the invention comprises a light chain comprising the amino acid sequence of SEQ ID NO:17. In another embodiment, the antibody of the invention comprises a heavy chain comprising the amino acid sequence of SEQ ID NO:12 and a light chain comprising the amino acid sequence of SEQ ID NO:17. In one embodiment, the antibody of the invention specifically binds to an epitope comprising at least one amino acid of SEQ ID NO:53.

In one embodiment, the antibody of the invention comprises at least one of the CDRs selected from the group consisting of: VH-CDR1: SEQ ID NO:23; VH-CDR2: SEQ ID NO:24; VH-CDR3: SEQ ID NO:25; VL-CDR1: SEQ ID NO:28; VL-CDR2: SEQ ID NO:29; and VL-CDR3: SEQ ID NO:30. In another embodiment, the antibody of the invention comprises a heavy chain comprising the amino acid sequence of SEQ ID NO:22. In one embodiment, the antibody of the invention comprises a light chain comprising the amino acid sequence of SEQ ID NO:27. In another embodiment, the antibody of the invention comprises a heavy chain comprising the amino acid sequence of SEQ ID NO:22 and a light chain comprising the amino acid sequence of SEQ ID NO:27.

In one embodiment, the antibody of the invention comprises at least one of the CDRs selected from the group consisting of: VH-CDR1: SEQ ID NO:33; VH-CDR2: SEQ ID NO:34; VH-CDR3: SEQ ID NO:35; VL-CDR1: SEQ ID NO:38; VL-CDR2: SEQ ID NO:39; and VL-CDR3: SEQ ID NO:40. In another embodiment, the antibody of the invention comprises a heavy chain comprising the amino acid sequence of SEQ ID NO:32. In one embodiment, the antibody of the invention comprises a light chain comprising the amino acid sequence of SEQ ID NO:37. In another embodiment, the antibody of the invention comprises a heavy chain comprising the amino acid sequence of SEQ ID NO:32 and a light chain comprising the amino acid sequence of SEQ ID NO:37.

In one embodiment, the antibody of the invention comprises a heavy chain comprising the amino acid sequence of SEQ ID NO:42. In another embodiment, the antibody of the invention comprises a heavy chain comprising the amino acid sequence of SEQ ID NO:44. In one embodiment, the antibody of the invention comprises a light chain comprising the amino acid sequence of SEQ ID NO:47. In one embodiment, the antibody of the invention comprises a heavy chain comprising the amino acid sequence of SEQ ID NO:42 so and a light chain comprising the amino acid sequence of SEQ ID NO:47. In another embodiment, the antibody of the invention comprises a heavy chain comprising the amino acid sequence of SEQ ID NO:44 and a light chain comprising the amino acid sequence of SEQ ID NO:47.

In one embodiment, the antibody of the invention comprises a heavy chain comprising the amino acid sequence of SEQ ID NO:49. In one embodiment, the antibody of the invention comprises a light chain comprising the amino acid sequence of SEQ ID NO:51. In another embodiment, the antibody of the invention comprises a heavy chain comprising the amino acid sequence of SEQ ID NO:49 and a light chain comprising the amino acid sequence of SEQ ID NO:51.

In one embodiment, the antibody of the invention comprises a heavy chain to comprising the amino acid sequence of SEQ ID NO:2 and SEQ ID NO:63. In one embodiment, the antibody of the Invention comprises a light chain comprising the amino acid sequence of SEQ ID NO:7 and SEQ ID NO:64. In another embodiment, the antibody of the invention comprises a heavy chain comprising the amino acid sequences of SEQ ID NO:2 and SEQ ID NO:63 and a light chain comprising the amino acid sequences of SEQ ID NO:7 and SEQ ID NO:64.

In one embodiment, the antibody of the invention comprises a heavy chain comprising the amino acid sequence of SEQ ID NO: 12 and SEQ ID NO:63. In one embodiment, the antibody of the invention comprises a light chain comprising the amino acid sequence of SEQ ID NO: 17 and SEQ ID NO:64. In another embodiment, the antibody of the invention comprises a heavy chain comprising the amino acid sequences of SEQ ID NO: 12 and SEQ ID NO:63 and a light chain comprising the amino acid sequences of SEQ ID NO: 17 and SEQ ID NO:64.

In one embodiment, the antibody of the invention comprises a heavy chain comprising the amino acid sequence of SEQ ID NO:22 and SEQ ID NO:63. In one embodiment, the antibody of the invention comprises a light chain comprising the amino acid sequence of SEQ ID NO:27 and SEQ ID NO:64. In another embodiment, the antibody of the invention comprises a heavy chain comprising the amino acid sequences of SEQ ID NO:22 and SEQ ID NO:63 and a light chain comprising the amino acid sequences of SEQ ID NO:27 and SEQ ID NO:64.

In one embodiment, the antibody of the invention comprises a heavy chain comprising the amino acid sequence of SEQ ID NO:32 and SEQ ID NO:63. In one embodiment, the antibody of the invention comprises a light chain comprising the amino acid sequence of SEQ ID NO:37 and SEQ ID NO:64. In another embodiment, the antibody of the invention comprises a heavy chain comprising the amino acid sequences of SEQ ID NO:32 and SEQ ID NO:63 and a light chain comprising the amino acid sequences of SEQ ID NO:37 and SEQ ID NO:64.

In one embodiment, the antibody of the invention is an antibody that binds to properdin and competes with the binding of at least one of the anti-properdin antibodies described herein. In another embodiment, the antibody of the invention is an antibody that binds to properdin and competes with the binding of the antibody designated mAb 19.1 to properdin. In another embodiment, the antibody of the invention is an antibody that binds to properdin and competes with the binding of the antibody designated mAb 25 to properdin. In another embodiment, the antibody of the invention is an antibody that binds to properdin and competes with the binding of the antibody designated mAb 22.1 to properdin. In another embodiment, the antibody of the invention is an antibody that binds to properdin and competes with the binding of the antibody designated mAb 30 to properdin.

In another embodiment, the invention is a method of treating an alternative pathway (AP)-mediated pathology in an individual, comprising the step of administering to said individual at least one of the anti-properdin antibodies described herein. In various embodiments, the alternative pathway (AP)-mediated pathology is at least selected from the group consisting of: macular degeneration, ischemia reperfusion injury, arthritis, rheumatoid arthritis, paroxysmal nocturnal hemoglobinuria (PNH) syndrome, atypical hemolytic uremic (aHUS) syndrome, asthma, organ transplantation sepsis, inflammation, glomerulonephritis, lupus, and combinations thereof. In some embodiments, the anti-properdin antibody selectively inhibits the alternative pathway, but does not inhibit the classical pathway and the lectin pathway. In some embodiments, the anti-properdin antibody does not affect the AP amplification loop of the classical pathway and the lectin pathway. In some embodiments, the anti-properdin antibody inhibits the generation of a C3bBb protein.

In one embodiment, the invention is a transgenic mouse that expresses human properdin (e.g., SEQ ID NO:67; SEQ ID NO:54), but does not express murine properdin.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings. In the drawings:

FIG. 5, comprising FIGS. 5A-5C, depicts the results of epitope mapping for mAb 19.1 and 25 and generation of deletion mutants of human properdin (fP). FIG. 5a so depicts the deduced amino acid sequence of human properdin (SEQ ID NO:54). The signal peptide is underlined. The mature protein starts at residue 28. FIG. 5b depicts the amino acid sequences of the 7 thrombospondin repeat (TSR) domains of human properdin. They are as follows: TSR0 (SEQ ID NO:55), TSR1 (SEQ ID NO:56), TSR2 (SEQ ID NO:57), TSR3 (SEQ ID NO:58), TSR4 (SEQ ID NO:59), TSR5 (SEQ ID NO:60), TSR6 (SEQ ID NO:61). FIG. 5c depicts the results of epitope mapping for mAb 19.1 and 25 and generation of deletion mutants of human properdin (fP). Human properdin (fP) is composed of 7 thrombospondin repeat (TSR) domains which are numbered 0 to 6. Individual TSR domains (and in some instances two TSR domains) have been deleted and the mutant proteins were expressed in Chinese hamster ovary (CHO) cells. All TSR deletion mutants are expressed at the expected sizes except TSR5 deletion mutant which is substantially smaller than the expected size. It is likely that TSR5 deletion mutant was subjected to proteolysis. The size of TSR5 deletion is similar to that of TSR5+6 deletion mutant, suggesting that TSR6 may have been proteolytically removed in the TSR5 deletion mutant. CHO cell lysates were analyzed by Western blot using a polyclonal goat anti-human fP antibody. M: molecular weight (MW) marker.

FIG. 8, comprising In FIG. 8A, the data indicate the epitope mapped to the C-terminal quarter segment of TSR6 with the amino acid sequence: LVVEEKRPCLHVPACKDPEEEEL (SEQ ID NO:53). Because TSR0-5 (i.e., dTSR6) lost binding to mAb 25, it was concluded that TSR6 constitutes at least part of the epitope of mAb 25. Additional mutants of TSR6 were generated as follows: TSR0-5+¼ TSR6, TSR0-5+½ TSR6 and TSR0-5+¾ TSR6. Mutant, but not intact, properdin proteins contained a 6×His tag at their C-terminus. As shown by western blot with anti-human fP and anti-His tag antibodies, all three mutants were successfully expressed. ELISA binding experiments showed that all three mutants lost binding to mAb 25. As a positive control, all mutant proteins reacted with mAb 19.1. This result suggests that the last quarter segment of TSR6 (with the sequence designated by SEQ ID NO:53) constitutes a key part of the epitope of mAb 25. HuP refers to full-length (intact) human fP transfected CHO cells as a positive control; ConLysate refers to untransfected CHO cells as negative controls for binding. In FIG. 8B the data indicate that the epitope of mAb 25 is dependent on two cysteine residues in TSR6 (SEQ ID NO: 61, shown in FIG. 5B). These are cysteine 62 (C62) and cysteine 78 (C78) of TSR6. Single mutation to Alanine (A) of either C62 or C78 in full-length human properdin did not abolish mAb 25 binding, but double mutations of C62A and C78A abolished mAb 25 binding. As a positive control for mutant protein expression, mAb 19.1 showed reactivity to all samples. This result suggests that C78 within the last quarter segment of TSR6 (with the sequence designated by SEQ ID NO: 53), as well as C62 which is located outside SEQ ID NO:53 but within TSR6 (SEQ ID: 61), constitute two critical residues of the epitope of mAb 25. Binding assays of mAbs 19.1 and 25 was performed on ELISA plates so using homogenates of transfected CHO cells. HuP refers to full-length (intact) human fP transfected CHO cells as a positive control; Con refers to untransfected CHO cells as negative controls for binding. The other samples are CHO cells transfected with mutant human fP cDNA containing single or double C62A and C78A mutations.

FIG. 9 depicts the nucleotide and amino acid sequence of the variable region sequences of heavy (SEQ ID NO:1; SEQ ID NO:2) and light (SEQ ID NO:6; SEQ ID NO:7) chains of mAb 19.1, including the CDRs (VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; VL-CDR3: SEQ ID NO:10).

Figure 10:
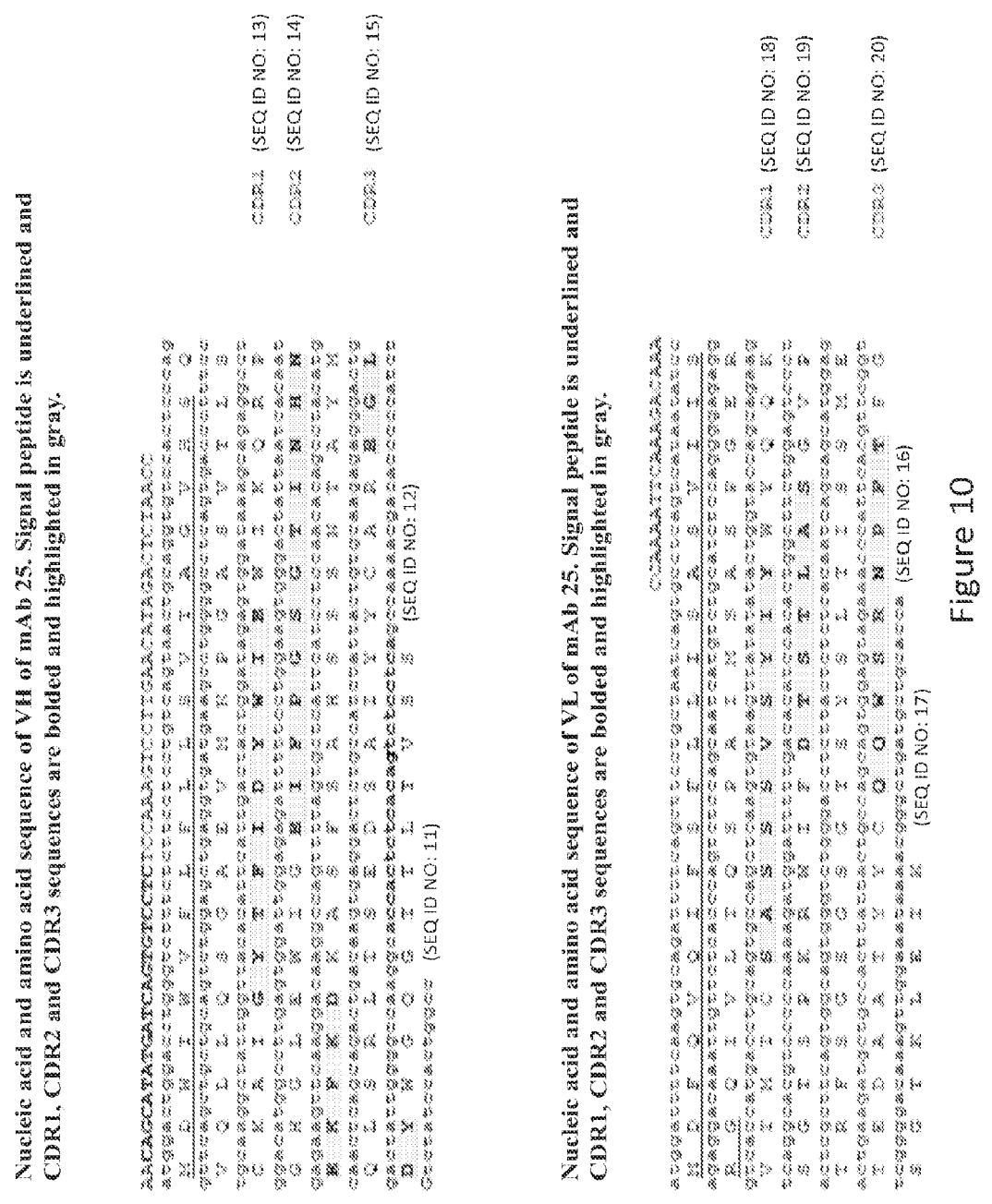

FIG. 10 depicts the nucleotide and amino acid sequence of the variable region sequences of heavy (SEQ ID NO:11; SEQ ID NO:12) and light (SEQ ID NO:16; SEQ ID NO:17) chains of mAb 25, including the CDRs (VH-CDR1: SEQ ID NO:13; VH-CDR2: SEQ ID NO: 14; VH-CDR3: SEQ ID NO: 15; VL-CDR1: SEQ ID NO: 18; VL-CDR2: SEQ ID NO:19; VL-CDR3: SEQ ID NO:20).

Figure 11:
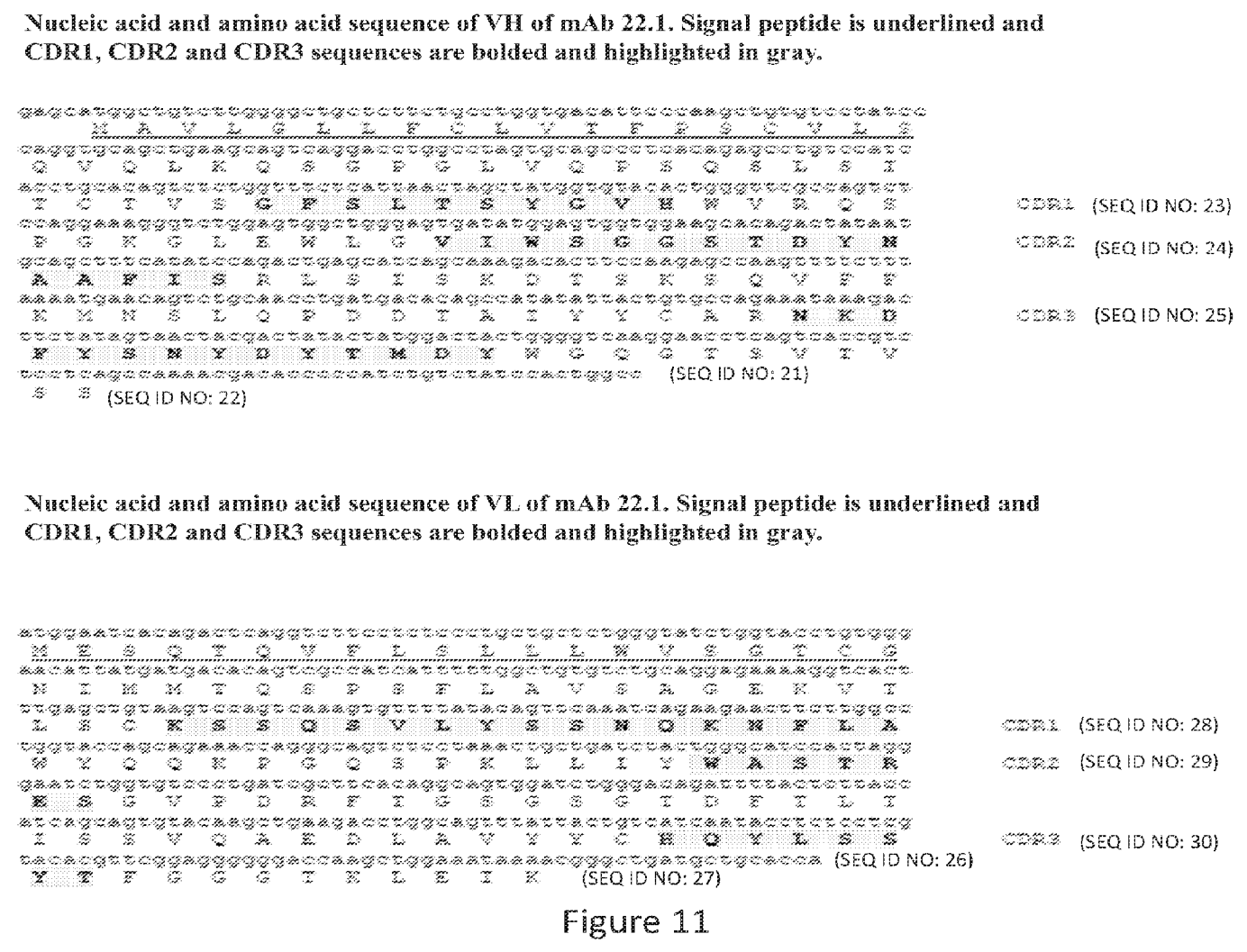

FIG. 11 depicts the nucleotide and amino acid sequence of the variable region sequences of heavy (SEQ ID NO:21; SEQ ID NO:22) and light (SEQ ID NO:26; SEQ ID NO:27) chains of mAb 22.1, including the CDRs (VH-CDR1: SEQ ID NO:23; VH-CDR2: SEQ ID NO:24; VH-CDR3: SEQ ID NO:25; VL-CDR1: SEQ ID NO:28; VL-CDR2: SEQ ID NO:29; VL-CDR3: SEQ ID NO:30).

Figure 12:
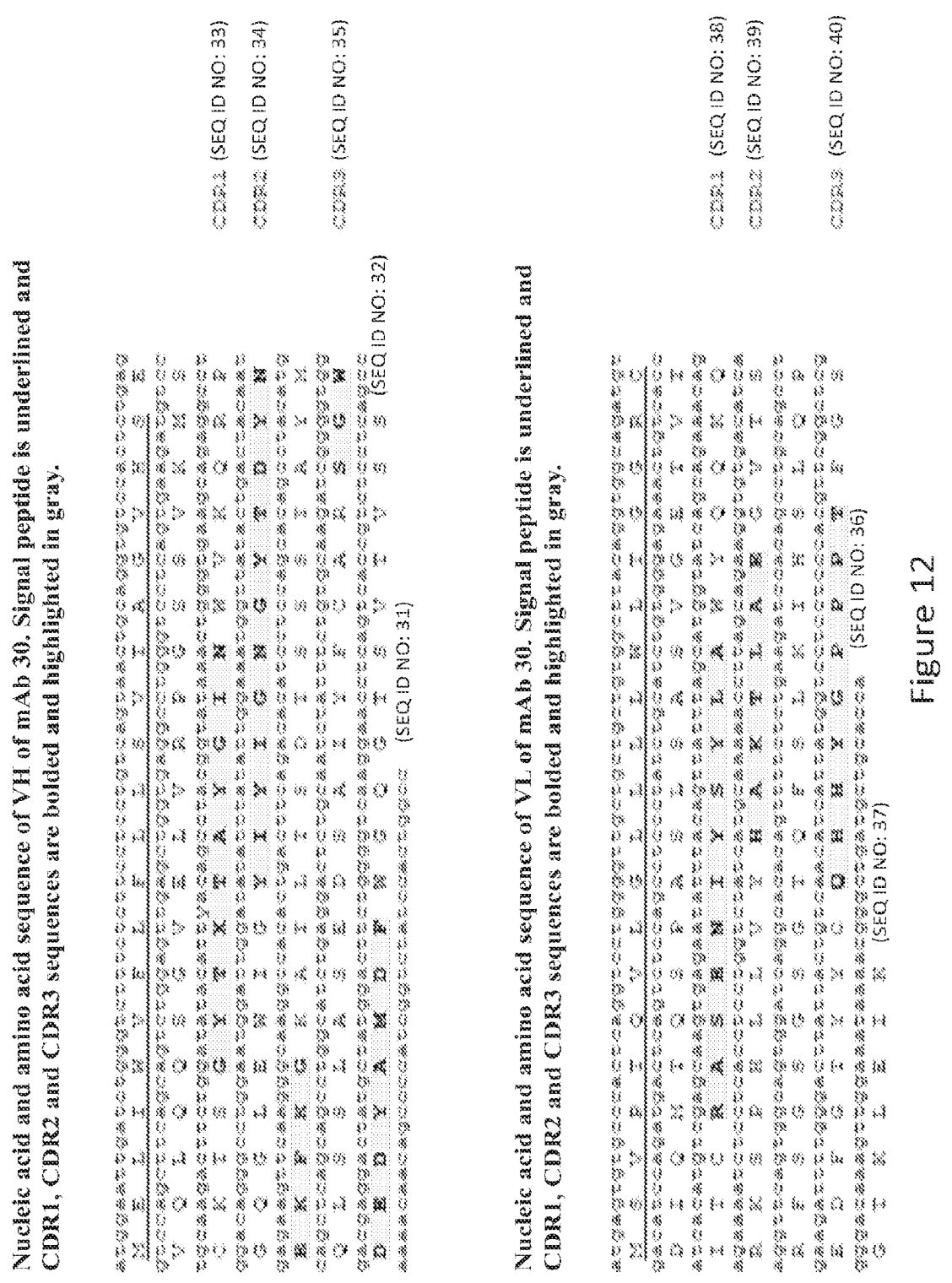

FIG. 12 depicts the nucleotide and amino acid sequence of the variable region sequences of heavy (SEQ ID NO:31; SEQ ID NO:32) and light (SEQ ID NO:36; SEQ ID NO:37) chains of mAb 30, including the CDRs (VH-CDR1: SEQ ID NO:33; VH-CDR2: SEQ ID NO:34; VH-CDR3: SEQ ID NO:35; VL-CDR1: SEQ ID NO:38; VL-CDR2: SEQ ID NO:39; VL-CDR3: SEQ ID NO:40).

Figure 13:
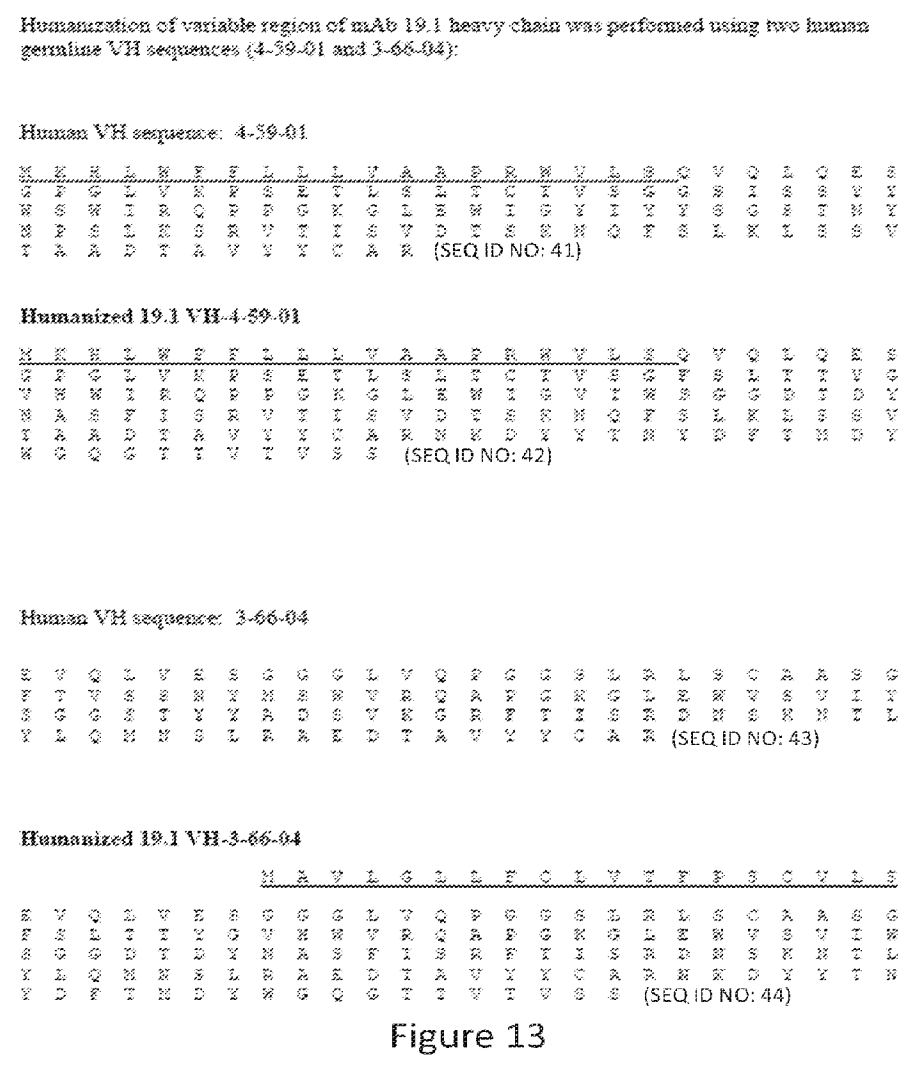

FIG. 13 depicts the humanized amino acid sequence of the variable region of the heavy chain of mAb 19.1 (humanized 19.1 VH-4-59-01 (SEQ ID NO:42); humanized 19.1 VH-3-66-04 (SEQ ID NO:44)) after CDR grafting using two human germline VH sequences (human VH 4-59-01 (SEQ ID NO:41); human VH 3-66-04 (SEQ ID NO:43)).

Figure 14:
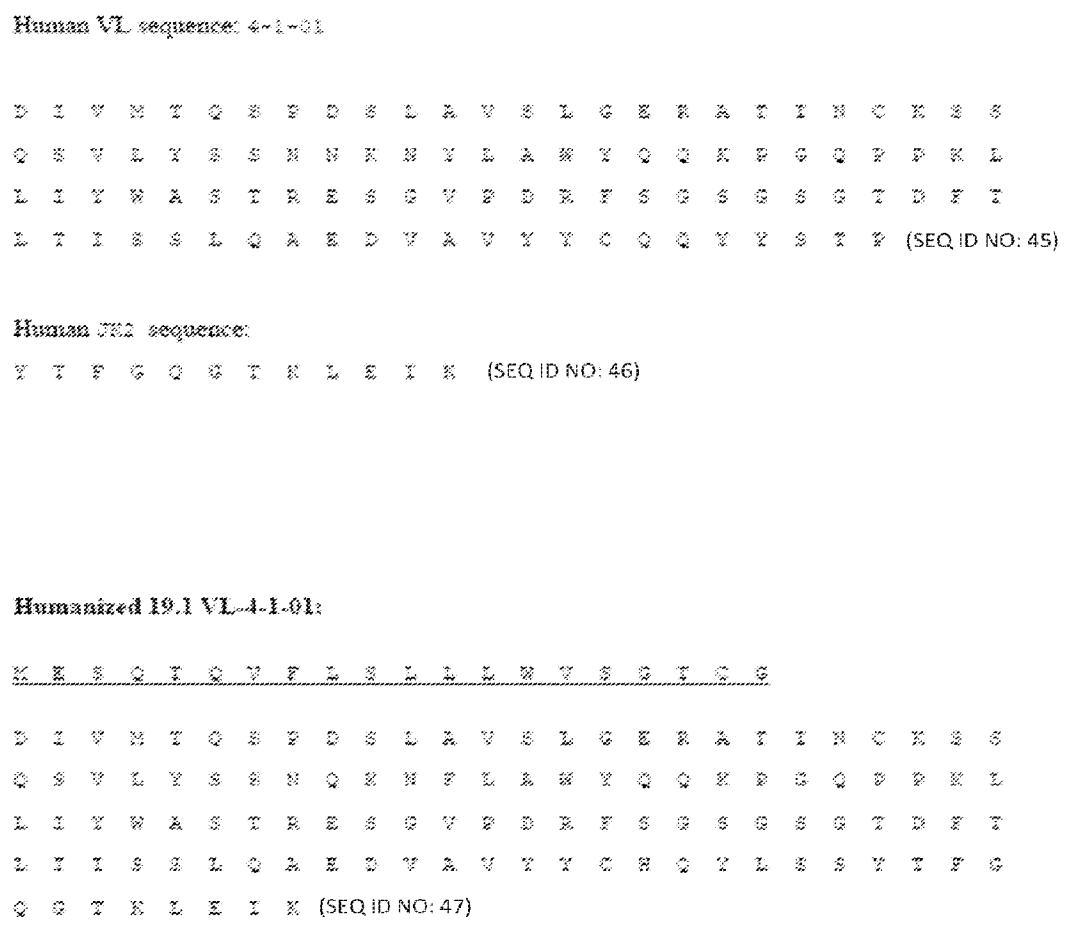

FIG. 14 depicts the humanized amino acid sequence of the variable region of the light chain of mAb 19.1 (humanized 19.1 VL-4-1-01 (SEQ ID NO:47)) after CDR grafting using a human germline VL sequence (human VL 4-1-01 (SEQ ID NO:45); human JK2 (SEQ ID NO:46)).

Figure 15:
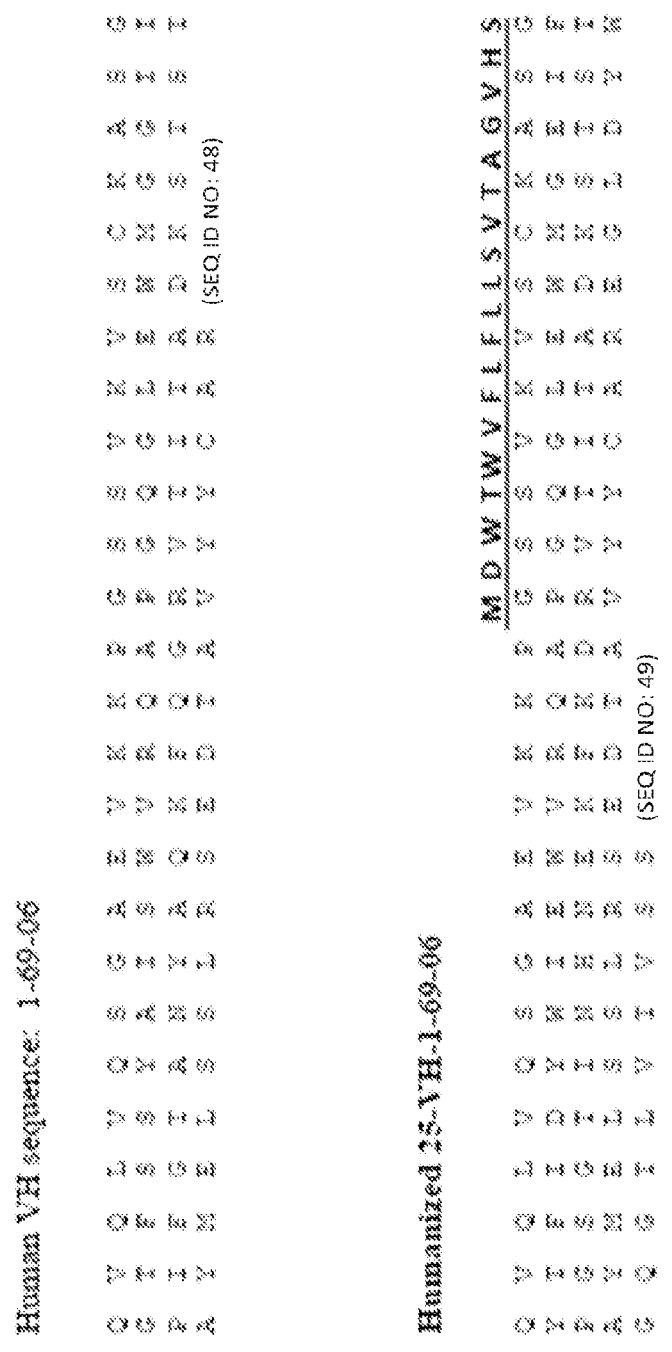

FIG. 15 depicts the humanized amino acid sequence of the variable region of so the heavy chain of mAb 25 (humanized 25-VH-1-69-06 (SEQ ID NO:49)) after CDR grafting using a human germline VH sequence (human VH 1-69-06 (SEQ ID NO:48)).

FIG. 16 depicts the humanized amino acid sequence of the variable region of the light chain of mAb 25 (humanized 25-VL-1-69-06 (SEQ ID NO:51)) after CDR grafting using a human germline VL sequence (human VL 1-69-06 (SEQ ID NO:50)); human Jk3 (SEQ ID NO:62).

FIG. 17, comprising FIGS. 17A and 17B, depicts the results of experiments assessing recombinant chimeric and humanized 19.1 mAbs. FIG. 17A depicts the amino acid sequences of human IgG4 constant heavy region, with Serine 229 to Proline mutation (SEQ ID NO:63), and human kappa constant light region (SEQ ID NO:64). These sequences were used to construct chimeric (mouse variable region+human constant region) and humanized (humanized mouse variable region+human constant region) anti-properdin antibodies. FIG. 17B depicts the results of experiments assessing the expression of recombinant chimeric and humanized 19.1 mAbs. SDS PAGE analysis of recombinant chimeric 19.1 mAb and two humanized 19.1 mAbs. Construction of the chimeric 19.1 heavy chain was achieved by joining the VH region of 19.1 with the constant region of human IgG4 heavy chain. Construction of the chimeric 19.1 light chain was achieved by joining the VL region of 19.1 with the constant region of the human kappa chain. Humanized 19.1 heavy and light chains were constructed in the same way, i.e. humanized VH region was joined with the constant region of human IgG4 heavy chain and humanized light chain was joined with the constant region of human kappa chain. CHO cells were co-transfected with heavy and light chain cDNAs and stable lines established by drug section. For the two humanized mAbs, each of the two humanized heavy chains was paired with the same humanized light chain for transfection. Expressed mAbs were purified from CHO cell culture medium by protein G affinity column.

Biacore analysis was performed on a Biacore-2000 instrument. The chip was regenerated between each binding using 50 mM NaOH.

Figure 19:
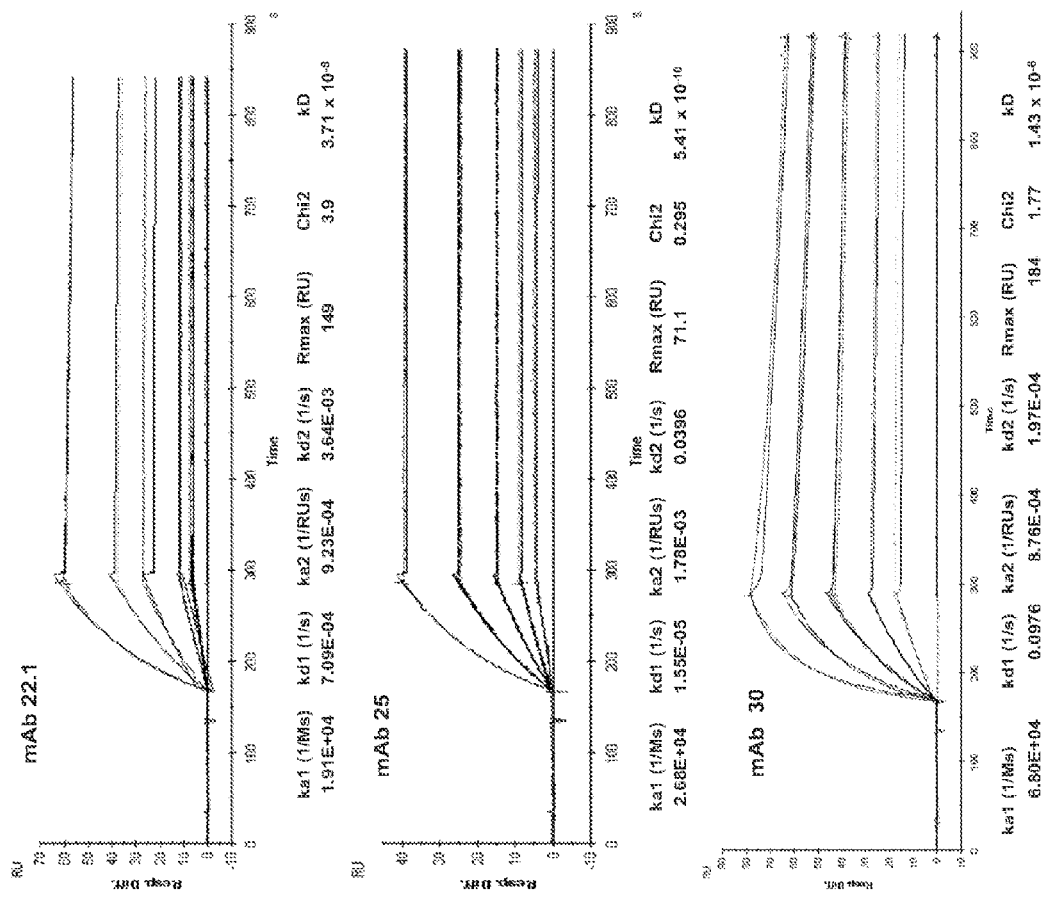

FIG. 19 depicts the results of experiments measuring the antigen binding affinities of mAb 25, 22.1 and 30 as determined by Biacore analysis. Purified human fP was coupled onto CM4 chip using the amine coupling method. Biacore analysis was performed on a Biacore-2000 instrument. The chip was regenerated between each binding using 50 mM NaOH.

Figure 20:
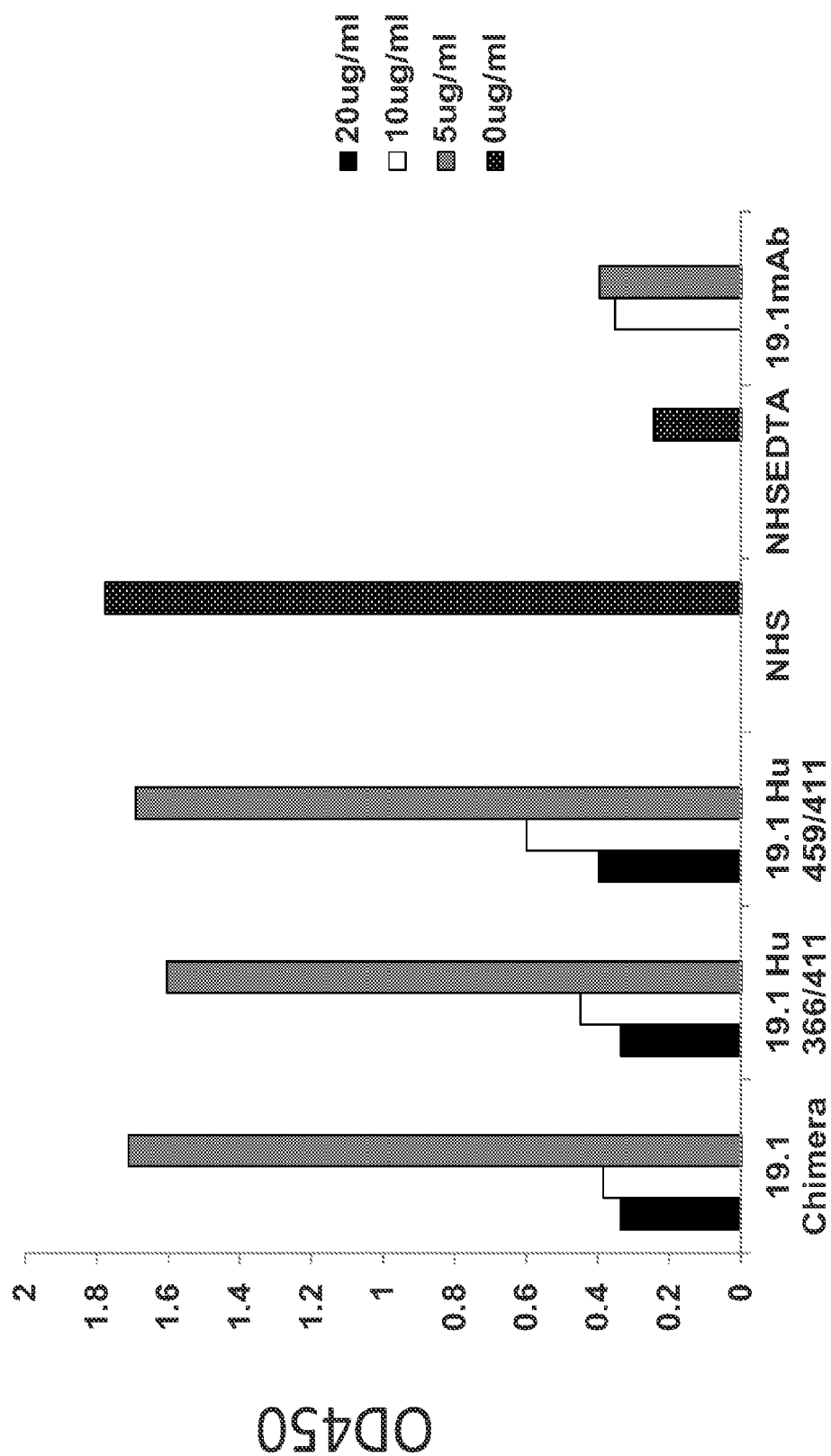

FIG. 20 depicts the results of experiments assessing the relative activities of 19.1, chimeric 19.1 and humanized 19.1 mAbs in blocking LPS-induced human AP complement activation. ELISA plates were coated with LPS overnight, and 50% normal human serum (NHS) diluted in GVB-Mg++-EGTA was added and incubated at 37° C. for 1 hr before detection of C3 deposition using anti-C3 antibodies. NHS with no antibody added served as a positive control (NHS) and NHS with EDTA added served as a negative control (NHSEDTA). For 19.1 mAb, concentrations of 5 µg/ml and 10 µg/ml were sufficient to inhibit complement activation. For the chimeric and the two humanized 19.1 mAbs, a concentration of 5 µg/ml was not sufficient to inhibit complement activation. However, concentrations of 10 µg/ml and 20 µg/ml were effective at blocking AP complement activation.

Figure 21:
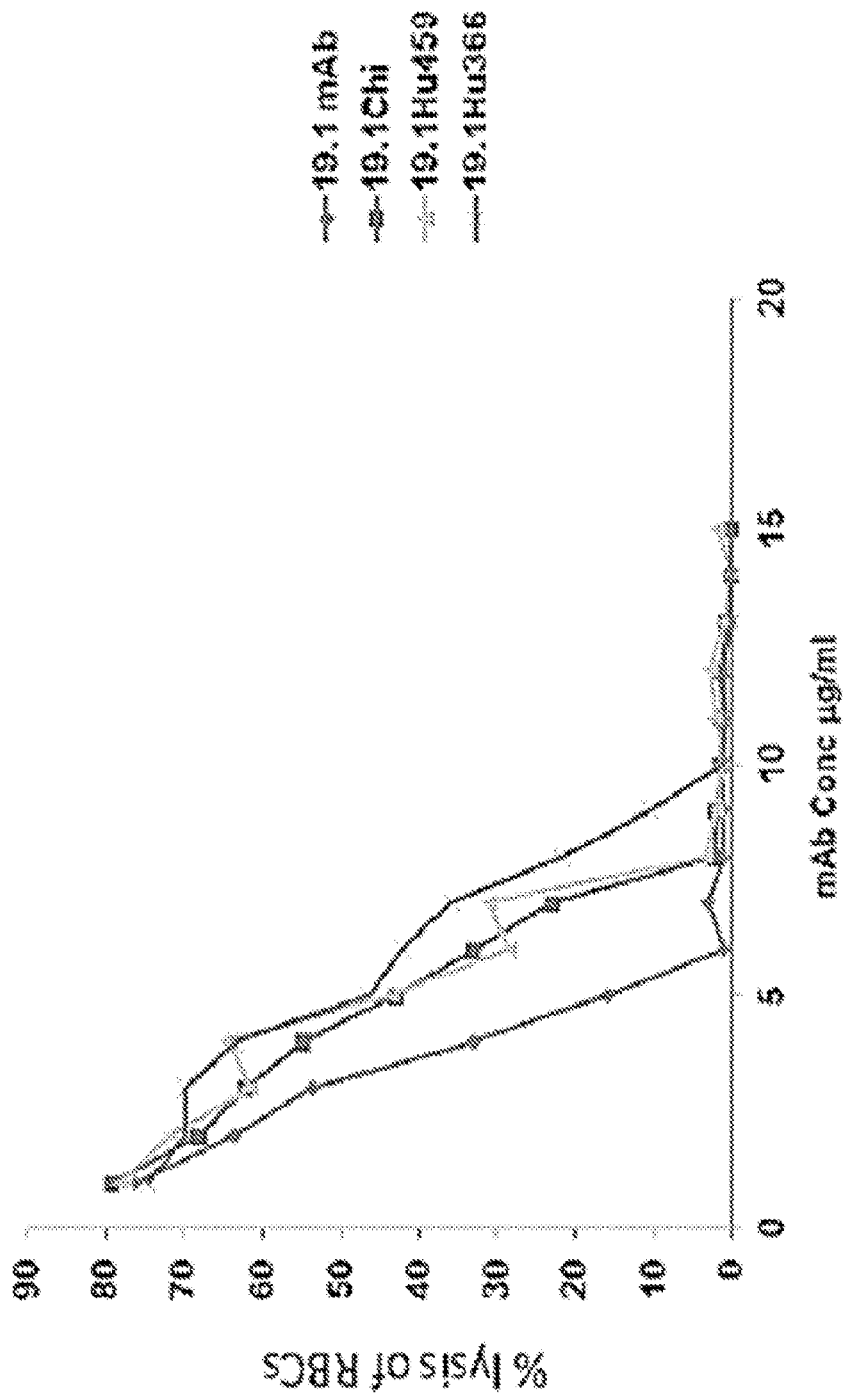

FIG. 21 depicts the results of experiments assessing relative activities of 19.1, chimeric 19.1 and humanized 19.1 mAbs in blocking human RBC lysis by human AP complement in the context of fH and DAF dysfunction. Human RBCs were incubated with 50% normal human serum in the presence of fH-9-20 (30 µM) and anti-DAF antibody (7.5 µg/ml). Human serum was diluted in GVB-Mg++-EGTA and the incubation was carried out at 37° C. for 1 hr. Before being added to the RBCs, the human serum was pre-incubated with increasing concentrations of 19.1, chimeric 19.1 and humanized 19.1 mAbs (1-15 µg/ml) at 4° C. for 1 hr. There was a dose-dependent inhibition of RBC lysis by all 4 nmAbs. However, the EC50 for the chimeric and humanized 19.1 mAbs were higher than that of 19.1 mAb. This result was consistent with the data shown in FIG. 20.

Figure 22:
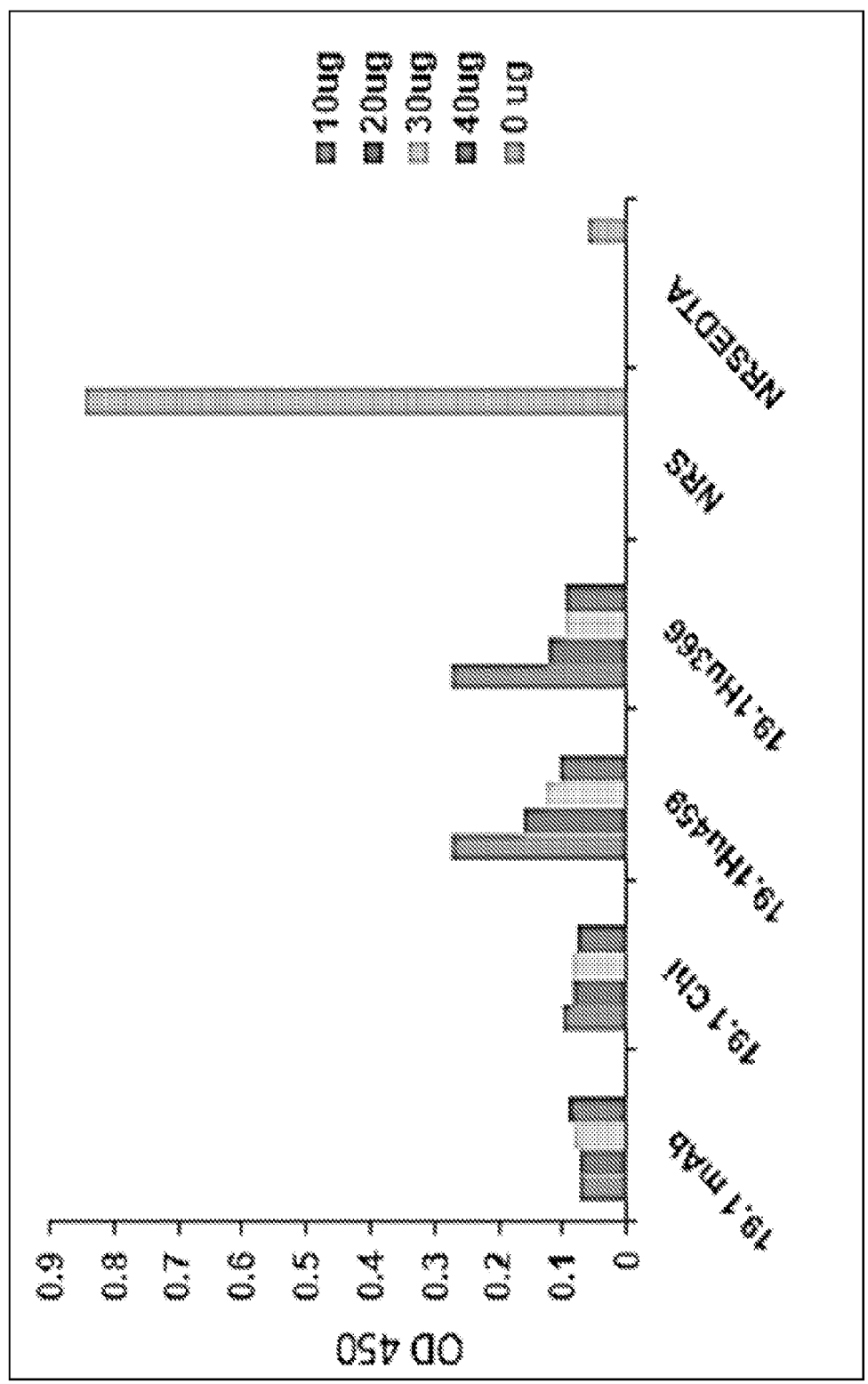

FIG. 22 depicts the results of experiments assessing the relative activities of 19.1, chimeric 19.1 and humanized 19.1 mAbs in blocking LPS-induced Rhesus monkey AP complement activation. ELISA plates were coated with LPS overnight, and 50% normal Rhesus monkey serum (NRS) diluted in GVB-Mg++-EGTA was added and incubated at 37° C. for 1 hr before detection of C3 deposition using anti-human C3 antibodies. NRS with no antibody added served as a positive control (NRS) and NRS with EDTA added served as a negative control (NRSEDTA). For 19.1 and chimeric 19.1 mAbs, concentrations of 10-40 µg/ml were sufficient to inhibit Rhesus monkey complement activation. For the two humanized 19.1 mAbs, concentrations of 30 or 40 µg/ml were effective to inhibit complement activation. Concentrations of 10 or 20 µg/ml also substantially inhibited Rhesus monkey AP complement activation.

Figure 23:
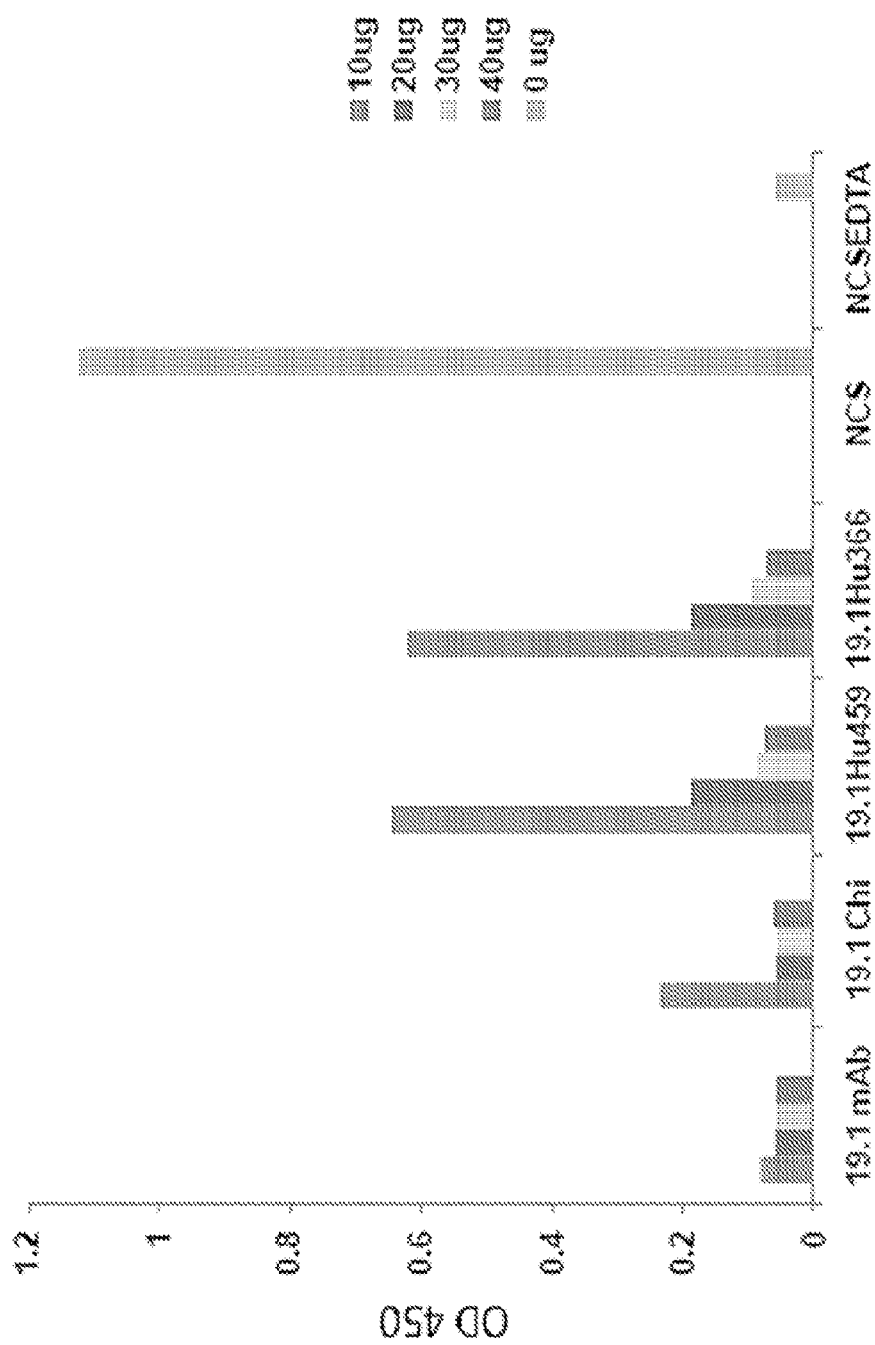

FIG. 23 depicts the results of experiments assessing the relative activities of 19.1, chimeric 19.1 and humanized 19.1 mAbs in blocking LPS-induced Cynomolgus monkey AP complement activation. ELISA plates were coated with LPS overnight, and 50% normal Cynomolgus monkey serum (NCS) diluted in GVB-Mg++-EGTA was added and incubated at 37° C. for 1 hr before detection of C3 deposition using anti-human C3 antibodies. NCS with no antibody added served as a positive control (NCS) and NCS with EDTA added served as a negative control (NCSEDTA). For the 19.1 mAb, concentrations of 10-40 µg/ml were sufficient to inhibit Cynomolgus monkey AP complement activation. For the chimeric 19.1 mAb, concentrations 20-40 µg/ml were sufficient to inhibit Cynomolgus monkey AP complement activation but a concentration of 10 µg/ml also significantly inhibited complement activation. For the two humanized 19.1 mAbs, concentrations of 30 or 40 µg/ml were effective to inhibit Cynomolgus complement activation. However, a concentration of 20 µg/ml also substantially inhibited Cynomolgus monkey AP complement activation. A concentration of 10 µg/ml also partially inhibited Cynomolgus AP complement activity.

Figure 24:
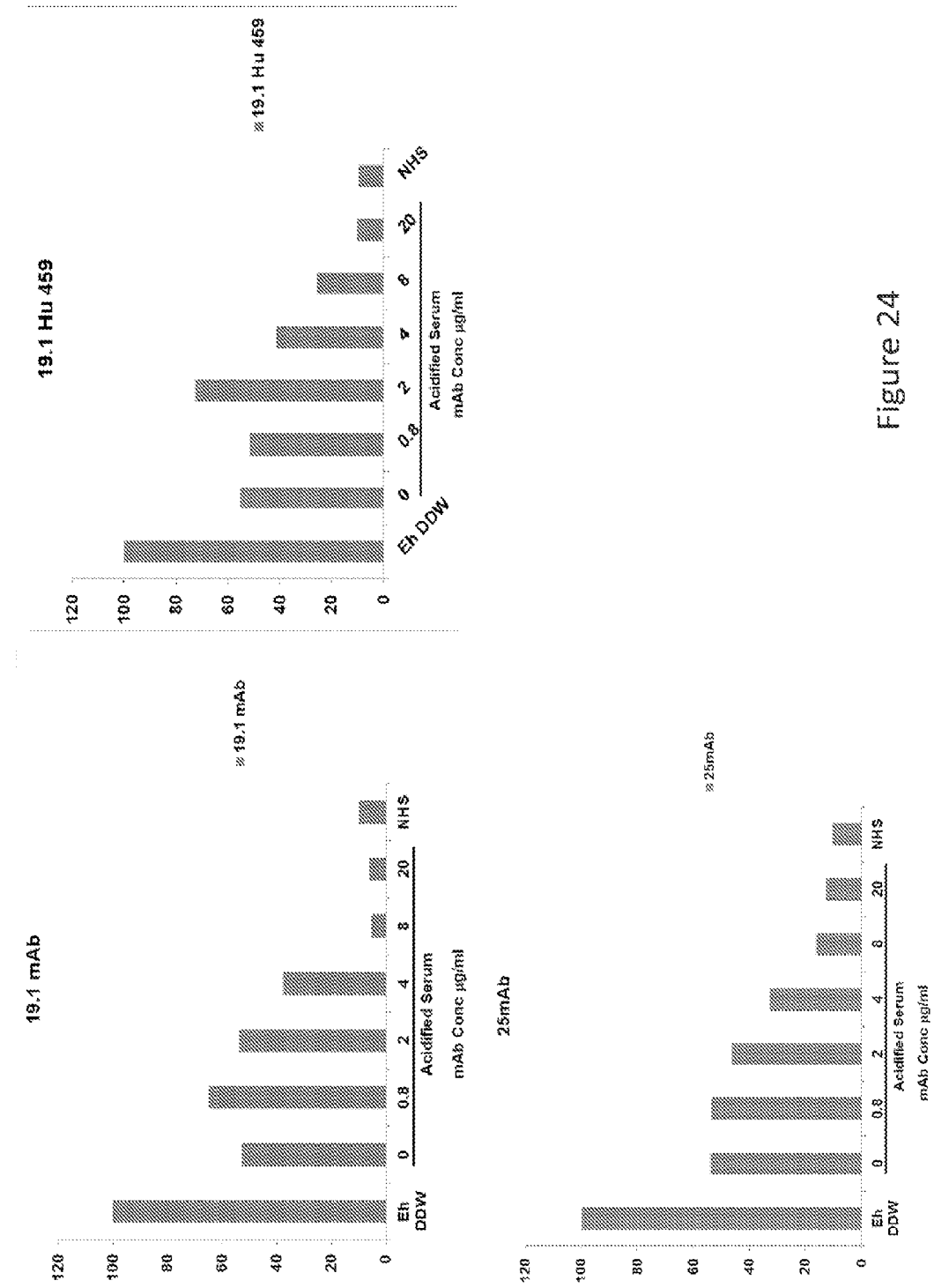

FIG. 24 depicts the results of experiments assessing the inhibition of acidified serum lysis of PNH patient red blood cells (Ham's test) by mAb 19.1, 25 and humanized 19. RBCs from paroxysmal nocturnal hemoglobinuria (PNH) patients were subjected to Ham's acidified serum test in the presence or absence of mAbs. RBCs were incubated with autologous serum (final concentration 83%) at 37 C for 2 hrs and percent lysis was calculated by measuring the OD405 of the supernatant, normalized to a sample of RBCs completely lysed by distilled water (Eh DDW). The incubation mixture was composed of the following: 240 µl of serum, 25 µl of ⅙ NHCL (or 25 µl saline for negative controls), 12.5 µl of 50% (v/v) RBC suspension, 10 µl mAb in saline. A sample of RBCs incubated with nonacidified autologous serum (NHS) was used as a negative control (background lysis). In the absence of mAbs, about 50% of RBCs were lysed by acidified serum. This lysis was completely inhibited by mAb 19.1 at 8 µg/ml and above concentration, by a humanized 19.1 mAb (#459) at the concentration of 20 µg/ml and by mAb 25 at the concentration of 8 µg/ml so and above.

Figure 25:
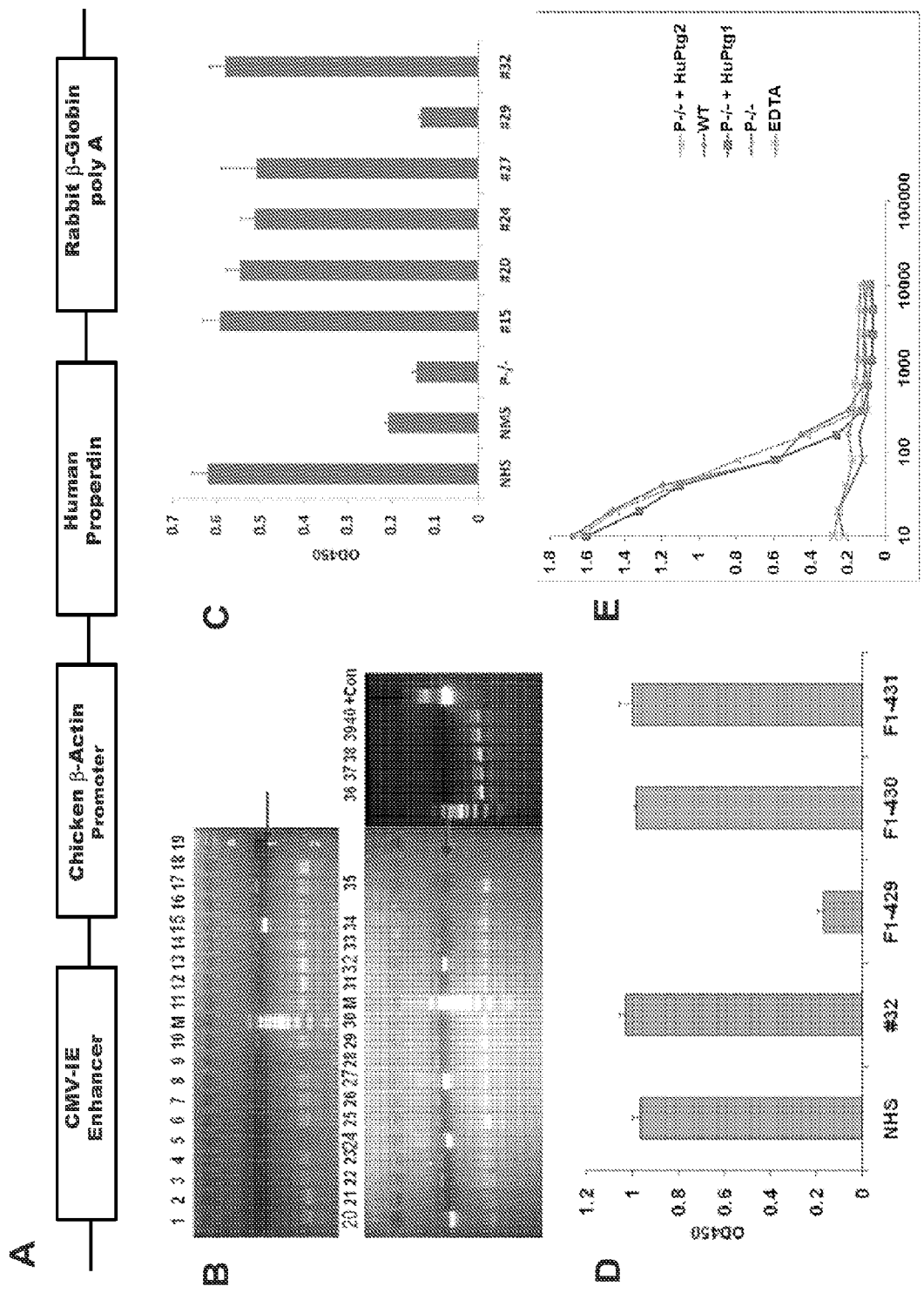

FIG. 25, comprising FIGS. 25A-25E, depicts the generation of a properdin humanized mouse. A human fP expression vector was constructed as illustrated in the schematic in FIG. 25A, using the chicken β-actin promoter with CVM-IE enhancer and the rabbit β-globin polyA tail for stable expression of the cDNA in eukaryotic cells. This plasmid was linearized and microinjected into the zygotes of C57BL/6 mice to produce human fP transgenic founder mice. By PCR screening (using primers specific to human fP 5'ATCAGAGGCCTGTGACACC-3' (SEQ ID NO:65) and 5'-CTG CCCTTGTAGCTCCTCA-3' (SEQ ID NO:66)), positive founder mice (showing a human fP cDNA fragment of about 800 bp) were identified. Of 40 mice analyzed, five (#15, 20, 24, 27 and 32) were positive (FIG. 25B, red arrows). ELISA assays were performed to detect human fP in the transgenic positive mice (FIG. 25C). Plate was coated with a non-blocking mAb against human fP (clone 8.1). After incubation with diluted serum (10%), human fP was detected by ELISA using an HRP-conjugated goat-antihuman fP antibody. Normal human serum (NHS) was used as a positive control. As can be seen, human fP was detected in NHS and in the sera of the 5 transgenic mice but not in normal (i.e. non-transgenic) mouse serum (NMS), transgenic-negative (#29) or in fP$^{-/-}$ mouse serum. Founder mouse #32 was bred with WT mice and pups were screened by PCR as described above. Three representative F1 mice, one PCR-negative (F1-429) and two PCR-positive (F1-430 and F1-431), were tested by ELISA for the presence of human fP in their sera (FIG. 25D). As shown, human fP was detected in the two PCR-positive mice but not in the PCR-negative mouse. Sera from NHS and the founder parent (#32) were used as positive controls. This result suggested that the transgene is stable and can be transmitted through germline. Founder mouse #32 was then bred with fP$^{-/-}$ mice to generate fP$^{-/-}$-human fP transgene+ mice.

LPS-induced AP complement activation assay showed that fP$^{-/-}$-human fP transgene+ mice, but not fP$^{-/-}$ mice, had serum AP complement activity indistinguishable from that of WT mice (FIG. 25E), suggesting that transgenically expressed human fP was able to rescue the phenotype of fP$^{-/-}$ mice. WT serum treated with EDTA was used as a negative control. This result confirmed that a properdin humanized mouse line was generated.

Figure 26:
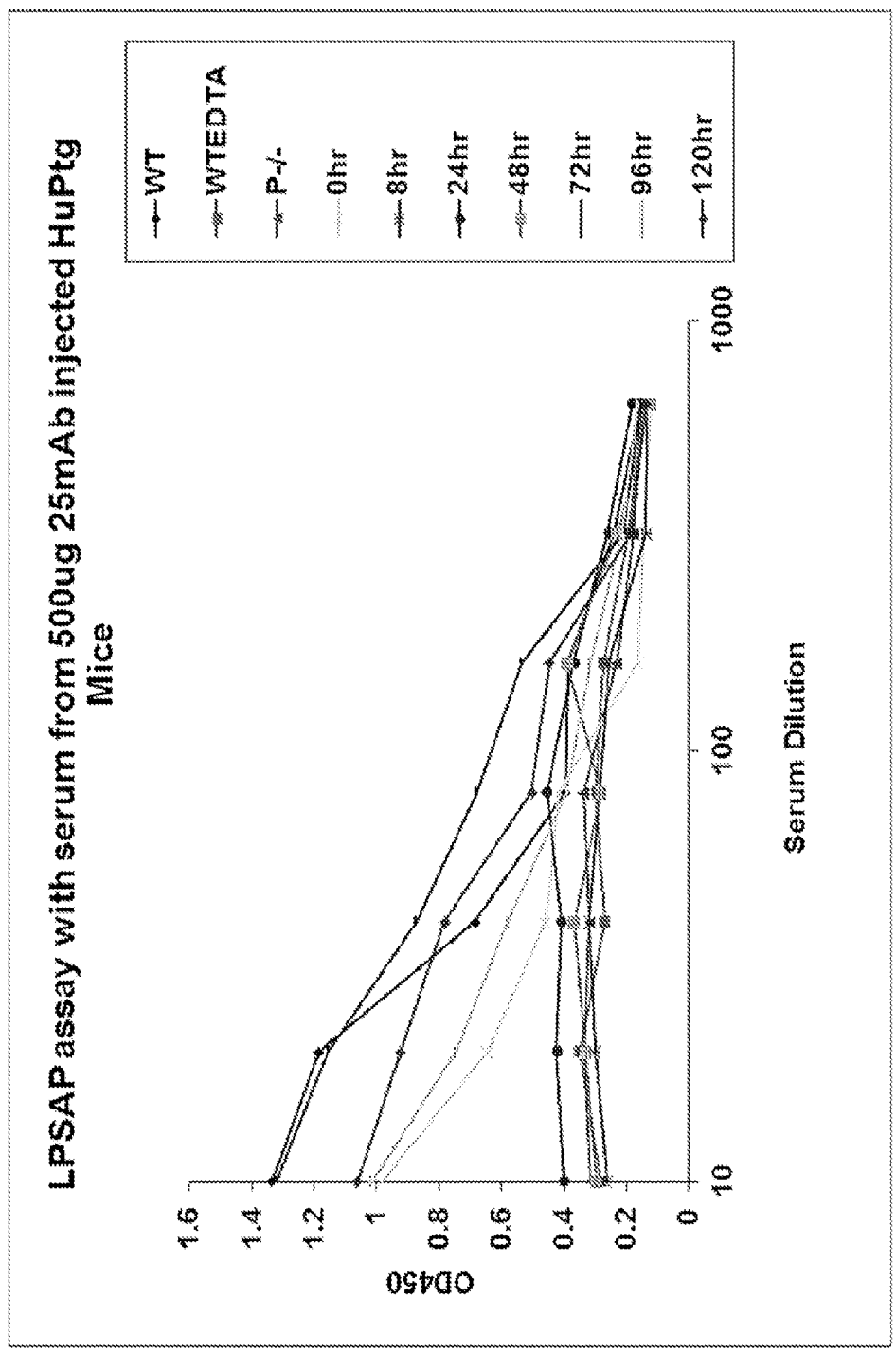

FIG. 26 depicts experiments examining the in vivo activity and kinetics of mAb 25 in "properdin humanized" mice. A properdin humanized mouse (fP$^{-/-}$-human fP transgene+) was injected with 0.5 mg (i.p.) of mAb 25. Serum samples were collected before injection (0 hr) and then at various time points after injection and tested for LPS-induced AP complement activation. As shown, no AP complement activity was present in fP$^{-/-}$ mouse serum or in WT serum treated with EDTA. In contrast, AP complement activity was detected in WT serum and in the serum of fP humanized mouse at time 0 hr (before mAb treatment). AP complement activity in the humanized mouse remained undetectable at 8, 24 and 48 hrs after mAb treatment but became detectable at 72, 96 and 120 hrs. These results suggest that at a dosage of 0.5 mg/mouse, mAb 25 was able to inhibit AP complement activity in vivo for 48 hrs.

Figure 27:
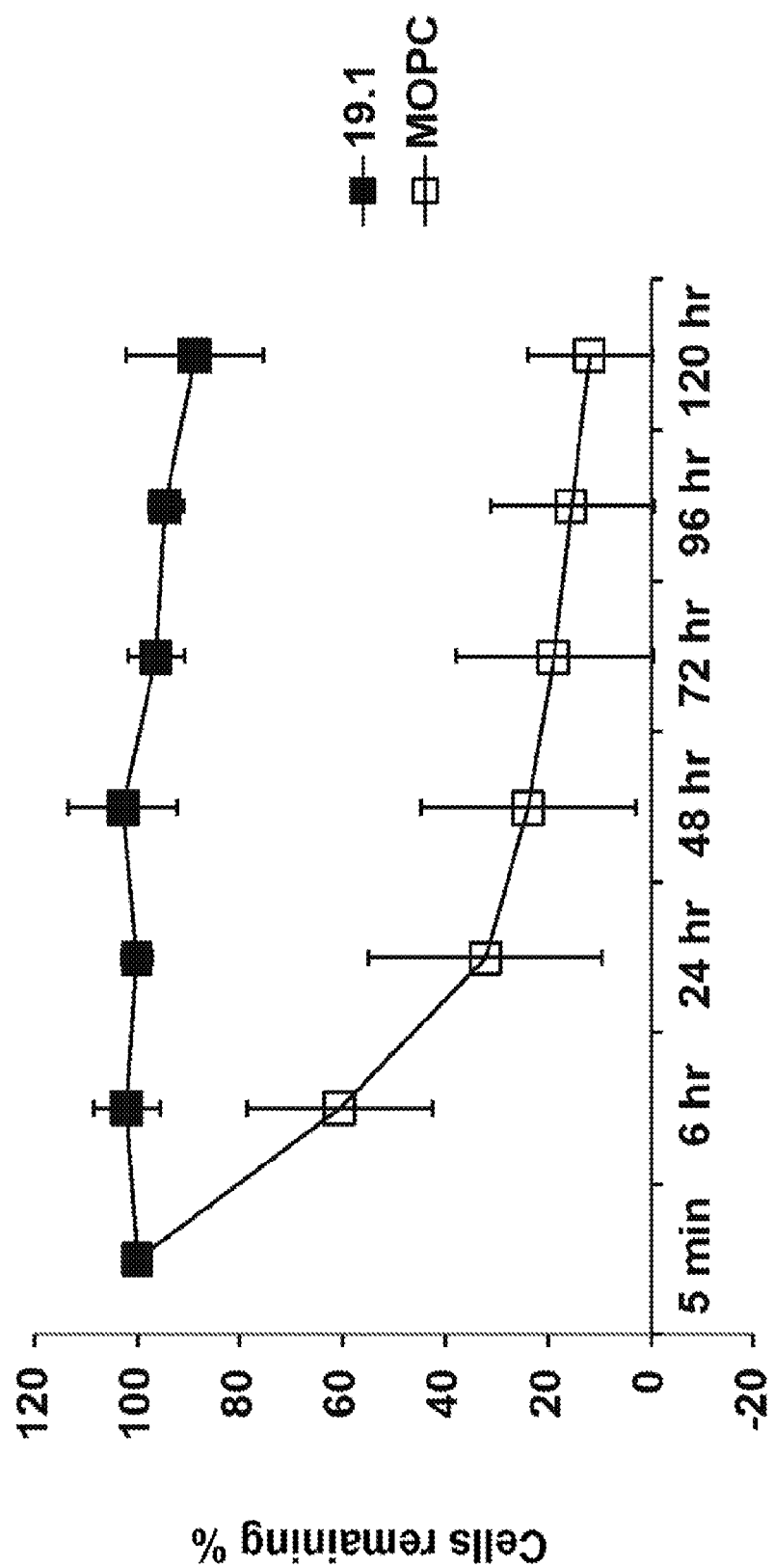

FIG. 27 depicts the results of an experiment demonstrating that anti-human properdin mAb 19.1 prevents extravascular hemolysis (EVH). In this EVH model, properdin humanized mice (n=4 per experimental group) were transfused with red blood cells (RBC) from Crry/DAF/C3 triple knockout (TKO) mice. Recipient mice (properdin humanized mice) were treated 6 hrs before RBC transfer with mAb 19.1 (2 mg/mouse, i.p.) or a control mouse IgG1 mAb (MOPC, purified from MoPC 31C hybridoma, from ACTT). RBCs were harvested from donor TKO mice, washed in PBS and labeled with CFSE before injection (through tail vein) into recipient mice, according to previously published procedure (Miwa et al., 2002, Blood 99: 3707-3716). Each recipient mouse received RBCs equivalent to 100 µl of blood. At 5 minutes and 6, 24, 48, 72, 96, 120 hours after RBC transfusion, recipient mice were bled and RBCs were analyzed to determine the number of CFSE-labeled (i.e. transfused) RBCs remaining in the circulation. Number of CFSE-labeled RBCs in each recipient was normalized (as %) to that detected at the 5 min time point. In control IgG (MOPC)-treated recipient mice, TKO RBCs were rapidly eliminated through EVH, consistent with previous findings (Miwa et al., 2002, Blood 99: 3707-3716). However, in recipient mice treated with anti-human properdin 19.1 mAb, no EVH occurred and the transfused RBCs persisted, demonstrating that anti-properdin mAb was effective in preventing EVH.

FIG. 28 depicts the nucleic acid sequence of human properdin cDNA (SEQ ID NO:67) used for generating human properdin transgenic mice.

DETAILED DESCRIPTION OF THE INVENTION

This invention relates to the inhibition of the alternative pathway (AP) of complement using an anti-properdin antibody. In various embodiments, the invention is directed to compositions and methods for treating an AP-mediated pathology or AP-mediated condition in an individual by contacting the individual with an anti-properdin antibody. The AP-mediated pathologies and conditions that can be treated with the compositions and methods of the invention include, but are not limited to, macular degeneration, ischemia reperfusion injury, arthritis, rheumatoid arthritis, asthma, paroxysmal nocturnal hemoglobinuria (PNH) syndrome, atypical hemolytic uremic (aHUS) syndrome, sepsis, organ transplantation, inflammation (including, but not limited to, inflammation associated with cardiopulmonary bypass surgery and kidney dialysis), glomerulonephritis (including, but not limited to, anti-neutrophil cytoplasmic antibody (ANCA)-mediated glomerulonephritis, lupus, and combinations thereof.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The terms "inhibit" and "inhibition," as used herein, means to reduce, suppress, diminish or block an activity or function by at least about 10% relative to a control value. Preferably, the activity is suppressed or blocked by 50% compared to a control value, more preferably by 75%, and even more preferably by 95%.

The terms "effective amount" and "pharmaceutically effective amount" refer to a sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation.

The terms "patient," "subject," "individual," and the like are used interchangeably herein, and refer to any animal, preferably a mammal, and most preferably a human, having a complement system, including a human in need of therapy for, or susceptible to, a condition or its sequelae. The individual may include, for example, dogs, cats, pigs, cows, sheep, goats, horses, rats, monkeys, and mice and humans.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected/homeostatic) respective characteristic. Characteristics which are normal or expected for one cell, tissue type, or subject, might be abnormal for a different cell or tissue type.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

An "effective amount" or "therapeutically effective amount" of a compound is that amount of compound which is sufficient to provide a beneficial effect to the subject to which the compound is administered.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

A "therapeutic" treatment is a treatment administered to a subject who exhibits signs of pathology, for the purpose of diminishing or eliminating those signs.

As used herein, "treating a disease or disorder" means reducing the frequency and/or severity of a sign and/or symptom of the disease, disorder or pathology is experienced by a patient. Disease, disorder and pathology are used interchangeably herein.

The phrase "biological sample" as used herein, is intended to include any sample comprising a cell, a tissue, or a bodily fluid in which expression of a nucleic acid or polypeptide can be detected. Examples of such biological samples include but are not limited to blood, lymph, bone marrow, biopsies and smears. Samples that are liquid in nature are referred to herein as "bodily fluids." Biological samples may be obtained from a patient by a variety of techniques including, for example, by scraping or swabbing an area or by using a needle to obtain bodily fluids. Methods for collecting various body samples are well known in the art.

The term "antibody," as used herein, refers to an immunoglobulin molecule which is able to specifically bind to a specific epitope of an antigen. Antibodies can be intact immunoglobulins derived from natural sources, or from recombinant sources and can be immunoreactive portions of intact immunoglobulins. The antibodies in the present invention may exist in a variety of forms including, for example, polyclonal antibodies, monoclonal antibodies, intracellular antibodies ("intrabodies"), Fv, Fab, Fab', F(ab)2 and F(ab')2, as well as single chain antibodies (scFv), heavy chain antibodies, such as camelid antibodies, and humanized antibodies (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

As used herein, the term "heavy chain antibody" or "heavy chain antibodies" comprises immunoglobulin molecules derived from camelid species, either by immunization with a peptide and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of VH (variable heavy chain immunoglobulin) genes from an animal.

A "chimeric antibody" refers to a type of engineered antibody which contains a naturally-occurring variable region (light chain and heavy chains) derived from a donor antibody in association with light and heavy chain constant regions derived from an acceptor antibody.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity (see, e.g., 1989, Queen et al., Proc. Natl. Acad Sci USA, 86:10029-10032; 1991, Hodgson et al., Bio/Technology, 9:421). A suitable human acceptor antibody may be one selected from a conventional database, e.g., the KABAT database, Los Alamos database, and Swiss Protein database, by homology to the nucleotide and amino acid sequences of the donor antibody. A human antibody characterized by a homology to the framework regions of the donor antibody (on an amino acid basis) may be suitable to provide a heavy chain constant region and/or a heavy chain variable framework region for insertion of the donor CDRs. A suitable acceptor antibody capable of donating light chain constant or variable framework regions may be selected in a similar manner. It should be noted that the acceptor antibody heavy and light chains are not required to originate from the same acceptor antibody. The prior art describes several ways of producing such humanized antibodies (see for example EP-A-0239400 and EP-A-054951).

The term "donor antibody" refers to an antibody (monoclonal, and/or recombinant) which contributes the amino acid sequences of its variable regions, CDRs, or other functional fragments or analogs thereof to a first immunoglobulin partner, so as to provide the altered immunoglobulin coding region and resulting expressed altered antibody with the antigenic specificity and neutralizing activity characteristic of the donor antibody.

The term "acceptor antibody" refers to an antibody (monoclonal and/or recombinant) heterologous to the donor antibody, which contributes all (or any portion, but in some embodiments all) of the amino acid sequences encoding its heavy and/or light chain framework regions and/or its heavy and/or light chain constant regions to the first immunoglobulin partner. In certain embodiments a human antibody is the acceptor antibody.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

As used herein, an "immunoassay" refers to any binding assay that uses an antibody capable of binding specifically to a target molecule to detect and quantify the target molecule.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific.

In some instances, the terms "specific binding" or "specifically binding", can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "coding region" of a mRNA molecule also consists of the nucleotide residues of the mRNA molecule which are matched with an anti-codon region of a transfer RNA molecule during translation of the mRNA molecule or which encode a stop codon. The coding region may thus include nucleotide residues comprising codons for amino acid residues which are not present in the mature protein encoded by the mRNA molecule (e.g., amino acid residues in a protein export signal sequence).

"Complementary" as used herein to refer to a nucleic acid, refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "DNA" as used herein is defined as deoxyribonucleic acid.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

"Isolated" means altered or removed from the natural state. For example, a nucleic acid or a peptide naturally present in its normal context in a living animal is not "isolated," but the same nucleic acid or peptide partially or completely separated from the coexisting materials of its natural context is "isolated." An isolated nucleic acid or protein can exist in substantially purified form, or can exist in a non-native environment such as, for example, a host cell.

An "isolated nucleic acid" refers to a nucleic acid segment or fragment which has been separated from sequences which flank it in a naturally occurring state, i.e., a DNA fragment which has been removed from the sequences which are normally adjacent to the fragment, i.e., the sequences adjacent to the fragment in a genome in which it naturally so occurs. The term also applies to nucleic acids which have been substantially purified from other components which naturally accompany the nucleic acid, i.e., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (i.e., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "progeny" as used herein refers to a descendent or offspring and includes the offspring of a mammal, and also included the differentiated or undifferentiated decedent cell derived from a parent cell. In one usage, the term progeny refers to a descendent cell which is genetically identical to the parent. In another use, the term progeny refers to a descendent cell which is genetically and phenotypically identical to the parent. In yet another usage, the term progeny refers to a descendent cell that has differentiated from the parent cell.

The term "RNA" as used herein is defined as ribonucleic acid.

The term "recombinant DNA" as used herein is defined as DNA produced by joining pieces of DNA from different sources.

The term "recombinant polypeptide" as used herein is defined as a polypeptide produced by using recombinant DNA methods.

As used herein, "conjugated" refers to covalent attachment of one molecule to a second molecule.

"Variant" as the term is used herein, is a nucleic acid sequence or a peptide sequence that differs in sequence from a reference nucleic acid sequence or peptide sequence respectively, but retains essential biological properties of the reference molecule. Changes in the sequence of a nucleic acid variant may not alter the amino acid sequence of a peptide encoded by the reference nucleic acid, or may result in amino acid substitutions, additions, deletions, fusions and truncations. Changes in the sequence of peptide variants are typically limited or conservative, so that the sequences of the reference peptide and the variant are closely similar overall and, in many regions, identical. A variant and reference peptide can differ in amino acid sequence by one or more substitutions, additions, deletions in any combination. A variant of a nucleic acid or peptide can be a naturally occurring such as an allelic variant, or can be a variant that is not known to occur naturally. Non-naturally occurring variants of nucleic acids and peptides may be made by mutagenesis techniques or by direct synthesis The term "breeding" is used herein to refer to the propagation of a species with the result being at least one offspring.

The term "natural breeding" is used herein to refer to the propagation of a species by sexual union.

The term "inbred animal" is used herein to refer to an animal that has been interbred with other similar animals of the same species in order to preserve and fix certain characteristics, or to prevent other characteristics from being introduced into the breeding population.

The term "outbred animal" is used herein to refer to an animal that breeds with any other animal of the same species without regard to the preservation of certain characteristics.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

This invention relates to the inhibition of the alternative pathway (AP) of complement using an anti-properdin antibody. In one embodiment, the invention is directed to methods of treating an AP-mediated pathology or AP-mediated condition in an individual by contacting the individual with an anti-properdin antibody.

In one embodiment, the invention is a method of treating an AP-mediated pathology in an individual, comprising the step of administering to said individual an anti-properdin antibody, thereby inhibiting the generation of a C3bBb protein complex. Examples of complement-mediated pathologies that can be treated using the methods of the invention include, but are not limited to macular degeneration, ischemia reperfusion injury, arthritis, rheumatoid arthritis, paroxysmal nocturnal hemoglobinuria (PNH) syndrome, atypical hemolytic uremic (aHUS) syndrome, asthma, inflammation, glomerulonephritis, lupus, organ transplantation sepsis, or combinations thereof.

The ability of the immune system to discriminate between "self" and "non-self" antigens is vital to the functioning of the immune system as a specific defense against invading microorganisms. "Non-self" antigens are those antigens on substances entering or present in the body which are detectably different or foreign from the animal's own constituents, whereas "self" antigens are those which, in the healthy animal, are not detectably different or foreign from its own constituents. In various embodiments of the methods described herein, the AP activation that is inhibited is that which was triggered by at least one of the group consisting of a microbial antigen, a non-biological foreign surface, altered self-tissue, or combinations thereof. One example of a non-biological foreign surface is blood tubing such as that used in cardio-pulmonary bypass surgery or kidney dialysis. Examples of altered self-tissues include apoptotic, necrotic and ischemia-stressed tissues and cells, or combinations thereof.

In some embodiments, the anti-properdin antibodies of the invention selectively inhibit the AP, but do not inhibit the classical pathway (CP) or the lectin pathway (LP). Generally, the CP is initiated by antigen-antibody complexes, the LP is activated by binding of lectins to sugar molecules on microbial surfaces, while the AP is constitutively active at a low level but can be quickly amplified on bacterial, viral, and parasitic cell surfaces due to the lack of regulatory proteins. Host cells are usually protected from AP complement activation by regulatory proteins. But in some situations, such as when the regulatory proteins are defective or missing, the AP can also be activated uncontrollably on host cells, leading to complement-mediated pathology. The CP consists of components C1, C2, C4 and converges with the AP at the C3 activation step. The LP consists of mannose-binding lectins (MBLs) and MBL-associated serine proteases (Masps) and shares with the CP the components C4 and C2. The AP consists of components C3 and several factors, such as Factor B, Factor D, properdin and the fluid phase regulator Factor H. Complement activation consists of three stages: (a) recognition, (b) enzymatic activation, and (c) membrane attack leading to cell death. The first phase of CP complement activation begins with C1. C1 is made up of three distinct proteins: a recognition subunit, C1q, and the serine protease subcomponents, C1r and C1s, which are bound together in a calcium-dependent tetrameric complex, C1r2 s2. An intact C1 complex is necessary for physiological activation of C1 to result. Activation occurs when the intact C1 complex binds to immunoglobulin complexed with antigen. This binding activates C1s which then cleaves both the C4 and C2 proteins to generate C4a and C4b, as well as C2a and C2b. The C4b and C2a fragments combine to form the C3 convertase, C4b2a, which in turn cleaves C3 to form C3a and C3b. Activation of the LP is initiated by MBL binding to certain sugars on the target surface and this triggers the activation of Masps which then cleaves C4 and C2 in a manner analogous to the activity of C1s of the CP, resulting in the generation of the C3 convertase, C4b2a. Thus, the CP and LP are activated by different mechanisms but they share the same components C4 and C2 and both pathways lead to the generation of the same C3 convertase, C4b2a. The cleavage of C3 by C4b2a into C3b and C3a is a central event of the complement pathway for two reasons. It initiates the AP amplification loop because surface deposited C3b is a central intermediate of the AP. Both C3a and C3b are biologically important. C3a is proinflammatory and together with C5a are referred to as anaphylatoxins. C3b and its further cleavage products also bind to complement receptors present on neutrophils, eosinophils, monocytes and macrophages, thereby facilitating phagocytosis and clearance of C3b-opsonized particles. Finally, C3b can is associate with C4b2a to form the C5 convertase of the CP and LP to activate the terminal complement sequence, leading to the production of C5a, a potent proinflammatory mediator, and the assembly of the lytic membrane attack complex (MAC), C5-C9.

Because the CP and AP play a critical role in host defense and many complement-dependent human pathologies are mediated by the AP, it is desirable to selectively inhibit the AP in the treatment of such human pathologies. Accordingly, in preferred embodiments of the methods described herein, the immunity provided by the CP and LP is maintained, while the AP is selectively inhibited. Thus, in various embodiments, the anti-properdin antibodies used in the methods described herein, do not inhibit the CP and LP. In certain embodiments, the anti-properdin antibodies described herein are distinct from anti-properdin antibodies developed previously which inhibit both AP and CP.

The AP is thought to be constitutively active at a low level due to spontaneous hydrolysis of C3 to form C3(H2O). C3(H2O) behaves like C3b in that it can associate with fB, which make fB susceptible to fD cleavage and activation. The resultant C3(H2O)Bb then cleaves C3 to produce C3b and C3a to initiate the AP cascade by forming the C3 convertase of the AP, C3bBb. As the initial C3 convertase generates increasing amounts of C3b, an amplification loop is established. It should be noted that because the CP and LP also generate C3b, wherein C3b can bind factor B and engages the AP, the AP amplification loop also participates in the CP and LP once these pathways are activated. Thus, the AP consists of two functional entities: an independent complement activation pathway that is unrelated to CP or LP and an amplification process that does participate and contribute to the full manifestation of CP and LP. In one embodiment, the anti-properdin antibodies used in the methods described herein selectively inhibit the AP activation process and do not interfere with the AP amplification loop of the CP and LP.

Properdin is structurally composed of an N-terminal domain and six thrombospondin type I repeat (TSR) domains. Under physiological conditions, it exists in plasma as cyclic polymers (dimers, trimers, tetramers), formed by head to tail associations of monomers. Human properdin is encoded on the short arm of the X chromosome and its deficiency, especially when combined with C2, MBL or IgG2 deficiency, constitutes a risk factor for lethal *Neisseria* infections.

Figure 3:
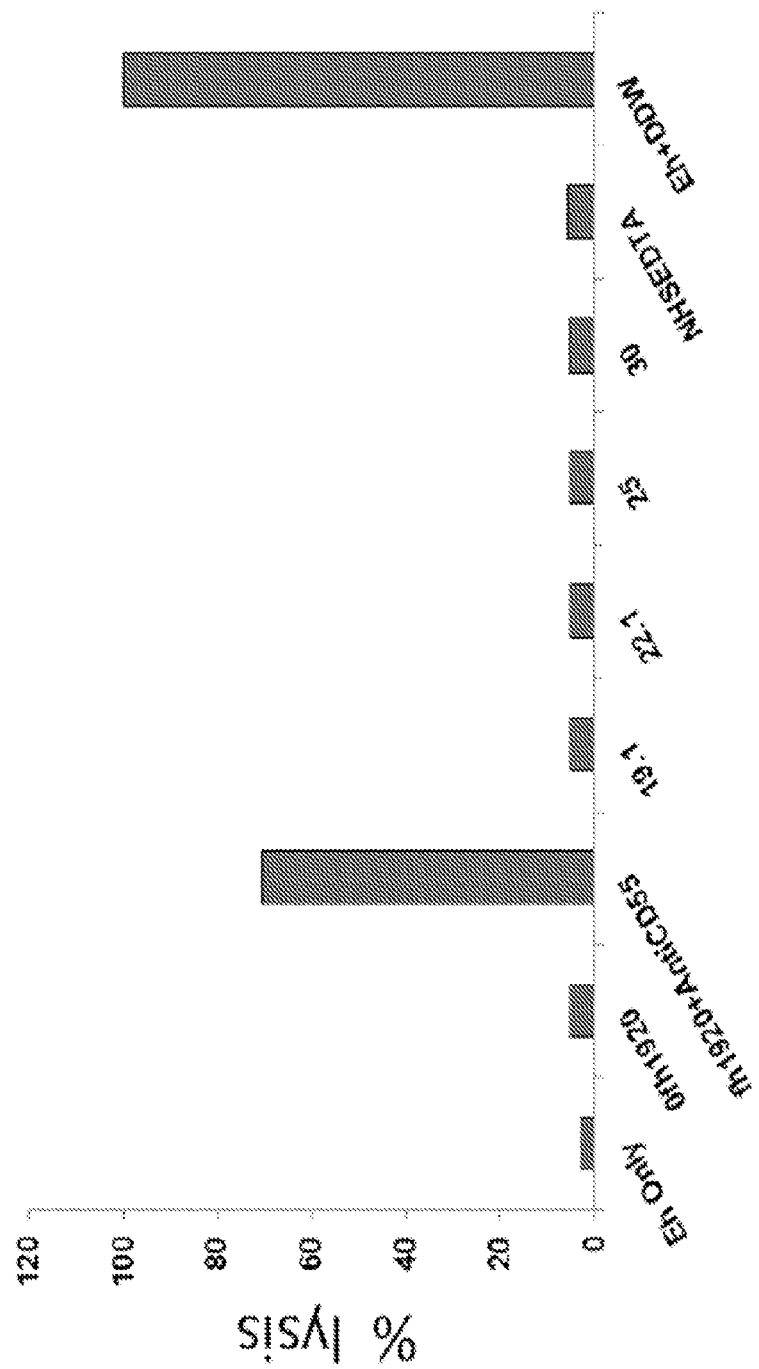
FIG. 3 depicts the results of experiments demonstrating that anti-human properdin mAbs inhibit human red blood cell (RBC) lysis caused by fH and DAF dysfunction. Human RBCs are not lysed in the absence of human serum (Eh only). They are also resistant to lysis by human serum (50%) in the absence of fH 19-20, a recombinant fH fragment that prevents fH interaction with autologous cells (0fh1920). However, when human RBCs are incubated with 50% human serum in the presence of 30 µM fH 19-20 and 7.5 µg/ml of a function-blocking anti-decay accelerating factor (DAF, a membrane complement regulator) mAb (fh1920+ AntiCD55), about 70% of the RBCs lysed. This lysis was completely inhibited by each of the 4 anti-properdin mAbs (19.1, 22.1, 25, 30) at 5 µg/ml. An RBC sample treated with distilled water (Eh+DDW) caused complete lysis and served as a positive control. An RBC sample in normal human serum treated with EDTA (NHSEDTA) served as a negative control (no lysis, because EDTA blocks complement activation). Lysis assays were performed in Mg++-EGTA GVB++ buffer to allow only AP complement activation.

It appears that the need for properdin in AP initiation is variable and depends on the nature of the activating surface. By way of non-limiting examples, properdin appears to be indispensable for LPS- and LOS-induced AP activation as well as for AP-mediated autologous tissue injury such as extravascular hemolysis of Crry-deficient mouse erythrocytes (see U.S. Pat. App. No. 2010/0263061). The invention described herein discloses that properdin is essential for human AP complement mediated red blood cell lysis in the context of fH and DAF dysfunction/blockade (FIG. 3). The invention described herein also discloses that properdin is essential for autologous serum lysis of PNH red blood cells (FIG. 24). On the other hand, zymosan-induced AP activation is moderately impaired by properdin deficiency, and properdin does not appear to play a substantial role in CVF- and CP-triggered AP amplification (see U.S. Pat. App. No. 2010/0263061). AP activation on a given surface may represent the balance between properdin-dependent promotion via C3bBb stabilization and factor H (fH)-dependent inhibition of C3 'tick-over.' An AP activator for which properdin is not essential may have limited interaction with fH and, as a result of lacking sufficient fH-dependent inhibition, spontaneous C3 activation and amplification could occur as a default process without the help of properdin. Accordingly, in various embodiments of the invention described herein, inhibition of properdin function by the anti-properdin antibodies of the invention offers several advantages, including: it does not compromise the AP amplification loop of the CP and LP, leaving these pathways fully active for host defense;

it does not completely eliminate AP complement activation since not all AP activators (i.e. pathogens) require properdin to trigger this pathway, reducing the degree of impairment in host defense when compared with other methods of AP inhibition such as anti-fB and anti-fD antibodies.

In one embodiment, the activity of the AP that is inhibited using a method of invention is AP activation induced by at least one of the group selected from a lipopolysacchride (LPS), lipooligosaccharide (LOS), pathogen-associated molecular patterns (PAMPs) and danger-associated molecular patterns (DAMPs). In another embodiment, the activity of the AP that is inhibited using a method of invention is the generation of C3bBb protein complex. In another embodiment, the activity of the AP that is inhibited using a method of invention is properdin dependent.

In some embodiments, the methods of the present invention preserve the ability of the individual to combat an infection through the CP and LP. In one embodiment, the invention is a method of inhibiting AP activation induced by bacterial lipooligosaccharide (LOS) in an individual, comprising the step of administering to said individual an anti-properdin antibody, and thereby inhibiting an AP activation induced by bacterial LOS in an individual. In another embodiment, provided herein is a method of inhibiting AP activation induced by a bacterial LPS. In certain embodiments, the AP activation is induced by *S. typhosa* LPS, and the inhibitors used in the methods provided herein do not inhibit AP activity induced by *S. minnesota* LPS or *E. coli* LPS. In various embodiments, the anti-properdin antibodies of the invention selectively inhibit the AP, but do not inhibit CP-triggered complement activation, LP-triggered complement activation, zymosan-induced activation, or cobra venom factor-induced activation.

In one embodiment, provided herein is a method of inhibiting a pathogen-associated molecular pattern-mediated AP activation in an individual, comprising the step of administering to said individual an anti-properdin antibody, thereby inhibiting a PAMP-mediated AP activation in an individual. Examples of PAMPs whose activation of AP can be inhibited by the methods of the invention, include, but are not limited to, a muramyl dipeptide (MDP), a CpG motif from bacterial DNA, double-stranded viral RNAs, a peptidoglycan, a lipoteichoic acid, an outer surface protein A from *Borrelia burgdorferi*, a synthetic mycoplasmal macrophage-activating lipoprotein-2, tripalmitoyl-cysteinyl-seryl-(lysyl)3-lysine (P3CSK4), a dipalmitoyl-CSK4 (P2-CSK4), a monopalmitoyl-CSK4 (PCSK4), amphotericin B, a triacylated or diacylated bacterial polypeptide, and combinations thereof.

In one embodiment, the invention is a method of inhibiting initiation of AP activation in an individual, comprising the step of administering to said individual an anti-properdin antibody, thereby inhibiting initiation of AP activation in an individual. In another embodiment, provided herein is a method of inhibiting amplification of AP activation in an individual, comprising the step of administering to said individual an inhibitor of the AP, thereby inhibiting amplification of AP activation in an individual. Examples of these embodiments are PNH patients who suffer from AP complement-mediated hemolysis and individuals suffering from AP complement-mediated aHUS, asthma, ischemic/reperfusion injury, rheumatoid arthritis and ANCA-mediated kidney diseases. In various embodiments of the invention, diseases and disorders that can be treated using the compositions and methods of the invention include, but are not limited to, AP complement-mediated hemolysis, AP complement-mediated aHUS, asthma, ischemic/reperfusion injury, rheumatoid arthritis and ANCA-mediated kidney diseases.

In various embodiments, provided herein are methods of identifying a potential antibody having inhibitory effects on the AP, comprising the steps of: a) administering the anti-properdin antibody to an individual; b) measuring the resulting phenotype of the individual; and c) comparing the resulting phenotype of the individual to the phenotype of a properdin$^{-/-}$ knockout animal (see U.S. Pat. App. No. 2010/0263061). In another embodiment, the anti-properdin antibody used in the methods provided herein is identified by the method of selecting a potential therapeutic compound using the properdin$^{-/-}$ knockout animal (see U.S. Pat. App. No. 2010/0263061).

In various other embodiments, provided herein are methods of identifying a potential anti-properdin antibody having inhibitory effects on the AP. One such method includes the steps of: a) coating a plate with lipopolysaccharide (LPS); b) washing the plate to remove unbound LPS; c) adding bovine serum albumin (BSA) in phosphate buffered saline (PBS); d) washing the plate to remove unbound BSA; e) adding a mixture of a candidate anti-properdin antibody compound mixed into human serum; f) washing the plate; g) adding an anti-human C3 antibody; h) washing the plate to remove unbound antibody; i) adding TMB Substrate Reagent; j) adding sulphuric acid to stop the reaction; k) measuring the optical density at 450 nm; l) comparing the optical density of the plate containing the candidate anti-properdin antibody compound to the optical density of a positive comparator control and a negative comparator control; wherein when the optical density is diminished as compared with the positive comparator control, the anti-properdin antibody is identified.

Anti-Properdin Antibodies

In some embodiments, the invention includes compositions comprising an antibody that specifically binds to properdin. In one embodiment, the anti-properdin antibody is a polyclonal antibody. In another embodiment, the anti-properdin antibody is a monoclonal antibody. In some embodiments, the anti-properdin antibody is a chimeric antibody. In further embodiments, the anti-properdin antibody is a humanized antibody. In preferred embodiments, the properdin is human properdin.

In one embodiment, the anti-properdin antibody comprises at least one of the CDRs selected from the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO: 10. In another embodiment, the anti-properdin antibody comprises all of the CDRs of the group consisting of: VH-CDR1: SEQ ID NO:3; VH-CDR2: SEQ ID NO:4; VH-CDR3: SEQ ID NO:5; VL-CDR1: SEQ ID NO:8; VL-CDR2: SEQ ID NO:9; and VL-CDR3: SEQ ID NO:10.

In some embodiments, the anti-properdin antibody comprises a heavy chain comprising the amino acid sequence of SEQ ID NO:2. In other embodiments, the anti-properdin antibody comprises a light chain comprising the amino acid sequence of SEQ ID NO:7. In another embodiment, the anti-properdin antibody is a monoclonal antibody designated mAb 19.1. The monoclonal anti-properdin antibody designated mAb 19.1 comprises a heavy chain comprising the amino acid sequence of SEQ ID NO:2 and a light chain comprising the amino acid sequence of SEQ ID NO:7. In some embodiments, the monoclonal anti-properdin antibody designated mAb 19.1 is humanized.

In some embodiments, the anti-properdin antibody of the invention binds to an epitope comprising at least one amino acid of TSR5 (SEQ ID NO:60). In some embodiments, the anti-properdin antibody of the invention specifically binds to an epitope comprising at least one amino acid of the amino acid sequence RGRTCRGRKFDGHRCAGQQQDIRHCYSIQHCP (SEQ ID NO:52). In some embodiments, the anti-properdin antibody that specifically binds to an epitope comprising at least one amino acid of SEQ ID NO:52 is the mAb designated as mAb 19.1. In some so embodiments, the anti-properdin antibody is an antibody that competes for binding with the antibody designated as mAb 19.1. In various embodiments, the epitope to which the antibody of the invention can bind is a linear epitope or a conformational epitope.

In one embodiment, the anti-properdin antibody comprises at least one of the CDRs selected from the group consisting of: VH-CDR1: SEQ ID NO:13; VH-CDR2: SEQ ID NO: 14; VH-CDR3: SEQ ID NO:15; VL-CDR1: SEQ ID NO: 18; VL-CDR2: SEQ ID NO:19; and VL-CDR3: SEQ ID NO:20. In another embodiment, the anti-properdin antibody comprises all of the CDRs of the group consisting of: VH-CDR1: SEQ ID NO:13; VH-CDR2: SEQ ID NO:14; VH-CDR3: SEQ ID NO:15; VL-CDR1: SEQ ID NO:18; VL-CDR2: SEQ ID NO: 19; and VL-CDR3: SEQ ID NO:20.

In some embodiments, the anti-properdin antibody comprises a heavy chain comprising the amino acid sequence of SEQ ID NO:12. In other embodiments, the anti-properdin antibody comprises a light chain comprising the amino acid sequence of SEQ ID NO: 17. In another embodiment, the anti-properdin antibody is a monoclonal antibody designated mAb 25. The monoclonal anti-properdin antibody designated mAb 25 comprises a heavy chain comprising the amino acid sequence of SEQ ID NO: 12 and a light chain comprising the amino acid sequence of SEQ ID NO: 17. In some embodiments, the monoclonal anti-properdin antibody designated mAb 25 is humanized.

In some embodiments, the anti-properdin antibody of the invention binds to an epitope comprising at least one amino acid of TSR5 (SEQ ID NO:60) and/or TSR6 (SEQ ID NO:61). In some embodiments, the anti-properdin antibody of the invention specifically binds to an epitope comprising at least one amino acid of the amino acid sequence LVVEEKRPCLHVPACKDPEEEEL (SEQ ID NO:53). In some embodiments, the anti-properdin antibody of the invention specifically binds to an epitope comprising cysteine 62 (C62), present in SEQ ID NO:61. In some embodiments, the anti-properdin antibody of the invention specifically binds to an epitope comprising cysteine 78 (C78), present in SEQ ID NO:53. In some embodiments, the anti-properdin antibody that specifically binds to an epitope comprising the amino acid of SEQ TD NO:53 is the mAb designated as mAb 25. In some embodiments, the anti-properdin antibody is an antibody that competes for binding with the antibody designated as mAb 25. In various embodiments, the epitope to which the antibody of the invention can bind is a linear epitope or a conformational epitope.

In one embodiment, the anti-properdin antibody comprises at least one of the CDRs selected from the group consisting of: VH-CDR1: SEQ ID NO:23; VH-CDR2: SEQ ID NO:24; VH-CDR3: SEQ ID NO:25; VL-CDR1: SEQ ID NO:28; VL-CDR2: SEQ ID NO:29; and VL-CDR3: SEQ ID NO:30. In another embodiment, the anti-properdin antibody comprises all of the CDRs of the group consisting of: VH-CDR1: SEQ ID NO:23; VH-CDR2: SEQ ID NO:24; VH-CDR3: SEQ ID NO:25; VL-CDR1: SEQ ID NO:28; VL-CDR2: SEQ ID NO:29; and VL-CDR3: SEQ ID NO:30.

In some embodiments, the anti-properdin antibody comprises a heavy chain comprising the amino acid sequence of SEQ ID NO:22. In other embodiments, the anti-properdin antibody comprises a light chain comprising the amino acid sequence of SEQ ID NO:27. In another embodiment, the anti-properdin antibody is a monoclonal antibody designated mAb 22.1. The monoclonal anti-properdin antibody designated mAb 22.1 comprises a heavy chain comprising the amino acid sequence of SEQ ID NO:22 and a light chain comprising the amino acid sequence of SEQ ID NO:27. In other embodiments, the anti-properdin antibody is an antibody that competes for binding with the antibody designated as mAb 22.1. In some embodiments, the monoclonal anti-properdin antibody designated mAb 22.1 is humanized.

In one embodiment, the anti-properdin antibody comprises at least one of the CDRs selected from the group consisting of: VH-CDR1: SEQ ID NO:33; VH-CDR2: SEQ ID NO:34; VH-CDR3: SEQ ID NO:35; VL-CDR1: SEQ ID NO:38; VL-CDR2: SEQ ID NO:39; and VL-CDR3: SEQ ID NO:40. In another embodiment, the anti-properdin antibody comprises all of the CDRs of the group consisting of: VH-CDR1: SEQ ID NO:33; VH-CDR2: SEQ ID NO:34; VH-CDR3: SEQ ID NO:35; VL-CDR1: SEQ ID NO:38; VL-CDR2: SEQ TD NO:39; and VL-CDR3: SEQ ID NO:40.

In some embodiments, the anti-properdin antibody comprises a heavy chain comprising the amino acid sequence of SEQ ID NO:32. In other embodiments, the anti-properdin antibody comprises a light chain comprising the amino acid sequence of SEQ ID NO:37. In another embodiment, the anti-properdin antibody is a monoclonal antibody designated mAb 30. The monoclonal anti-properdin antibody designated mAb 30 comprises a heavy chain comprising the amino acid sequence of SEQ ID NO:32 and a light chain comprising the amino acid sequence of SEQ ID NO:37. In other embodiments, the anti-properdin antibody is an antibody that competes for binding with the antibody designated as mAb 30. In some embodiments, the monoclonal anti-properdin antibody designated mAb 30 is humanized.

In other embodiments, the anti-properdin antibody comprises a humanized heavy chain comprising the amino acid sequence of SEQ ID NO:42. In some embodiments, the anti-properdin antibody comprises a humanized heavy chain comprising the amino acid sequence of SEQ ID NO:44. In still other embodiments, the anti-properdin antibody comprises a humanized light chain comprising the amino acid sequence of SEQ ID NO:47. In some embodiments, the anti-properdin antibody comprises a humanized antibody comprising a heavy chain comprising the amino acid sequence of SEQ ID NO:42 and a light chain comprising the amino acid sequence of SEQ ID NO:47. In other embodiments, anti-properdin antibody comprises a humanized antibody comprising a heavy chain comprising the amino acid sequence of SEQ ID NO:44 and a light chain comprising the amino acid sequence of SEQ ID NO:47. In further embodiments, the anti-properdin antibody is an antibody that competes for binding with a humanized antibody described herein.

In some embodiments, the anti-properdin antibody comprises a humanized heavy chain comprising the amino acid sequence of SEQ ID NO:49. In other embodiments, the anti-properdin antibody comprises a humanized light chain comprising the amino acid sequence of SEQ ID NO:51. In some embodiments, the anti-properdin antibody comprises a humanized antibody comprising a heavy chain comprising the amino acid sequence of SEQ ID NO:49 and a light chain comprising the amino acid sequence of SEQ ID NO:51. In further embodiments, the anti-properdin antibody is an antibody that competes for binding with a humanized antibody described herein.

In some embodiments, the anti-properdin antibody comprises a chimeric heavy chain comprising the amino acid sequences of SEQ ID NO:2 and a human heavy chain constant region, such as, by way of non-limiting example, a human IgG4 constant region comprising the amino acid sequence of SEQ ID NO:63. In other embodiments, the anti-properdin antibody comprises a chimeric light chain comprising the amino acid sequence of SEQ ID NO:7 and a human light chain constant region, such as, by way of non-limiting example, a human kappa light chain constant region comprising the amino acid sequence of SEQ ID NO:64. In a certain embodiment, the anti-properdin antibody comprises a chimeric heavy chain comprising the amino acid sequences of SEQ ID NO:2 and SEQ ID NO:63 and a chimeric light chain comprising the amino acid sequences of SEQ ID NO:7 and SEQ ID NO:64.

In some embodiments, the anti-properdin antibody comprises a chimeric heavy chain comprising the amino acid sequences of SEQ ID NO: 12 and a human heavy chain constant region, such as, by way of non-limiting example, a human IgG4 constant region comprising the amino acid sequence of SEQ ID NO:63. In other embodiments, the anti-properdin antibody comprises a chimeric light chain comprising the amino acid sequence of SEQ ID NO: 17 and a human light chain constant region, such as, by way of non-limiting example, a human kappa light chain constant region comprising the amino acid sequence of SEQ ID NO:64. In a certain embodiment, the anti-properdin antibody comprises a chimeric heavy chain comprising the amino acid sequences of SEQ ID NO:12 and SEQ ID NO:63 and a chimeric light chain comprising the amino acid sequences of SEQ ID NO:17 and SEQ ID NO:64.

In some embodiments, the anti-properdin antibody comprises a chimeric heavy chain comprising the amino acid sequences of SEQ ID NO:22 and a human heavy chain constant region, such as, by way of non-limiting example, a human IgG4 constant region comprising the amino acid sequence of SEQ ID NO:63. In other embodiments, the anti-properdin antibody comprises a chimeric light chain comprising the amino acid sequence of SEQ ID NO:27 and a human light chain constant region, such as, by way of non-limiting example, a human kappa light chain constant region comprising the amino acid sequence of SEQ ID NO:64. In a certain embodiment, the anti-properdin antibody comprises a chimeric heavy chain comprising the amino acid sequences of SEQ ID NO:22 and SEQ ID NO:63 and a chimeric light chain comprising the amino acid sequences of SEQ ID NO:27 and SEQ ID NO:64.

In some embodiments, the anti-properdin antibody comprises a chimeric heavy chain comprising the amino acid sequences of SEQ ID NO:32 and a human heavy chain constant region, such as, by way of non-limiting example, a human IgG4 constant region comprising the amino acid sequence of SEQ ID NO:63. In other embodiments, the anti-properdin antibody comprises a chimeric light chain comprising the amino acid sequence of SEQ ID NO:37 and a human light chain constant region, such as, by way of non-limiting example, a human kappa light chain constant region comprising the amino acid sequence of SEQ ID NO:64. In a certain embodiment, the anti-properdin antibody comprises a chimeric heavy chain comprising the amino acid sequences of SEQ ID NO:32 and SEQ ID NO:63 and a chimeric light chain comprising the amino acid sequences of SEQ ID NO:37 and SEQ ID NO:64.

Screening Assays

The present invention has application in various screening assays, including, determining whether a candidate anti-properdin antibody can inhibit the AP.

In some embodiments, the level of AP activity in the presence of the candidate anti-properdin antibody is compared with AP activity detected in a positive comparator control. The positive comparator control comprises AP activation in the absence of added test compound. In some embodiments, the candidate anti-properdin antibody is identified as an inhibitor of the AP when the AP activity in the presence of the candidate anti-properdin antibody is less than about 70% of the AP activity detected in a positive comparator control; this corresponds to greater than about 30% inhibition of AP activity in the presence of the test compound. In other embodiments, the candidate anti-properdin antibody is identified as an inhibitor of the AP when the AP activity in the presence of the candidate anti-properdin antibody is less than about 80% of the AP activity detected in a positive comparator control; this corresponds to greater than about 20% inhibition of AP activity in the presence of the test compound. In still other embodiments, the candidate anti-properdin antibody is identified as an inhibitor of the AP when the AP activity in the presence of the candidate anti-properdin antibody is less than about 90% of the AP activity detected in a positive comparator control; this corresponds to greater than about 10% inhibition of AP activity in the presence of the test compound. In some embodiments, the level of AP inhibition by the candidate anti-properdin antibody is compared with the level of inhibition detected in a negative comparator control.

A variety of immunoassay formats, including competitive and non-competitive immunoassay formats, antigen capture assays, two-antibody sandwich assays, and three-antibody sandwich assays are useful methods of the invention (Self et al., 1996, Curr. Opin. Biotechnol. 7:60-65). The invention should not be constnrued to be limited to any one type of known or heretofor unknown assay, provided that the assay is able to detect the inhibition of the AP.

Hemolytic assays are included in the methods of the invention. In various embodiments, red blood cells (RBCs) are obtained from normal (healthy) individuals or from individuals displaying signs or symptoms of a disease or disorder, such as, for example, PNH. In various embodiments, RBCs are lysed with 5% to 75% normal human serum (NHS) in the so presence of a recombinant fH fragment comprising complement control protein (CCP) repeat 19 and 20 of fH (fH19-20, 5-50 µM) and anti-DAF neutralizing antibodies (3-20 µg/ml). In some embodiments, RBCs from individuals displaying signs or symptoms of a disease or disorder, such as PNH, are lysed with acidified serum. In some embodiments, hemolytic assays are performed in GVB++-Mg++-EGTA buffer to allow only AP complement activation, but the skilled artisan will understand that other appropriate buffers can be used, so long as the buffer allows only AP complement activation. In one embodiment, the degree of lysis is calculated by measuring the OD410 of the supernatant of the incubation mixture, as a measure of the release of hemoglobin into solution. In various embodiments, at least one anti-properdin antibody is added, at a concentration from about 1 µg/ml to about 50 µg/ml, and pre-incubated with serum, and the extent of inhibition of hemolysis of RBCs is measured.

Enzyme-linked immunosorbent assays (ELISAs) are useful in the methods of the invention. An enzyme such as, but not limited to, horseradish peroxidase (HRP), alkaline phosphatase, beta-galactosidase or urease can be linked, for example, to an anti-C3 antibody or to a secondary antibody for use in a method of the invention. A horseradish-peroxidase detection system may be used, for example, with the chromogenic substrate tetramethylbenzidine (TMB), which yields a soluble product in the presence of hydrogen peroxide that is detectable at 450 mm. Other convenient enzyme-linked systems include, for example, the alkaline phosphatase detection system, which may be used with the chromogenic substrate p-nitrophenyl phosphate to yield a soluble product readily detectable at 405 nm. Similarly, a beta-galactosidase detection system may be used with the chromogenic substrate o-nitrophenyl-beta-D-galactopyranoside (ONPG) to yield a soluble product detectable at 410 nm. Alternatively, a urease detection system may be used with a substrate such as urea-bromocresol purple (Sigma Immunochemicals, St. Louis, Mo.). Useful enzyme-linked primary and secondary antibodies can be obtained from any number of commercial sources.

Chemiluminescent detection is also useful for detecting the inhibition of the AP. Chemiluminescent secondary antibodies may be obtained from any number of commercial sources.

Fluorescent detection is also useful for detecting the inhibition of the AP. Useful fluorochromes include, but are not limited to, DAPI, fluorescein, Hoechst 33258, R-phycocyanin, B-phycoerythrin, R-phycoerythrin, rhodamine, Texas red and lissamine-Fluorescein- or rhodamine-labeled antibodies.

Radioimmunoassays (RIAs) are also useful in the methods of the invention. Such assays are well known in the art, and are described for example in Brophy et al. (1990, Biochem. Biophys. Res. Comm. 167:898-903) and Guechot et al. (1996, Clin. Chem. 42:558-563). Radioimmunoassays are performed, for example, using Iodine-125-labeled primary or secondary antibody (Harlow et al., supra, 1999).

A signal emitted from a detectable antibody is analyzed, for example, using a spectrophotometer to detect color from a chromogenic substrate; a radiation counter to detect radiation, such as a gamma counter for detection of Iodine-125; or a fluorometer to detect fluorescence in the presence of light of a certain wavelength. Where an enzyme-linked assay is used, quantitative analysis is performed using a spectrophotometer. It is understood that the assays of the invention can be performed manually or, if desired, can be automated and that the signal emitted from multiple samples can be detected simultaneously in many systems available commercially.

The methods of the invention also encompass the use of capillary electrophoresis based immunoassays (CEA), which can be automated, if desired. Immunoassays also may be used in conjunction with laser-induced fluorescence as described, for example, in Schmalzing et al. (1997, Electrophoresis 18:2184-2193) and Bao (1997, J. Chromatogr. B. Biomed. Sci. 699:463-480). Liposome immunoassays, such as flow-injection liposome immunoassays and liposome immunosensors, may also be used according to the methods of the invention (Rongen et al., 1997, J. Immunol. Methods 204:105-133).

Quantitative western blotting may also be used to determine the level of AP inhibition in the methods of the invention. Western blots are quantified using well known methods such as scanning densitometry (Parra et al., 1998, J. Vasc. Surg. 28:669-675).

Methods of Administration

The methods of the invention comprise administering a therapeutically effective amount of at least one anti-properdin antibody to an individual identified as having an AP-mediated pathology. In a preferred embodiment the individual is a mammal having an AP system. In a more preferred embodiment the individual is a human.

The methods of the invention can comprise the administration of at least one of any of the anti-properdin antibodies described herein, but the present invention should in no way be construed to be limited to the anti-properdin antibodies described herein, but rather so should be construed to encompass any anti-properdin antibodies, both known and unknown, that diminish and reduce AP activation.

The method of the invention comprises administering a therapeutically effective amount of at least one anti-properdin antibody to an individual wherein a composition of the present invention comprising an anti-properdin antibody, or a combination thereof, is used either alone or in combination with other therapeutic agents. The invention can be used in combination with other treatment modalities, such as, for example antiinflammatory therapies, and the like. Examples of antiinflammatory therapies that can be used in combination with the methods of the invention include, for example, therapies that employ steroidal drugs, as well as therapies that employ non-steroidal drugs.

Pharmaceutical Compositions and Therapies

Administration of an anti-properdin antibody in a method of treatment of the invention can be achieved in a number of different ways, using methods known in the art. The therapeutic and prophylactic methods of the invention thus encompass the use of pharmaceutical compositions comprising an anti-properdin antibody. The pharmaceutical compositions useful for practicing the invention may be administered to deliver a dose of between 1 ng/kg/day and 100 mg/kg/day. In one embodiment, the invention envisions administration of a dose which results in a concentration of the anti-properdin antibody of the present invention between 1 µM and 10 µM in an individual. In another embodiment, the invention envisions administration of a dose which results in a concentration of the anti-properdin antibody of the present invention between 1 µM and 10 µM in the plasma of an individual.

Typically, dosages which may be administered in a method of the invention to an animal, preferably a human, range in amount from 0.5 µg to about 50 mg per kilogram of body weight of the animal. While the precise dosage administered will vary depending upon any number of factors, including but not limited to, the type of animal and type of disease state being treated, the age of the animal and the route of administration. Preferably, the dosage of the compound will vary from about 1 µg to about 10 mg per kilogram of body weight of the animal. More preferably, the dosage will vary from about 3 µg to about 1 mg per kilogram of body weight of the animal.

The compound may be administered to an animal as frequently as several so times daily, or it may be administered less frequently, such as once a day, once a week, once every two weeks, once a month or even less frequently, such as once every several months or even once a year or less. The frequency of the dose will be readily apparent to the skilled artisan and will depend upon any number of factors, such as, but not limited to, the type and severity of the disease being treated, the type and age of the animal, etc. The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Individuals to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, and routes of administration. Other contemplated formulations include projected nanoparticles, liposomal preparations, resealed erythrocytes containing the active ingredient, and immunologically-based formulations.

A pharmaceutical composition of the invention may be prepared, packaged, or sold in bulk, as a single unit dose, or as a plurality of single unit doses. A unit dose is discrete amount of the pharmaceutical composition comprising a predetermined amount of the active ingredient. The amount of the active ingredient is generally equal to the dosage of the active ingredient which would be administered to an individual or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the individual treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

Parenteral administration of a pharmaceutical composition includes any route of administration characterized by physical breaching of a tissue of an individual and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, intraocular, intravitreal, subcutaneous, intraperitoneal, intramuscular, intrasternal injection, and intratumoral.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the so form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

The formulations described herein as being useful for pulmonary delivery are also useful for intranasal delivery of a pharmaceutical composition of the invention.

Another formulation suitable for intranasal administration is a coarse powder comprising the active ingredient and having an average particle from about 0.2 to 500 micrometers. Such a formulation is administered in the manner in which snuff is taken i.e. by rapid inhalation through the nasal passage from a container of the powder held close to the nares.

Formulations suitable for nasal administration may, for example, comprise from about as little as 0.1% (w/w) and as much as 100% (w/w) of the active ingredient, and may further comprise one or more of the additional ingredients described herein.

A pharmaceutical composition of the invention may be prepared, packaged, or sold in a formulation suitable for buccal administration. Such formulations may, for example, be in the form of tablets or lozenges made using conventional methods, and may, for example, 0.1 to 20% (w/w) active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, preferably have an average particle or droplet size in the range from about 0.1 to about 200 nanometers, and may so further comprise one or more of the additional ingredients described herein.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, Pa.), which is incorporated herein by reference.

Human Properdin Mouse

The invention also includes a transgenic mouse that expresses human properdin and does not express mouse properdin. To create a transgenic mouse, a nucleic acid encoding the human properdin protein can be incorporated into a recombinant expression vector in a form suitable for expression of the human properdin protein in a host cell. The term "in a form suitable for expression of the fusion protein in a host cell" is intended to mean that the recombinant expression vector includes one or more regulatory sequences operatively linked to the nucleic acid encoding the human properdin protein in a manner which allows for transcription of the nucleic acid into mRNA and translation of the mRNA into the human properdin protein. The term "regulatory sequence" is art-recognized and intended to include promoters, enhancers and other expression control elements (e.g., polyadenylation signals). Such regulatory sequences are known to those skilled in the art and are described in 1990, Goeddel, Gene Expression Technology: Methods in Enzymology 185, Academic Press, San Diego, Calif. It should be understood that the design of the expression vector may depend on such factors as the choice of the host cell to be transfected and/or the amount of human properdin protein to be expressed.

A transgenic mouse can be created, for example, by introducing a nucleic acid encoding the human properdin protein (typically linked to appropriate regulatory elements, such as a constitutive or tissue-specific enhancer) into oocyte, e.g., by microinjection, and allowing the oocyte to develop in a female foster mouse. Intronic sequences and polyadenylation signals can also be included in the transgene to increase the efficiency of expression of the transgene. Methods for generating transgenic animals, particularly animals such as mice, have become conventional in the art and are described, for example, in U.S. Pat. Nos. 4,736,866 and 4,870,009 and 1986, Hogan et al., A Laboratory Manual, Cold Spring Harbor, N.Y., Cold Spring Harbor Laboratory. A transgenic founder mouse can be used to breed additional animals carrying the transgene. Transgenic mice carrying a transgene encoding the properdin protein of the invention can further be bred to other transgenic mice carrying other transgenes, or to other knockout mice, e.g., a knockout mouse that does not express the murine properdin gene, such as those described in U.S. Pat. App. No. 2010/0263061. It will be understood that in addition to transgenic mice, the system described herein can be used to generate other human properdin expressing animals.

In one embodiment, the transgenic mouse of the invention expresses human properdin from a chicken β-actin promoter with CVM-IE enhancer, but the skilled artisan will understand that the transgenic mouse of the invention encompasses the expression of human properdin from other promoters and enhancers. Examples of promoters useful in the invention include, but are not limited to, DNA pol II promoter, PGK promoter, ubiquitin promoter, albumin promoter, globin promoter, ovalbumin promoter, SV40 early promoter, the Rous sarcoma virus (RSV) promoter, retroviral LTR and lentiviral LTR. Promoter and enhancer expression systems useful in the invention also include inducible and/or tissue-specific expression systems.

In some embodiments, the human properdin that was inserted into the mouse genome comprises the nucleic acid sequence of SEQ ID NO:67 and the amino acid sequence of SEQ ID NO:54.

Kits

The invention also includes a kit comprising an anti-properdin antibody, or combinations thereof, of the invention and an instructional material which describes, for instance, administering the anti-properdin antibody, or a combinations thereof, to an individual as a therapeutic treatment or a non-treatment use as described elsewhere herein. In so an embodiment, this kit further comprises a (preferably sterile) pharmaceutically acceptable carrier suitable for dissolving or suspending the therapeutic composition, comprising an anti-properdin antibody, or combinations thereof, of the invention, for instance, prior to administering the antibody to an individual. Optionally, the kit comprises an applicator for administering the antibody.

Experimental Examples

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Anti-human properdin monoclonal antibodies were generated using the hybridoma method first described by Kohler et al. (1975, Nature, 256:495) with some modifications. Properdin knockout mice (fP$^{-/-}$) (8 weeks old) were intraperitoneally immunized with 50 μg (in 100 μl PBS) purified human properdin (CompTech Inc) emulsified with 100 μl Titermax adjuvant (From Sigma). At day 14 and day 21, the mice were again immunized with 50 μg purified human properdin emulsified with Titermax adjuvant. One week later, the mice were examined for serum anti-properdin titer. Mice with an antibody titer of 1:10,000 or higher were used for hybridoma fusion experiments. Two days prior to fusion experiment, mice were injected (i.p) again with 50 μg purified human properdin (in 100 μl PBS). Mice were sacrificed by cervical dislocation and spleen was isolated for preparation of single cell suspension by mechanical disruption. The spleen cell suspension was washed once with HYB-SFM (Invitrogen)+10% FBS medium and cells were counted, and mixed with X63-Ag8.653 mycloma cells (ATCC) in a 2:1 ratio. Cell mixture was again washed with HYB-SFM medium, and the cell pellet was prepared by centrifugation (1000 rpm×5 min). The cell pellet was gently disturbed and loosened and then cell fusion was induced by slowly adding poly ethylene glycol (PEG 1500) (1.5 ml PEG for 3×10$^8$ cells). The cells were left for 1 min at 37° C. and then 20 ml HYB-SFM medium were added to the cells in 3 min (1 ml for the first min, 3 mls for the second min and 16 mls for the third min). The mixture was centrifuged at 1000 rpm for 5 min and the cells were plated in 24 well plates in HAT medium (10 ml HAT [Sigma H0262], 5 ml Pen/Strep, 500 μl Gentamicin and 10% FBS In 500 ml HYB-SFM medium). After 2 weeks, supernatants from wells with visible colonies were withdrawn for screening of reactivity with purified human properdin by ELISA. Positive clones were picked up and plated in 96 well plates by limiting dilution method to obtain single clones after second round screening by ELISA. Positive clones were expanded in HT-medium (10 ml HT, 5 ml Pen/Strep 500 μl Gentamicin and 10% FBS in 500 ml HYB-SFM medium). Before antibody collection, the hybridoma cells were switched to serum-free medium (HYB-SFM) for 2-3 days. Cell culture medium was collected for mAb purification by protein G affinity chromatography.

To clone the cDNAs of the anti-properdin mAbs, total RNAs were isolated from the hybridoma cells by TRizol reagent (Sigma). First-strand cDNAs were synthesized by reverse transcription using Oligo(dT) primer. To amplify the heavy chain cDNAs (for IgG1, IgG2a/b), the following primers were used in PCR reactions: 5'-GAGGT-GAAGCTGGTGGAG(T/A)C(T/A)GG-3' (SEQ ID NO:68) and 5'-GGGGCCAGTGGATAGAC-3' (SEQ ID NO:69). To amplify the k light chain, the following primers were used: mixture of 4 upstream primers: 5'-CCAGTTCCGAGCTC-CAGATGACCCAGACTCCA-3' (SEQ ID NO:70); 5'-CCAGTTCCGAGCTCGTGCTCACCCAGTCTCCA-3' (SEQ ID NO:71); 5'-CCAGTCCGAGCTCCAGATGAC-CCAGTCTCCA-3' (SEQ ID NO:72); 5'-CCAGTTC-CGAGCTCGTGATGACACAGTCTCCA-3' (SEQ ID NO:73); downstream primer: 5'-GTTGGTGCAG-CATCAGC-3' (SEQ ID NO:74). The PCR amplicons were cloned into pCR TOPO TA 2.1 vector (Invitrogen) and sequenced. To obtain the signal peptide (leader) sequence of the mAbs, the 5'-RACE method was used with a kit (GenCracer) from Invitrogen. The complete variable region cDNAs were amplified using specific primers determined from the 5'-RACE and the initial sequencing data.

Example 2

Figure 1:
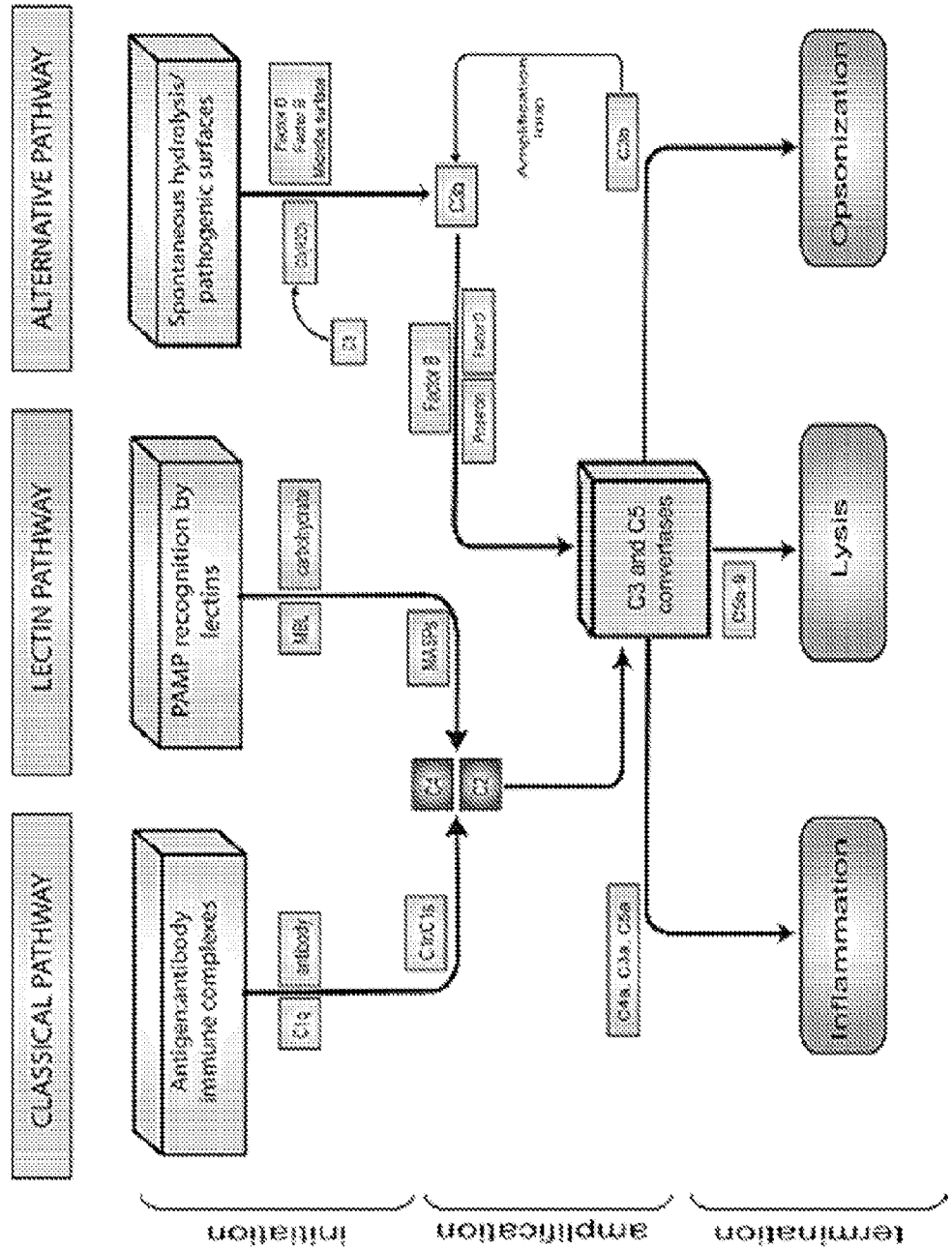
FIG. 1 is a schematic of the complement pathways. Complement can be activated through three pathways: classical, lectin, and alternative. The classical pathway is activated when C1q binds to antibody attached to antigen, activating C1r and C1s which cleave C4 and C2. The lectin pathway is activated when mannose-binding lectin (MBL) encounters conserved pathogenic carbohydrate motifs, activating the MBL-associated serine proteases (MASPs) and again cleaving C4 and C2. C4 and C2 cleavage products form the classical and lectin pathways C3 convertase, C4bC2a which cleaves C3 into C3b and C3a. A second molecule of C3b can associate with C4bC2a to form the C5 convertase of the classical and lectin pathways, C4bC2aC3b. The alternative pathway (AP) is activated when C3 undergoes spontaneous hydrolysis and forms the initial AP C3 convertase, C3(H2O)Bb, in the presence of Factors B and D, leading to additional C3 cleavage and the eventual formation of the AP C3 convertase (C3bBb) and AP C5 convertase (C3bBbC3b). Properdin facilitates AP activation by stabilizing the AP convertases. All three pathways culminate in the formation of the convertases, which in turn generate the major effectors of the complement system: the anaphylatoxins (C4a/C3a/C5a), the membrane attack complex (MAC), and the opsonins (e.g. C3b). The anaphylatoxins are potent proinflammatory molecules derived from cleavage of C4, C3, and C5. The MAC is a terminal assembly of complement components C5b through C9 which can directly lyse targeted surfaces. C3b induces phagocytosis of opsonized targets and also serves to amplify complement activation through the AP.
Figure 2:
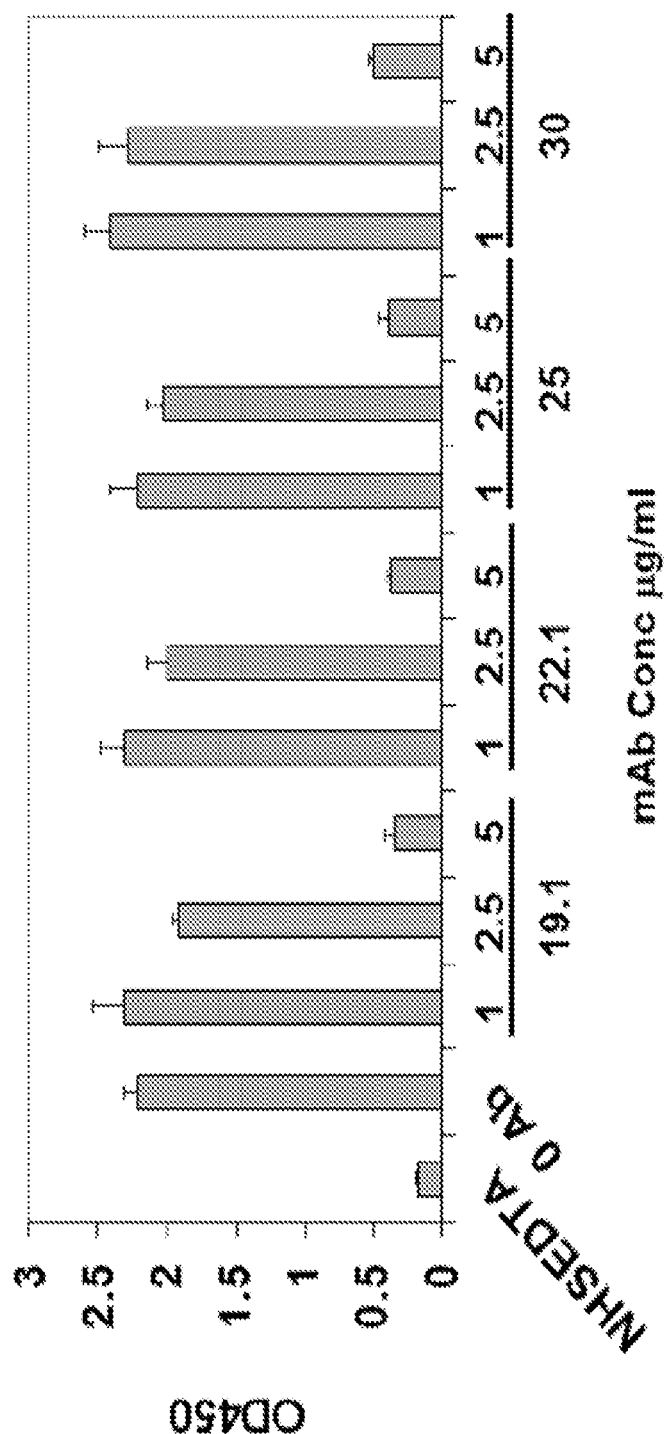
FIG. 2 depicts the results of experiments demonstrating dose-dependent inhibition of LPS-induced AP complement activation by mAb 19.1, 22.1, 25 and 30. All 4 clones of mAbs effectively inhibited AP complement activation when added to 50% normal human serum (NHS) at a final concentration of 5 µg/ml. A sample with EDTA added (NHSEDTA) served as a negative control (EDTA blocks complement activation). A sample with no mAb added (0 Ab) served as the baseline AP complement activation. The experiment was performed in GVB-EGTA-Mg++ buffer. ELISA plates were coated with LPS overnight. NHS was preincubated with mAb before addition to plate. AP complement activation was detected by measuring the amount of C3 deposition on the plate (OD450).

The dose-dependent inhibition of LPS-induced AP complement activation by mAb 19.1, 22.1, 25 and 30 was examined. All 4 clones of mAbs effectively inhibited AP complement activation when added to 50% normal human serum (NHS) at a final concentration of 5 μg/ml (see FIG. 2). ELISA plates (96-well, Nunc) were coated with 50 μl LPS solution (40 μg/ml in phosphate-buffered saline [PBS]) overnight at 4° C. The next day, plates were washed 3× with PBS containing 0.05% Tween-20 (PBS-T) and 50 μl 50% normal human serum (NHS) that had been incubated with 1-5 μg/ml anti-properdin mAb for 1 hour at 4° C. was added. The NHS was diluted with GVB-EGTA-Mg++ (containing 10 mM EGTA and 2.5 mM Mg++ final concentration). The plate was left to incubate at 37° C. for 1 hour, washed 3× with PBS-T and then 50 μl HRP-conjugated goat anti-human C3 antibody (1:4000, Cappel) was added and the plate was left for 1 hour room temperature. The plate was washed 3× with PBS-T and then developed using BD Pharmingen A+B reagent. The reaction was stopped after 5 min with 2 NH2SO4. AP complement activation was detected to by measuring the amount of C3 deposition on the plate (OD450). A sample with EDTA added (NHSEDTA) served as a negative control (EDTA blocks complement activation). A sample with no mAb added (0 Ab) served as the baseline AP complement activation.

Example 3

Experiments demonstrating that anti-human properdin mAbs inhibit human red blood cell (RBC) lysis caused by fH and DAF dysfunction were conducted (see FIG. 3). Normal human RBCs (5×10$^6$ cells) were incubated at 37 C for 20 min with 100 μl 50% NHS (diluted with GVB-EGTA-Mg++ containing 10 mM EGTA and 2.5 mM Mg++ final concentration) in the presence of 30 μM recombinant fH 19-20 and 7.5 μg mouse anti-human DAF (from AbD Serotec) (2006, Ferreira et al., J Immunol. 177:6308-6316). Lysis reaction was stopped by addition of 200 μl ice-cold 20 mM EDTA in PBS. The incubation mixtures were centrifuged for 5 min at 1500 g and the supernatant was collected and measured for OD420 nm. Before addition to RBCs, NHS was pre-incubated with 0 or 5 μg/ml anti-properdin antibodies for 1 hour at 4 C. Samples without NHS or fH 19-20 added or with EDTA added were used as negative lysis controls, and a sample of RBCs lysed completely with 100 μl distilled water was used as a positive control (100% lysis) against which % lysis in other samples was normalized.

Example 4

Figure 4:
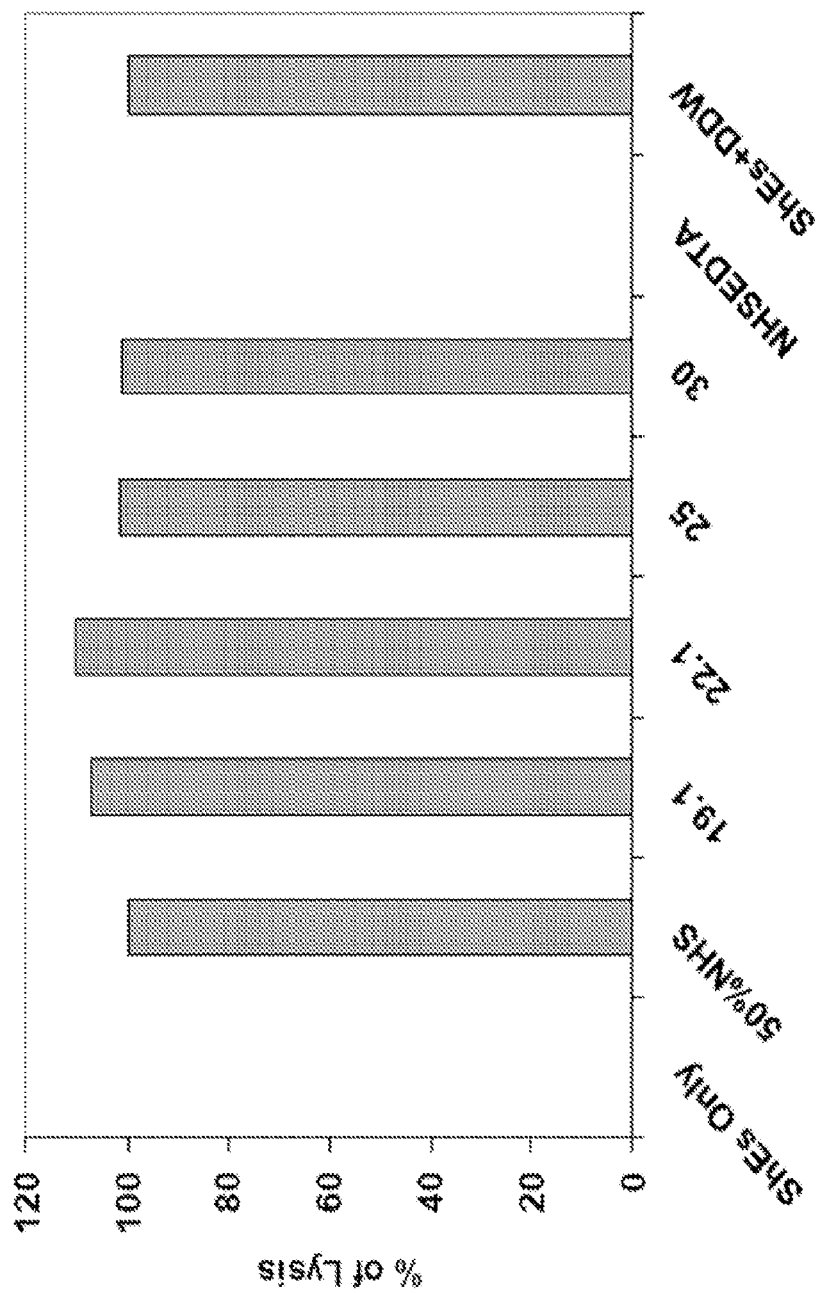
FIG. 4 depicts the results of experiments evaluating antibody-sensitized sheep RBCs incubated with 50% normal human serum (NHS) in the absence or presence of 5 µg/ml of anti-properdin mAbs. A sample of RBCs with no human serum added (ShEs Only) showed no lysis; RBCs incubated with 50% NHS with no anti-properdin mAbs added showed complete lysis (50% NHS); RBCs incubated with 50% NHS and 5 µg/ml of mAbs 19.1, 22.1, 25 or 30 were also completely lysed, demonstrating that the mAbs had no inhibitory effect on classical pathway-mediated complement lysis of sensitized sheep RBCs. RBCs incubated with 50% NHS in the presence of EDTA (NHSEDTA) had no lysis, demonstrating the lysis was mediated by complement; sheep RBCs treated with distilled water (Es+DDW) served as a 100% lysis control.

Experiments evaluating antibody-sensitized sheep RBCs incubated with 50% normal human serum (NHS) in the absence or presence of 5 μg/ml of anti-properdin mAbs (see FIG. 4). Antibody-sensitized sheep RBCs ($5 \times 10^6$ cells, from CompTech Inc) were incubated at 37° C. for 20 min with 100 μl 50% NHS (diluted with GVB++ buffer). Before addition to the sheep RBCs, NHS was pre-incubated with 0 or 5 μg/ml anti-properdin antibody for 1 hour at 4 C. Lysis reaction was stopped by addition of 200 μl ice-cold 20 mM EDTA in PBS. The incubation mixtures were centrifuged for 5 min at 1500 g and the supernatant was collected and measured for OD420 nm. Samples without NHS or with EDTA added were used as negative lysis controls, and a sample of sheep RBCs lysed completely with 100 μl distilled water was used as a positive control (100% lysis) against which % lysis in other samples was normalized.

Example 5

Figure 5C:
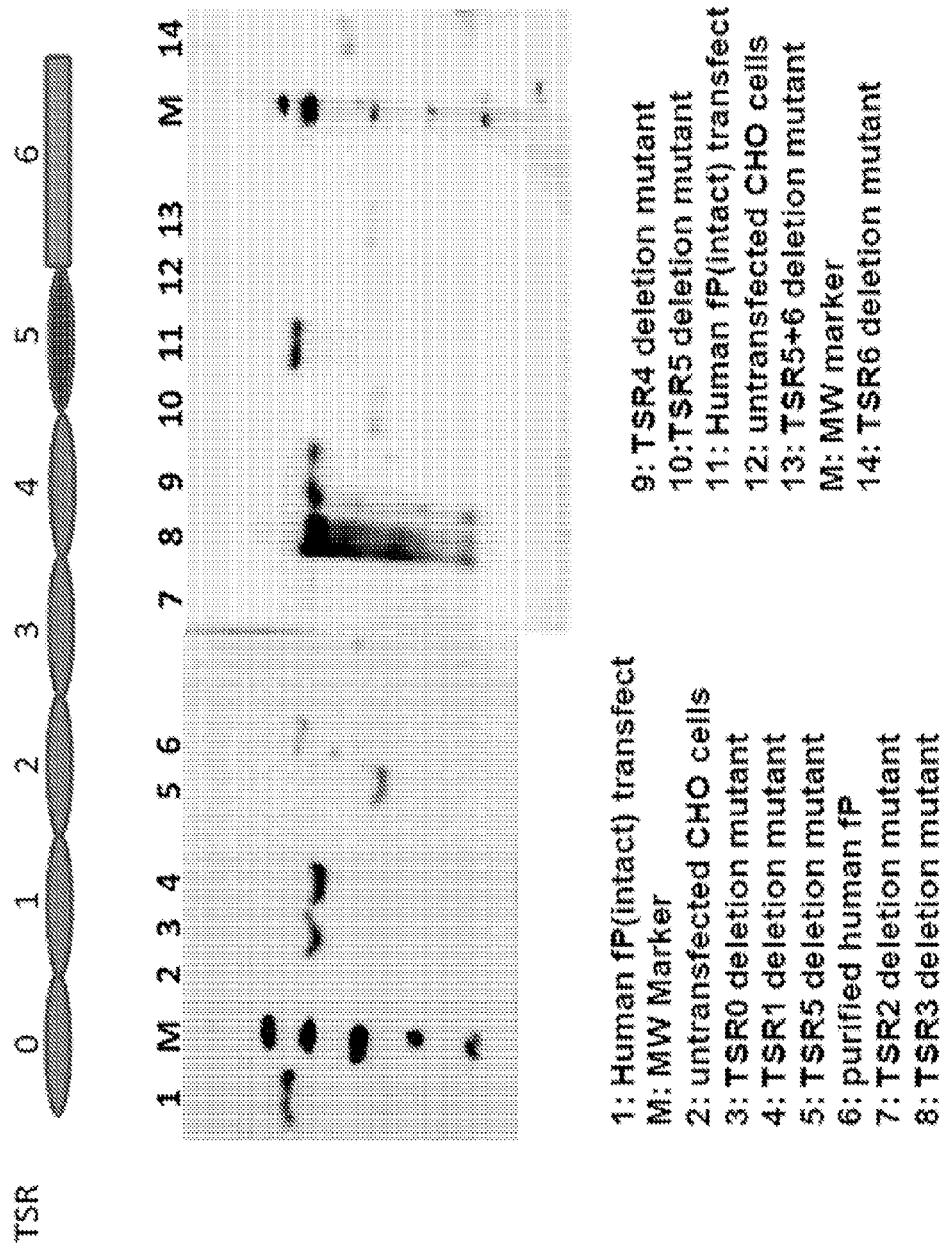

Generation of deletion mutants of human properdin and confirmation by Western blot of their expression in CHO cells (see FIG. 5). Human properdin (fP) is composed of 7 thrombospondin repeat (TSR) domains which are numbered 0 to 6. Individual TSR domains 0 to 5 (see SEQ ID NO:55, 56, 57, 58, 59 and 60) were deleted by inverse PCR (1989, Hemsley et al., Nucleic Acid. 5 Res. 17:6545) using full-length human properdin cDNA (SEQ ID NO:67) in pCMV vector (from Origene) as a template. To delete TSR 6 (SEQ ID NO:61) or TSR 5-6, normal PCR methods was used, followed by cloning into an expression vector (the pCAGGS vector was used). The deletion mutants were transfected into CHO cells using Lipofectamine reagent (Invitrogen) in 6 well plates in Optimem medium. After 48 hours, the cells were lysed with 50 mM Tris-HCL, ph 7.4 containing 150 mM NaCl, 10% glycerol, 1 mM EDTA and a protease inhibitor cocktail (Roche) and 1% Triton X-100 (250 μl per well). The lysate was centrifuged 10,000 rpm for 10 min and protein concentration was determined by BCA protein assay method. About 100 μg total protein from each sample was used for SDS-PAGE analysis.

Example 6

Figure 6:
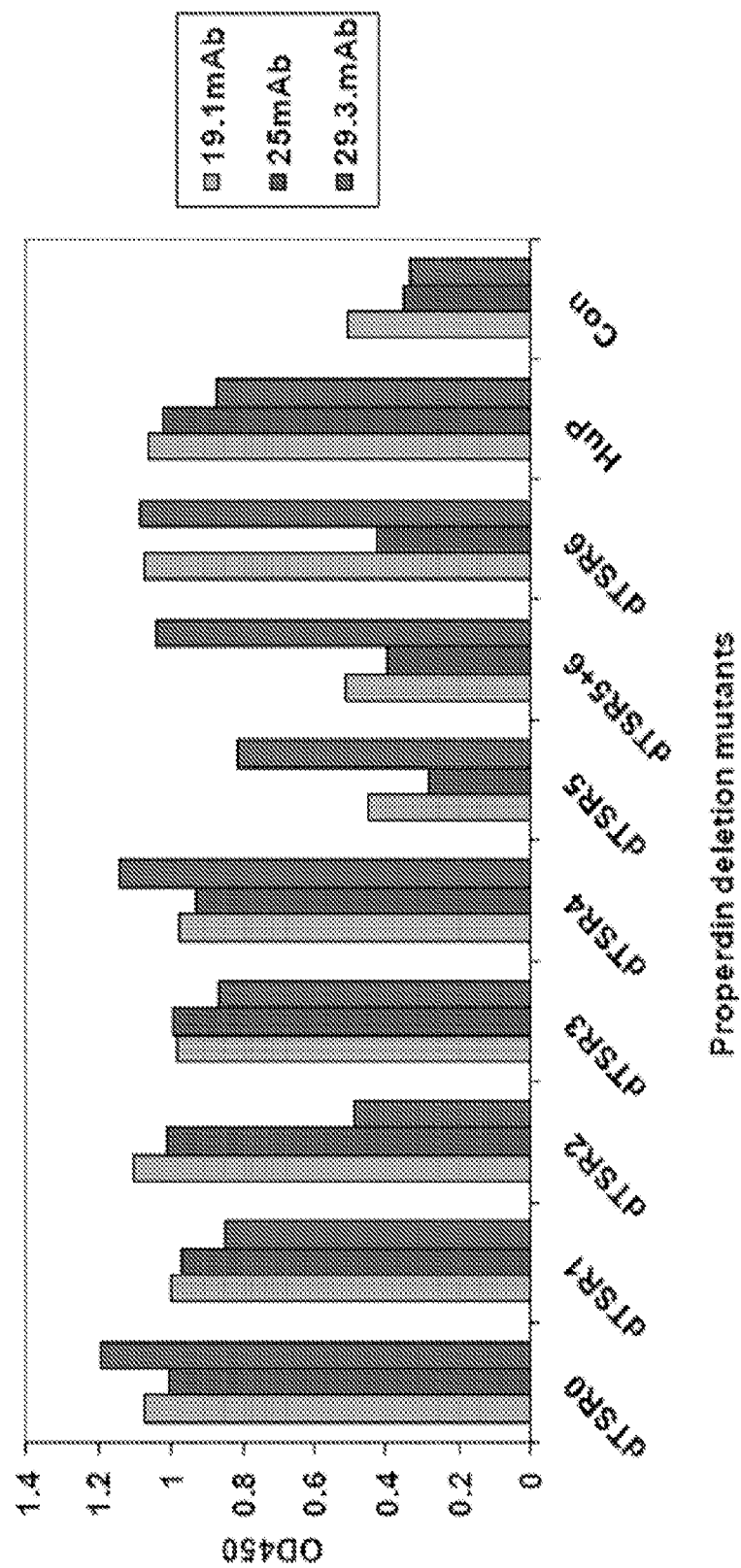
FIG. 6 depicts the results of epitope mapping for mAb 19.1 and 25 and is ELISA assays of mAb 19.1 and 25 binding to human properdin deletion mutants. CHO cell lysates were coated onto ELISA plates and detected with mAb 19.1 or 25. A third mAb 29.3 which binds to a different epitope from 19.1 and 25 was used as a control to confirm protein expression. The results show that both mAb 19.1 and 25 reacted with the following deletion mutants: dTSR0, dTSR1, dTSR2, dTSR3, dTSR4. Thus, it can be concluded that the epitopes for mAb 19.1 and 25 are not located in TSR 0-4. Furthermore, mAb 19.1 lost binding to dTSR5 and dTSR5+6 but retained binding to dTSR6, suggesting that its epitope is located in TSR5. mAb 25 lost binding to dTSR5, dTSR5+6 and dTSR6, suggesting that its epitope is located in TSR 5-6. However, because dTSR5 has undergone proteolytic degradation leading to possible TSR6 removal (FIG. 5), it is likely that the epitope for mAb 25 is located in TSR6. HuP refers to full length human properdin transfection which is used as a positive control. Con refers to untransfected CHO cell lysate which is used as a negative control for lack of binding. All mutant proteins contained a 6×His tag at the C-terminus.

Sandwich ELISA assays of mAb 19.1 and 25 binding to human properdin deletion mutants were performed for epitope mapping of mAb 19.1 and 25. (see FIG. 6). ELISA plates were coated with 50 μl of 2 μg/ml of the concerned mAb overnight at 4° C. The plates were washed 3× with PBS-T and then 25 μg (in 50 μl PBS containing 1% BSA) CHO cell lysate proteins were added to the wells and the plates were incubated for 1 hour at room temperature. The plates were washed 3× with PBS-T and then captured protein was detected by biotinylated goat anti-human properdin antibody and HRP-avidin system. A third mAb 29.3 which binds to a different epitope from 19.1 and 25 was used as a control to confirm mutant protein expression.

Example 7

Figure 7:
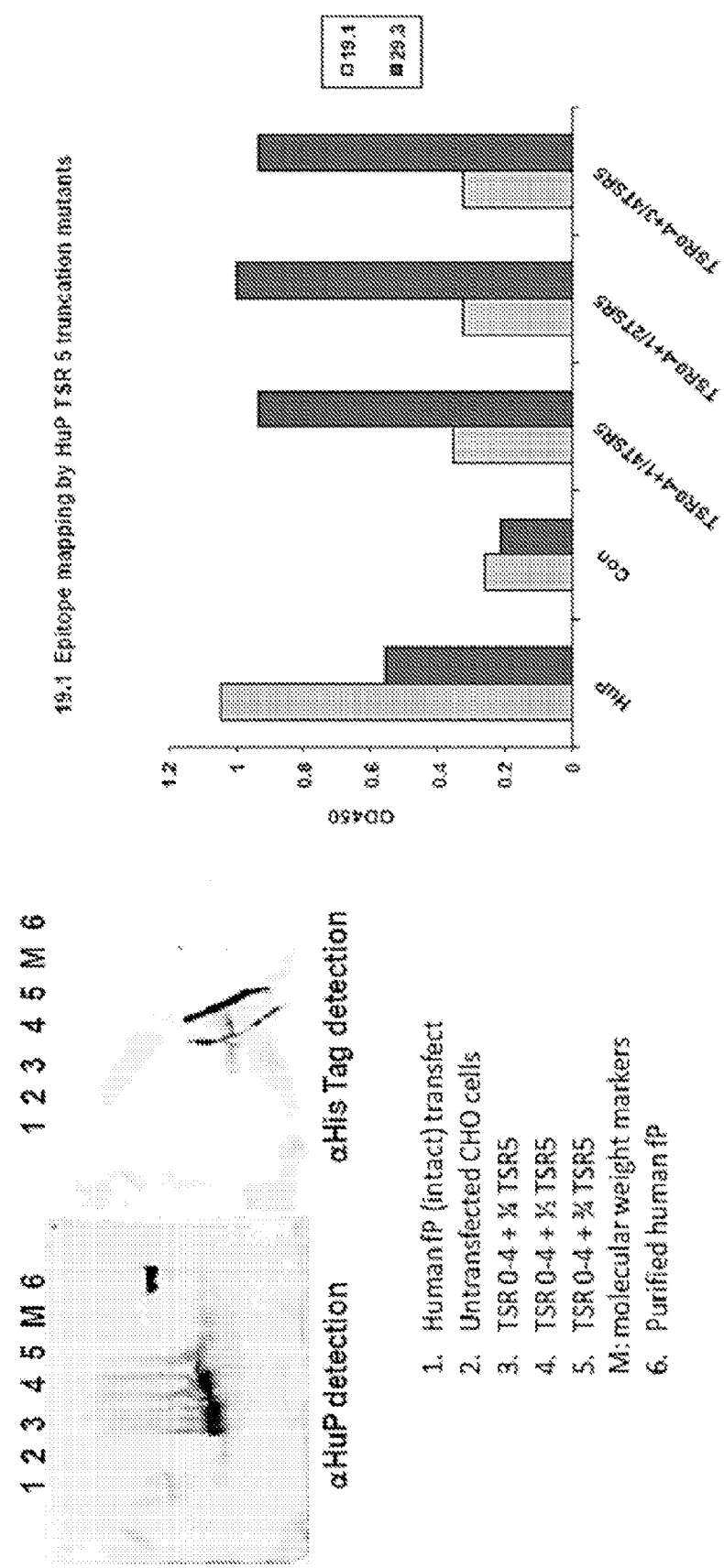
FIG. 7 depicts the results of epitope mapping showing the epitope of mAb 19.1 is mapped to the C-terminal half of TSR5 with the amino acid sequence: so RGRTCR-GRKFDGHRCAGQQQDIRHCYSIQHCP (SEQ ID NO:52). Because TSR0-4 (i.e., dTSR5+6) did not react with mAb 19.1 whereas TSR0-5 (i.e., dTSR6) reacted with 19.1 (FIG. 6), further deletion mutants were generated: TSR0-4+¼TSR5, TSR0-4+½ TSR5 and TSR0-4+¾ TSR5. Mutant, but not intact properdin proteins contained a 6× His tag at their C-terminus. Western blot analysis using both anti-human fP and anti-His tag antibodies showed that TSR0-4+¾ TSR5 was not expressed well. The other two mutants, TSR0-4+¼ TSR5 and TSR0-4+½ TSR5, were confirmed to be expressed but neither one was recognized by mAb 19.1, suggesting they have lost the epitope for mAb 19.1. Thus, it can be concluded that the key epitope residues for mAb 19.1 are located within the C-terminal half of TSR5 (SEQ ID NO:52).

Epitope mapping showed the epitope of mAb 19.1 mapped to the C-terminal half of TSR5 with the following amino acid sequence: RGRTCRGRKFDGHRCA-GQQQDIRHCYSIQHCP (SEQ ID NO:52) (see FIG. 7). Three human properdin mutants comprising TSR0-4+¼ TSR5, TSR0-4+½ TSR5 or TSR0-4+¾ TSR5 were generated by conventional PCR. They were cloned into pCAGGS and expressed in CHO cells as described in Example 5. Protein expression was confirmed by Western analysis using goat anti-human properdin antibody. The blot was stripped and reprobed with a mouse anti-His tag antibody (Qiagen) to confirm that the C-terminal His Tag is present (no C-terminal proteolysis). Sandwich ELISA assays to determine reactivity with mAb 19.1 were performed as described in Example 6. The mAb 29.3 which binds to a different epitope from 19.1 was used as a control to confirm mutant protein expression.

Example 8

Figure 8A:
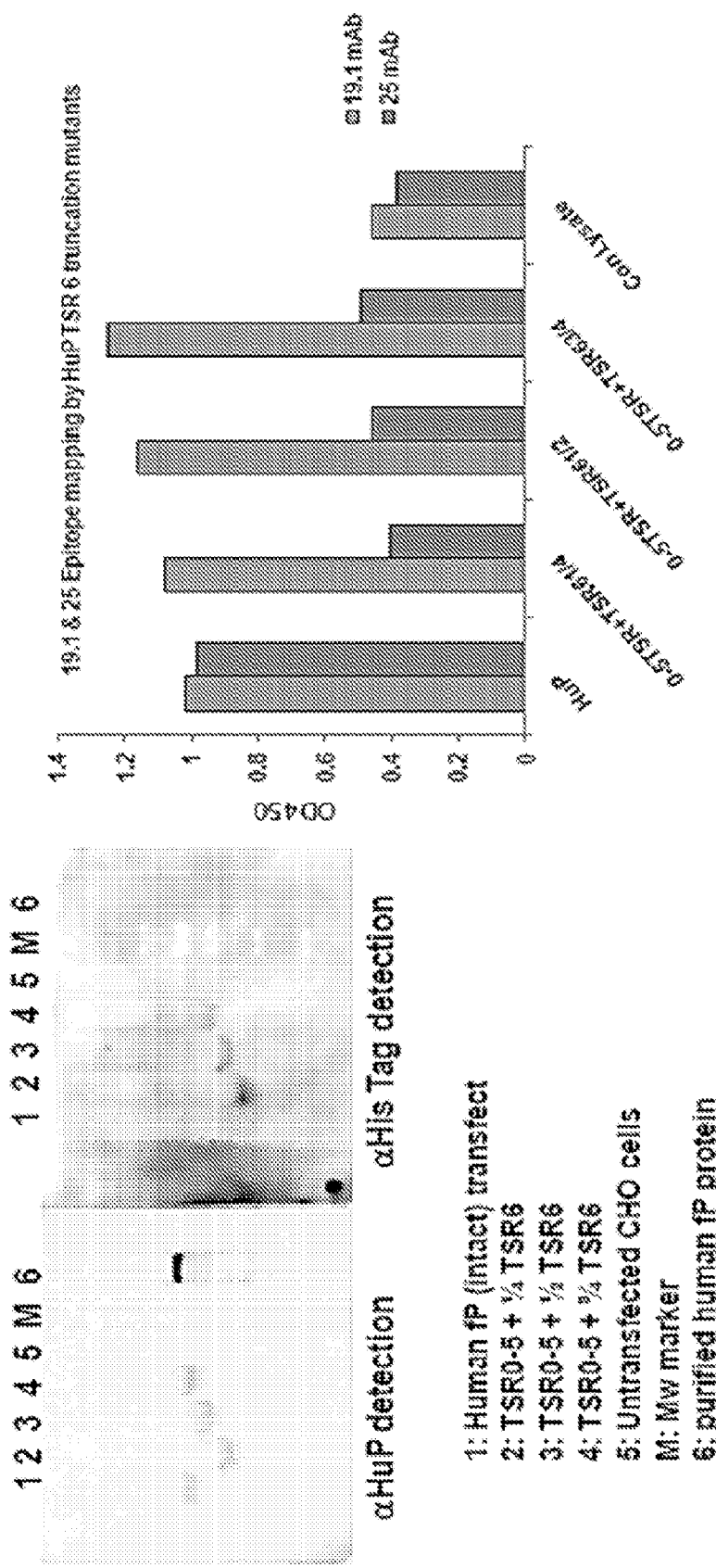
FIGS. 8A and 8B, depicts the results of epitope mapping showing the epitope of mAb 25.
Figure 8B:
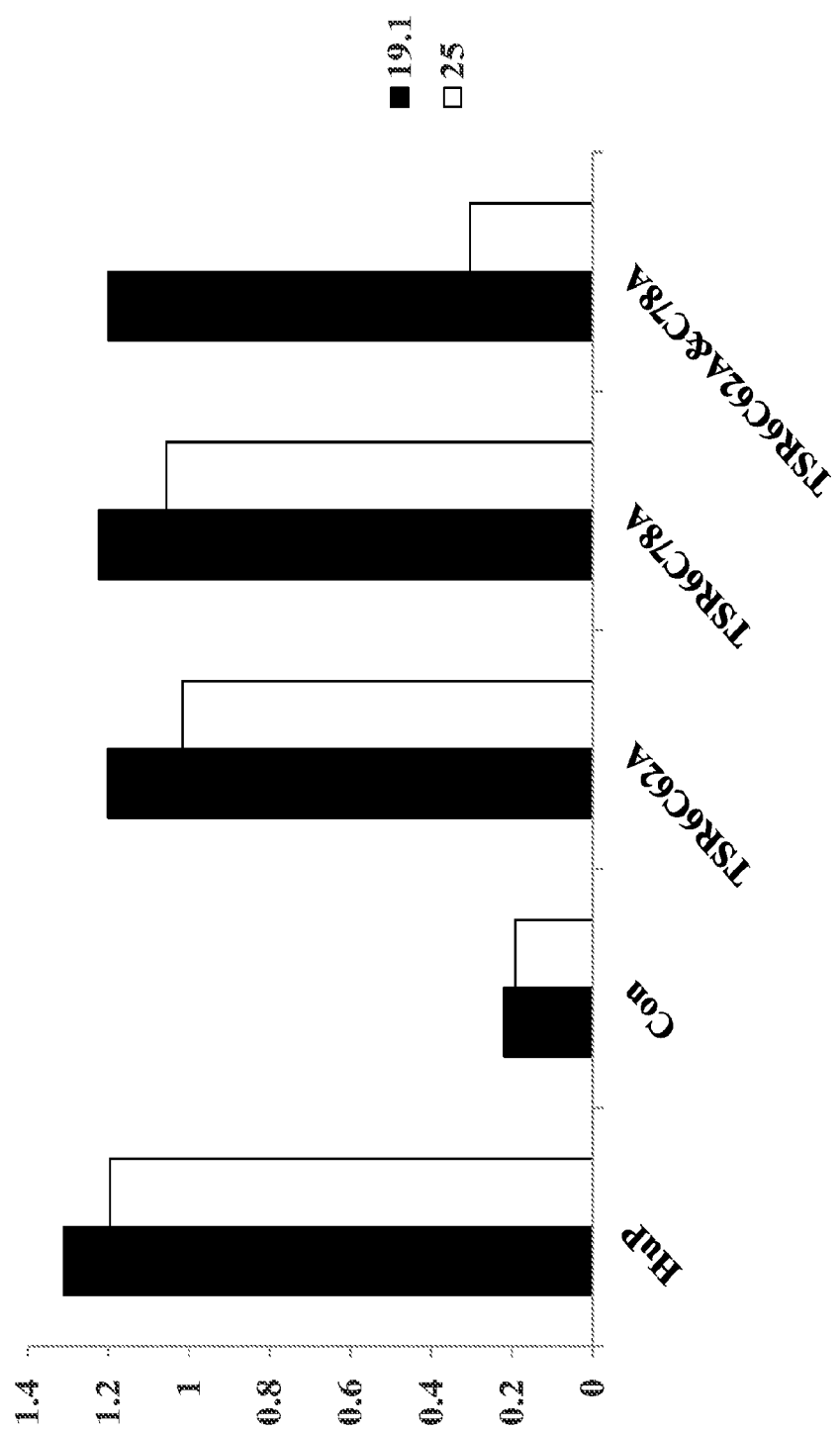

Epitope mapping showed the epitope of mAb 25 mapped to the C-terminal quarter segment of TSR6 with the following amino acid sequence: LVVEEKRPCLHVPACKD-PEEEEL (SEQ ID NO:53) (see FIG. 8). Three human properdin mutants comprising TSR0-5+¼ TSR6, TSR0-5+½ TSR6 or TSR0-5+¾ TSR6 were generated by conventional PCR. They were cloned into pCAGGS and expressed in CHO cells as described in Example 5. Protein expression was confirmed by Western analysis using goat anti-human properdin antibody. The blot was stripped and reprobed with a mouse anti-His tag antibody (Qiagen) to confirm that the C-terminal His Tag is present (no C-terminal proteolysis). Sandwich ELISA assays to determine reactivity with mAb 25 were performed as described in Example 6. mAb 19.1 which binds to a different epitope from 25 was used as a control to confirm mutant protein expression. Epitope mapping also showed that the epitope of mAb 25 is dependent on two cysteine residues in TSR6 (SEQ ID NO: 61, shown in FIG. 5B). These are cysteine 62 (C62) and cysteine 78 (C78) of TSR6. Single mutation to Alanine (A) of either C62 or C78 in full-length human properdin did not abolish mAb 25 binding, but double mutations of C62A and C78A abolished mAb 25 binding. As a positive control for mutant protein expression, mAb 19.1 showed reactivity to all samples. This result suggests that C78 within the last quarter segment of TSR6 (with the sequence designated by SEQ ID NO: 53), as well as C62 which is located outside SEQ ID NO:53 but within TSR6 (SEQ ID: 61), constitute two critical residues of the epitope of mAb 25. Binding assays of mAbs 19.1 and 25 was performed on ELISA plates using homogenates of transfected CHO cells. HuP refers to full-length (intact) human fP transfected CHO cells as a positive control; Con refers to untransfected CHO cells as negative controls for binding. The other samples are CHO cells transfected with mutant human fP cDNA containing single or double C62A and C78A mutations.

Example 9

Figure 17B:
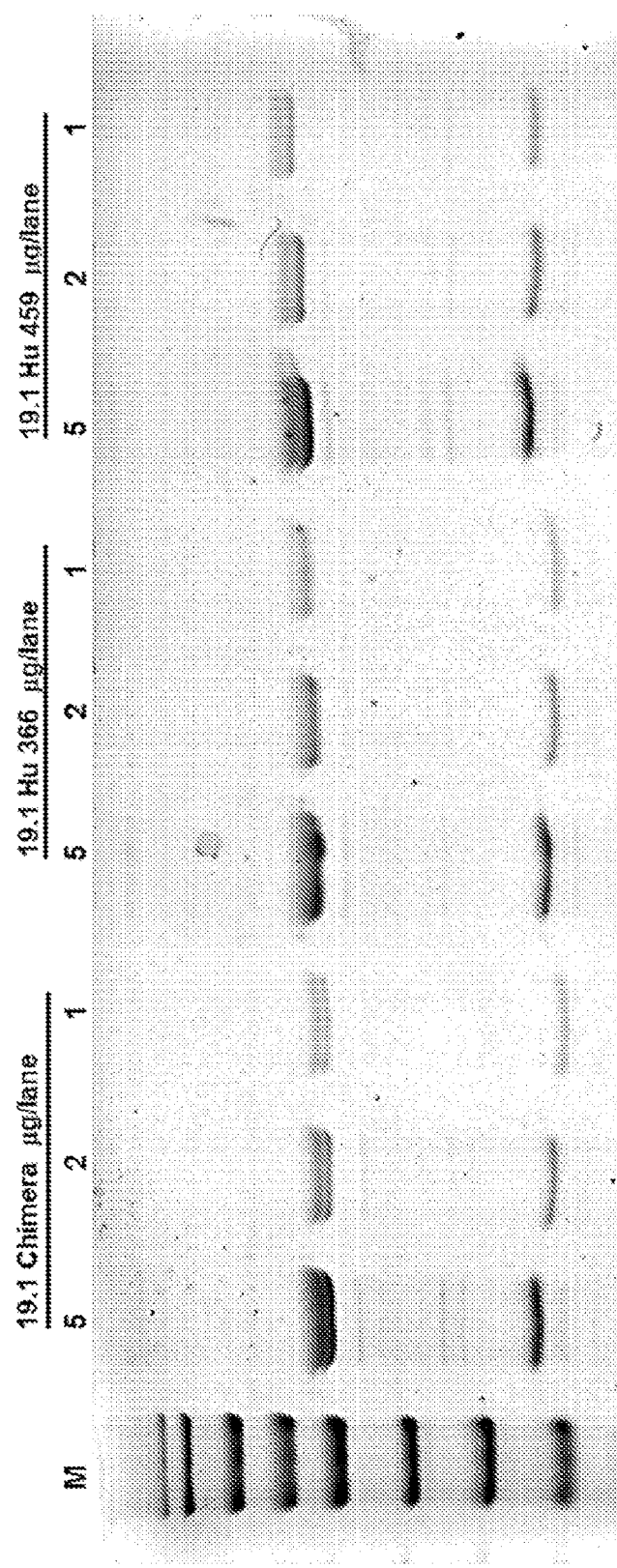

Experiments assessing the expression of recombinant chimeric and humanized 19.1 mAbs in CHO cells were conducted (see FIG. 17). Chimeric 19.1 heavy chain cDNA was constructed by cloning the variable region of mAb 19.1 (SEQ ID NO: 1) into the pFUSE-CHIg-hG4 vector (from InvivoGen, containing the human IgG4 heavy chain constant region, with Serine 229 mutated to Proline) using EcoRI/NheI sites. Chimeric 19.1 light chain cDNA was constructed by cloning the variable region of mAb 19.1 (SEQ ID NO:6) into the pFUSE2-CLIg-hk vector (from InvivoGen, containing the human k light chain constant region) using AgeI/BsiWI sites. Humanized 19.1 heavy chain cDNAs were constructed by cloning the humanized heavy chain variable region of 19.1 (cDNAs encoding SEQ ID NO:42 and SEQ ID NO:44, synthesized by Genescript) into the pFUSE-CHIg-hG4 vector (from InvivoGen, containing the human IgG4 heavy chain constant region, with Serine 229 mutated to Proline) using EcoRI/NheI sites. Humanized 19.1 light chain cDNA was constructed by cloning the humanized light chain variable region of 19.1 (cDNA encoding SEQ ID NO:47, synthesized by Genescript) into the pFUSE2-CLIg-hk vector (from InvivoGen, containing the human k light chain constant region) using AgeI/BsiWI sites. CHO cells were co-transfected with chimeric heavy and light chains of 19.1 or humanized heavy and light chains of 19.1 (the two humanized heavy chains were paired with the same humanized light chain) using Lipofectamine reagent. After transfection, CHO cells were selected with Geocine (1 mg/ml) and Blastcidine (10 µg/ml) for approximately 7 days. Drug-resistant cell colonies were picked up, trypsinized and subjected to limited dilution culture in 96-well plates in the presence of the same selection drugs. After cells became confluent in the 96-well plates, the medium was tested for reactivity with human properdin by ELISA and positive clones were expanded. For antibody production, stable lines of transfected CHO cells were grown in DMEM: F12 medium with 10% FBS in 150 cm culture flasks and after reaching confluence, they were switched to serum free CD-CHO medium (Invitrogen). After 3 days, the medium was collected and mAbs were purified by protein G chromatography. Aliquots of the purified mAbs were analyzed by SDS-PAGE.

Example 10

Figure 18:
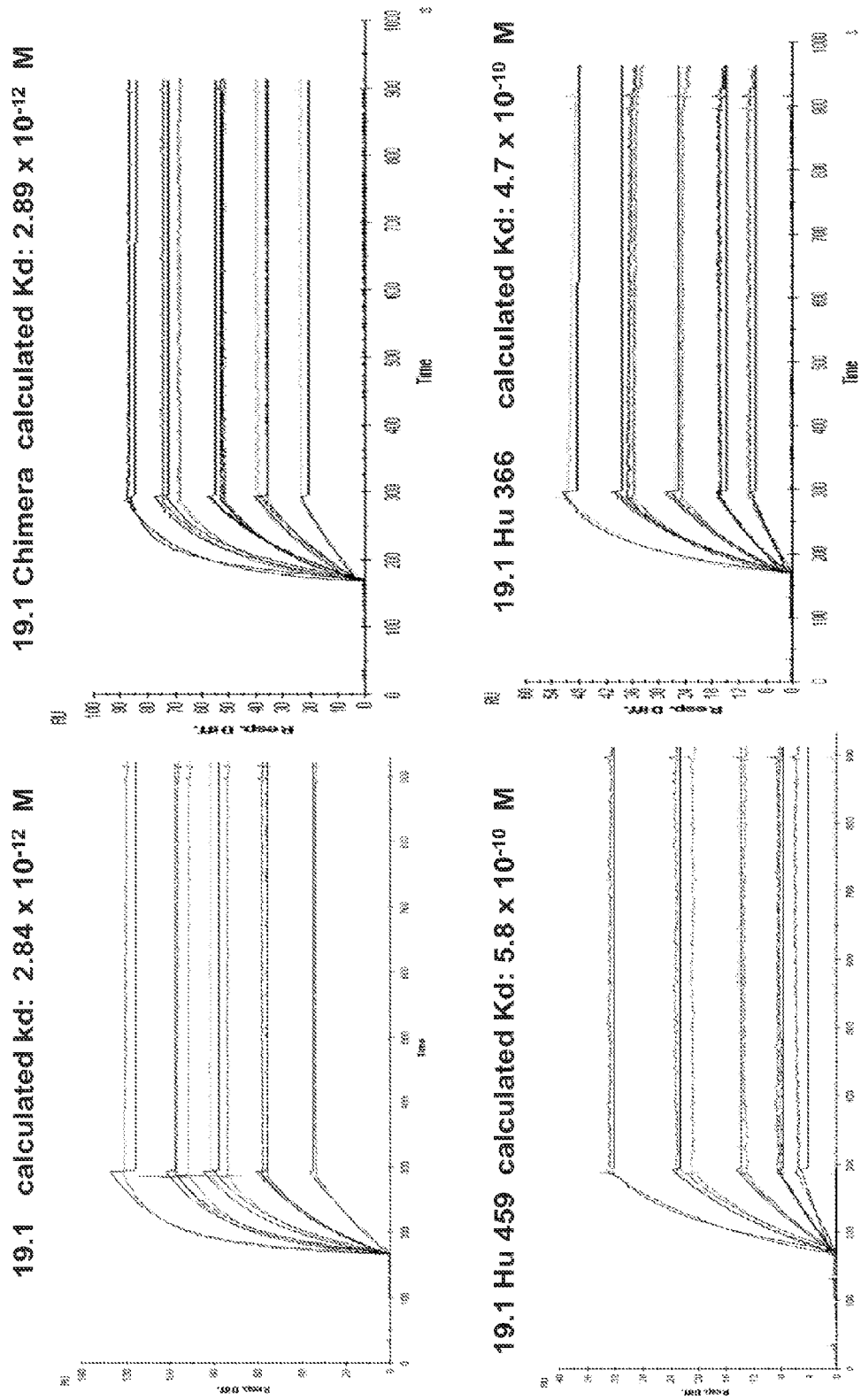
FIG. 18 depicts the results of experiments measuring the antigen binding affinities of 19.1, chimeric 19.1 and humanized 19.1 mAbs using Biacore. Purified human fP was coupled onto CM4 chip using the amine coupling method.

Experiments measuring the antigen binding affinities of mAb 19.1, chimeric mAb 19.1, humanized mAb19.1, mAb 25, mAb 22.1 and mAb 30 were conducted (see FIGS. 18 and 19). Surface Plasmon resonance analysis was used to measure the association and dissociation rate constant for binding of anti-human properdin mAb to immobilized human properdin using BIAcore 2000 instrument (Biacore AB, Uppsala, Sweden). Biacore experiments were performed at 25° C. The carboxylated dextran matrix of a CM4 sensor chip was used to couple the purified human properdin by amine coupling chemistry to obtain 200RU surface density, mAbs were diluted to 150, 75, 35.5, 17.75, 8.87 and 0 nM in HBSET (HEPES buffered saline with EDTA and Tween 20) buffer and the samples were injected onto the properdin surface at 30 µl/min (60 µl injection) for 120 s and dissociation of bound analyte was allowed to proceed for 900 s. The data were analyzed by the BIA evaluation software 3.2 assuming bivalent binding model. Regeneration of the surface was achieved with a 50 µl injection (50 µl/min) of 50 mM NaOH.

Example 11

Experiments were conducted to assess the relative activities of 19.1, chimeric 19.1 and two humanized 19.1 mAbs in blocking LPS-induced human AP complement activation (see FIG. 20). ELISA plates (96-well, Nunc) were coated with 50 µl LPS solution (40 µg/ml in PBS overnight at 4° C.). The next day, plates were washed 3× with PBS containing 0.05% PBS-T and 50 µl 50% NHS that had been incubated with 0, 5, 10 or 20 µg/ml anti-properdin mAb for 1 hour at 4° C. was added. The NHS was diluted with GVB-EGTA-Mg++(containing 10 mM EGTA and 2.5 mM Mg++, final concentration). The plate was left to incubate at 37° C. for 1 hour, washed 3× with PBS-T and then 50 µl HRP-conjugated goat anti-human C3 antibody (1:4000, Cappel) was added and the plate was left for 1 hour room temperature. The plate was washed 3× with PBS-T and then developed using BD Pharmingen A+B reagent. The reaction was stopped after 5 min with 2 $NH_2SO_4$. AP complement activation was detected by measuring the amount of C3 deposition on the plate (OD450). A sample with EDTA added (NHSEDTA) served as a negative control (EDTA blocks complement activation). A sample with no mAb added (NHS) served as the baseline so AP complement activation.

Example 12

Experiments were conducted to assess the relative activities of 19.1, chimeric 19.1 and two humanized 19.1 mAbs in blocking human RBC lysis by human AP complement in the context of fH and DAF dysfunction (see FIG. 21). Normal human RBCs ($5 \times 10^6$ cells) were incubated at 37° C. for 20 min with 100 µl 50% NHS (diluted with GVB-EGTA-Mg++ containing 10 mM EGTA and 2.5 mM Mg++ final concentration) in the presence of 30 µM recombinant fH 19-20 and 7.5 µg mouse anti-human DAF (from ADB Serotec) (2006, Ferreira et al., J Immunol. 177:6308-6316). Before addition to RBCs, NHS was pre-incubated with 1-15 µg/ml various anti-properdin mAbs for 1 hour at 4° C. Lysis reaction was stopped by addition of 200 µl ice-cold 20 mM EDTA in PBS. The incubation mixtures were centrifuged for 5 min at 1500 g and the supernatant was collected and measured for OD420 nm. Samples without NHS or fH19-20 added or with EDTA added were used as negative lysis controls, and a sample of RBCs lysed completely with 100 µl distilled water was used as a positive control (100% lysis) against which % lysis in other samples was normalized.

Example 13

Experiments were conducted to assess the relative activities of 19.1, chimeric 19.1 and two humanized 19.1 mAbs in blocking LPS-induced Rhesus monkey and Cynomolgus monkey AP complement activation (see FIGS. 22 and 23). ELISA plates (96-well, Nunc) were coated with 50 µl LPS solution (40 µg/ml in PBS overnight at 4° C.). The next day, plates were washed 3× with PBS containing 0.05% PBS-T and 50 µl 50% normal Rhesus monkey serum (NRS) or normal Cynomolgus monkey serum (NCS) that had been pre-incubated with 0, 10, 20, 30 or 40 µg/ml anti-properdin mAb for 1 hour at 4° C. was added. The NRS or NCS was diluted with GVB-EGTA-Mg++ (containing 10 mM EGTA and 2.5 mM Mg++, final concentration). The plate was left to incubate at 37° C. for 1 hour, washed 3× with PBS-T and then 50 µl HRP-conjugated goat anti-human C3 antibody (1:4000, Cappel, cross react with monkey C3) was added and the plate was left for 1 hour room temperature. The plate was washed 3× with PBS-T and then developed using BD Pharmingen A+B reagent. The reaction was stopped after 5 min with 2 $NH_2SO_4$. AP complement activation was detected by measuring the amount of C3 deposition on the plate (OD450). A sample with EDTA added (NRSEDTA or NCSEDTA) served as a negative control (EDTA blocks complement activation). A sample with no mAb added (NRS or NCS) served as the baseline AP complement activation.

Example 14

Experiments were conducted to assess the inhibition of acidified serum lysis of PNH red blood cells (Ham's test) by mAb 19.1, 25 and humanized 19.1-459 (see FIG. 24). RBCs from paroxysmal nocturnal hemoglobinuria (PNH) patients were subjected to Ham's acidified serum test in the presence or absence of mAbs. RBCs were incubated with autologous serum (final concentration 83%) at 37° C. for 2 hrs and percent lysis was calculated by measuring the OD405 of the supernatant, normalized to a sample of RBCs completely lysed by distilled water (Eh DDW). The incubation mixture was composed of the following: 240 µl of serum, 25 µl of ⅙ NHCL (or 25 µl saline for negative controls), 12.5 µl of 50% (v/v) RBC suspension, 10 µl mAb in saline. A sample of RBCs incubated with nonacidified autologous serum (NHS) was used as a negative control (background lysis). In the absence of mAbs, about 50% of RBCs were lysed by acidified serum. This lysis was completely inhibited by mAb 19.1 at 8 µg/ml and above concentration, by a humanized 19.1 mAb (#459) at the concentration of 20 µg/ml and by mAb 25 at the concentration of 8 µg/ml and above.

Example 15

A properdin humanized mouse was generated as follows (see FIG. 25). A human fP expression vector was constructed in pACGGS plasmid as illustrated in the schematic in FIG. 25A, using the chicken β-actin promoter with CVM-IE enhancer and the rabbit β-globin polyA tail for stable expression of the cDNA in eukaryotic cells. The human properdin cDNA sequence and its encoded protein sequence used for constructing the expression vector are shown in SEQ ID NO:67 and SEQ ID NO:68. The plasmid was linearized by restriction enzyme digestion and microinjected into the zygotes of C57BL/6 mice to produce human fP transgenic founder mice. By PCR screening (using primers specific to human fP 5'-ATCAGAGGCCTGTGACACC-3' (SEQ ID NO:65) and 5'-CTG CCCTTGTAGCTCCTCA-3' (SEQ ID NO:66) and genomic DNAs isolated from mouse tails), positive founder mice (showing a human fP cDNA fragment of about 800 bp) can be identified. Of 40 mice analyzed, five (#15, 20, 24, 27 and 32) were positive (FIG. 25B, red arrows). Sandwich ELISA assays were performed to detect human fP in the transgenic so positive mice (FIG. 25C). Plate was coated with a non-blocking mAb against human fP (clone 8.1). After incubation with diluted mouse serum (10%), human fP was detected by using an HRP-conjugated goat anti-human fP antibody. Normal human serum (NHS) was used as a positive control. By this method, human fP should be detected in NHS and in the sera of transgene positive mice (e.g. 15, 20, 24, 27, 32) but not in normal (i.e. non-transgenic, e.g. 29) mouse or fP$^{-/-}$-mouse serum. Transgenic positive founder mice were then bred with WT mice to establish germline transmission. The screening of F1 mice from such mating was accomplished by PCR of tail DNA to detect the transgene and by sandwich ELISA to detect human properdin in their sera as described above. After confirming germline transmission, founder mice were bred with fP$^{-/-}$ mice to generate fP$^{-/-}$-human fP transgene+ mice. Restoration of AP complement activity in fP$^{-/-}$-human fP transgene+ mice was assessed by LPS-induced AP activation assays as described in Example 2. In this assay, AP complement activity should be detected in WT mouse serum and in the serum of fP$^{-/-}$ mice that are human fP transgene positive but not in the serum of fP$^{-/-}$ mice. In this assay, WT mouse serum treated with EDTA will be used as a negative control for AP complement activation.

Example 16

Experiments were conducted to examine the in vivo activity and kinetics of mAb 25 in "properdin humanized" mice (FIG. 26). A properdin humanized mouse (fP$^{-/-}$-human fP transgene+) was injected with 0.5 mg (i.p.) of mAb 25. Blood samples (50-75 µl) were collected before injection (0 hr) and then at various time points after injection by retro-orbital bleeding and sera prepared. Serum samples were tested for LPS-induced AP complement activation. For this assay, ELISA plates (96-well, Nunc) were coated with 50 µl LPS solution (40 µg/ml in PBS overnight at 4° C.). The next day, plates were washed 3× with PBS containing 0.05% Tween-20 (PBS-T) and 50 µl serially diluted (starting from 1:10) mouse serum was added to each well. The mouse serum was diluted with GVB-EGTA-Mg++ (containing 10 mM EGTA and 2.5 mM Mg++ final concentration). The plate was left to incubate at 37° C. for 1 hour, washed 3× with PBS-T and then 50 µl HRP-conjugated rabbit anti-mouse C3 antibody (1:2000, Cappel) was added and the plate was left for 1 hour room temperature. The plate was washed 3× with PBS-T and then developed using BD Pharmingen A+B reagent. The reaction was stopped after 5 min with 2 NH2SO4. AP complement activation was detected by measuring the amount of C3 deposition on the plate (OD450). In this illustrated example, no AP complement activity was present in fP$^{-/-}$ mouse serum or in WT serum treated with EDTA. In contrast, AP complement activity was detected in WT serum and in the serum of fP humanized mouse at time 0 hr (before mAb 25 treatment). AP complement activity in the humanized mouse remained suppressed at 8, 24 and 48 hrs after mAb 25 treatment but became detectable at 72, 96 and 120 hrs. These results demonstrate that at a dosage of 0.5 mg/mouse, mAb 25 was able to inhibit AP complement activity in vivo for at least 48 hrs.

Example 17

Experiments were conducted to assess the effect of anti-human properdin mAb 19.1 on extravascular hemolysis (EVH). In this EVH model, properdin humanized mice (n=4 per experimental group) were transfused with red blood cells (RBC) from Crry/DAF/C3 triple knockout (TKO) mice. Recipient mice (properdin humanized mice) were treated 6 hrs before RBC transfer with mAb 19.1 (2 mg/mouse, i.p.) or a control mouse IgG1 mAb (MOPC, purified from MoPC 31C hybridoma, from ACT). RBCs were harvested from donor TKO mice, washed in PBS and labeled with CFSE before injection (through tail vein) into recipient mice, according to previously published procedure (Miwa et al., 2002, Blood 99: 3707-3716). Each recipient mouse received RBCs equivalent to 100 µl of blood. At 5 minutes and 6, 24, 48, 72, 96, 120 hours after RBC transfusion, recipient mice were bled and RBCs were analyzed to determine the number of CFSE-labeled (i.e. transfused) RBCs remaining in the circulation. Number of CFSE-labeled RBCs in each recipient was normalized (as %) to that detected at the 5 min time point. In control IgG (MOPC)-treated recipient mice, TKO RBCs were rapidly eliminated through EVH, consistent with previous findings (Miwa et al., 2002, Blood 99: 3707-3716). However, in recipient mice treated with anti-human properdin 19.1 mAb, no EVH occurred and the transfused RBCs persisted, demonstrating that anti-properdin mAb was effective in preventing EVH (FIG. 27).

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising an antibody that specifically binds to human properdin wherein:
   the antibody comprises a variable heavy chain comprising VH-CDR1: SEQ ID NO:3; VH-CDR2: SEQ ID NO:4; and VH-CDR3: SEQ ID NO:5; and comprises a variable light chain comprising VL-CDR1: SEQ ID NO:8; VL-CDR2: SEQ ID NO:9 and VL-CDR3: SEQ ID NO:10, or
   the antibody comprises a variable heavy chain comprising VH-CDR1: SEQ ID NO:13; VH-CDR2: SEQ ID NO:14; and VH-CDR3: SEQ ID NO:15; and comprises a variable light chain comprising VL-CDR1: SEQ ID NO:18; VL-CDR2: SEQ ID NO:19; and VL-CDR3: SEQ ID NO:20, or
   the antibody comprises a variable heavy chain comprising VH-CDR1: SEQ ID NO:23; VH-CDR2: SEQ ID NO:24; and VH-CDR3; SEQ ID NO:25; and comprises a variable light chain comprising VL-CDR1: SEQ ID NO:28; VL-CDR2: SEQ ID NO:29; and VL-CDR3: SEQ ID NO:30, or
   the antibody comprises a variable heavy chain comprising VH-CDR1: SEQ ID NO:33; VH-CDR2: SEQ ID NO:34; and VH-CDR3: SEQ ID NO:35; and comprises a variable light chain comprising CDRs VL-CDR1: SEQ ID NO:38; VL-CDR2: SEQ ID NO:39; and VL-CDR3: SEQ ID NO:40.

2. The composition of claim 1, wherein the antibody comprises a heavy chain comprising the amino acid sequence of SEQ ID NO:2 and a light chain comprising the amino acid sequence of SEQ ID NO:7.

3. The composition of claim 1, wherein the antibody specifically binds to an epitope comprising the amino acid sequence of SEQ ID NO:52.

4. The composition of claim 1, wherein the antibody comprises a heavy chain comprising the amino acid sequence of SEQ ID NO:12 and a light chain comprising the amino acid sequence of SEQ ID NO:17.

5. The composition of claim 1, wherein the antibody specifically binds to an epitope comprising the amino acid sequence of SEQ ID NO:53.

6. The composition of claim 1, wherein the antibody comprises a heavy chain comprising the amino acid sequence of SEQ ID NO:22 and a light chain comprising the amino acid sequence of SEQ ID NO:27.

7. The composition of claim 1, wherein the antibody comprises a heavy chain comprising the amino acid sequence of SEQ ID NO:32 and a light chain comprising the amino acid sequence of SEQ ID NO:37.

8. The composition of claim 1, wherein the antibody comprises a heavy chain comprising the amino acid sequence of SEQ ID NO:42 and a light chain comprising the amino acid sequence of SEQ ID NO:47.

9. The composition of claim 1, wherein the antibody comprises a heavy chain comprising the amino acid sequence of SEQ ID NO:44 and a light chain comprising the amino acid sequence of SEQ ID NO:47.

10. The composition of claim 1, wherein the antibody comprises a heavy chain comprising the amino acid sequence of SEQ ID NO:49 and a light chain comprising the amino acid sequence of SEQ ID NO:51.

11. The composition of claim 1, wherein the antibody comprises a light chain comprising the amino acid sequences of SEQ ID NO:7 and SEQ ID NO:64.

12. The composition of claim 1, wherein the antibody comprises a heavy chain comprising the amino acid sequences of SEQ ID NO:2 and SEQ ID NO:63 and a light chain comprising the amino acid sequences of SEQ ID NO:7 and SEQ ID NO:64.

13. The composition of claim 1, wherein the antibody comprises a heavy chain comprising the amino acid sequences of SEQ ID NO:12 and SEQ ID NO:63 and a light chain comprising the amino acid sequences of SEQ ID NO:17 and SEQ ID NO:64.

14. The composition of claim 1, wherein the antibody comprises a heavy chain comprising the amino acid sequences of SEQ ID NO:22 and SEQ ID NO:63 and a light chain comprising the amino acid sequences of SEQ ID NO:27 and SEQ ID NO:64.

15. The composition of claim 1, wherein the antibody comprises a heavy chain comprising the amino acid sequences of SEQ ID NO:32 and SEQ ID NO:63 and a light chain comprising the amino acid sequences of SEQ ID NO:37 and SEQ ID NO:64.

16. A method of treating an alternative pathway (AP)-mediated pathology in an individual, comprising the step of administering to said individual the antiproperdin antibody of claim 1.

17. The method of claim 16, wherein the pathology is at least selected from the group consisting of: macular degeneration, ischemia reperfusion injury, arthritis, rheumatoid arthritis, paroxysmal nocturnal hemoglobinuria (PNH) syndrome, atypical hemolytic uremic (aHUS) syndrome, asthma, organ transplantation sepsis, inflammation, glomerulonephritis, lupus, and combinations thereof.

18. The method of claim 16, wherein the anti-properdin antibody selectively inhibits the alternative pathway, but does not inhibit the classical pathway and the lectin pathway.

19. The method of claim 16, wherein the anti-properdin antibody does not affect the AP amplification loop of the classical pathway and the lectin pathway.

20. The method of claim 16, wherein administration of the antiproperdin antibody inhibits the generation of a C3bBb protein.

* * * * *